US011981904B2

(12) United States Patent
Karlen et al.

(10) Patent No.: US 11,981,904 B2
(45) Date of Patent: May 14, 2024

(54) BAHD ACYLTRANSFERASES

(71) Applicants: WISCONSIN ALUMNI RESEARCH FOUNDATION, Madison, WI (US); THE UNIVERSITY OF BRITISH COLUMBIA, Vancouver (CA)

(72) Inventors: Steven D. Karlen, Madison, WI (US); Rebecca Anne Smith, Madison, WI (US); John Ralph, Madison, WI (US); Emily Beebe, Stoughton, WI (US); Craig Bingman, Fitchburg, WI (US); Brian Fox, Madison, WI (US); Shawn Mansfield, Vancouver (CA); Heather Mackay, Vancouver (CA); Hoon Kim, Madison, WI (US); Yaseen Mottiar, Vancouver (CA); Faride Unda, Vancouver (CA)

(73) Assignees: Wisconsin Alumni Research Foundation, Madison, WI (US); The University of British Columbia, Vancouver (CA)

( * ) Notice: Subject to any disclaimer, the term of this patent is extended or adjusted under 35 U.S.C. 154(b) by 258 days.

(21) Appl. No.: 17/291,932

(22) PCT Filed: Nov. 8, 2019

(86) PCT No.: PCT/US2019/060554
§ 371 (c)(1),
(2) Date: May 6, 2021

(87) PCT Pub. No.: WO2020/097518
PCT Pub. Date: May 14, 2020

(65) Prior Publication Data
US 2022/0002744 A1    Jan. 6, 2022

Related U.S. Application Data

(60) Provisional application No. 62/757,804, filed on Nov. 9, 2018.

(51) Int. Cl.
*C12N 15/82*    (2006.01)
*C07K 14/41*    (2006.01)
*C07K 14/415*   (2006.01)
*C12N 9/10*     (2006.01)

(52) U.S. Cl.
CPC ........ *C12N 15/8255* (2013.01); *C07K 14/415* (2013.01); *C12N 9/1029* (2013.01); *C12N 15/8223* (2013.01); *C12Y 203/01196* (2013.01)

(58) Field of Classification Search
None
See application file for complete search history.

(56) References Cited

U.S. PATENT DOCUMENTS

| | | |
|---|---|---|
| 4,490,838 A | 12/1984 | Akira et al. |
| 5,258,300 A | 11/1993 | Glassman et al. |
| 5,384,253 A | 1/1995 | Krzyzek et al. |
| 5,472,869 A | 12/1995 | Krzyzek et al. |
| 5,489,520 A | 2/1996 | Adams et al. |
| 5,538,877 A | 7/1996 | Lundquist et al. |
| 5,538,880 A | 7/1996 | Lundquist et al. |
| 5,550,318 A | 8/1996 | Adams et al. |
| 5,641,673 A | 6/1997 | Brand et al. |
| 5,985,557 A | 11/1999 | Brow et al. |
| 6,001,567 A | 12/1999 | Brow et al. |
| 7,705,215 B1 | 4/2010 | Adams et al. |
| 8,481,593 B2 | 7/2013 | Okombi et al. |
| 8,569,465 B2 | 10/2013 | Ralph et al. |
| 9,089,499 B2 | 7/2015 | Okombi et al. |
| 9,428,763 B2 * | 8/2016 | Sanz Molinero .. C12N 15/8271 |
| 9,441,235 B2 * | 9/2016 | Wilkerson ............... C08H 6/00 |
| 9,487,794 B2 | 11/2016 | Wilkerson et al. |
| 9,493,783 B2 | 11/2016 | Wilkerson et al. |
| 2006/0159283 A1 | 7/2006 | Alexandrov et al. |
| 2007/0183996 A1 | 8/2007 | Okombi et al. |
| 2007/0283460 A9 | 12/2007 | Liu et al. |
| 2008/0112245 A1 | 5/2008 | Ostermayr et al. |
| 2011/0237551 A1 | 9/2011 | Okombi et al. |
| 2013/0272983 A1 | 10/2013 | Okombi et al. |
| 2015/0020234 A1 | 1/2015 | Wilkerson et al. |

(Continued)

FOREIGN PATENT DOCUMENTS

| | | |
|---|---|---|
| EP | 0 154 204 B1 | 2/1985 |
| EP | 0 218 571 A2 | 4/1987 |

(Continued)

OTHER PUBLICATIONS

Liu et al., 2019, De novo assembly of white poplar genome and genetic diversity of white poplar population in Irtysh River basin in China. Sci China Life Sci 62, 609-618. (Year: 2019).*
Predicted_ Populus alba benzyl alcohol O-benzoyltransferase-like (LOC1—Nucleotide—NCBI_98PCT). (Year: 2020).*
Lu et al. , 2015, Naturally p-hydroxybenzoylated lignins in palms. BioEnergy Research, 8, 934-952. (Year: 2015).*
Guo et al., 2004, Protein tolerance to random amino acid change. Proceedings of the National Academy of Sciences, 101(25), 9205-9210. (Year: 2004).*

(Continued)

*Primary Examiner* — Cathy Kingdon Worley
*Assistant Examiner* — Santosh Sharma
(74) *Attorney, Agent, or Firm* — Daniel A. Blasiole; DeWitt LLP

(57) ABSTRACT

The invention is directed to BAHD acyltransferase enzymes, nucleic acids encoding BAHD acyltransferase enzymes, and inhibitory nucleic acids adapted to inhibit the expression and/or translation of BAHD acyltransferase RNA; expression cassettes, plant cells, and plants that have or encode such nucleic acids and enzymes; and methods of making and using such nucleic acids, enzymes, expression cassettes, cells, and plants.

63 Claims, 15 Drawing Sheets

Specification includes a Sequence Listing.

(56) References Cited

U.S. PATENT DOCUMENTS

| | | |
|---|---|---|
| 2015/0307892 A1 | 10/2015 | Bartley et al. |
| 2015/0376640 A1 | 12/2015 | Shoresh et al. |
| 2016/0046955 A1 | 2/2016 | Wilkerson et al. |
| 2016/0251672 A1 | 9/2016 | Loque et al. |
| 2017/0218004 A1 | 8/2017 | Wilkerson et al. |
| 2018/0298353 A1 | 10/2018 | Beebe et al. |

FOREIGN PATENT DOCUMENTS

| | | |
|---|---|---|
| EP | 321 201 A2 | 6/1989 |
| EP | 0 604 662 A1 | 6/1994 |
| EP | 0 672 752 A1 | 9/1995 |
| WO | WO 1995/06128 A2 | 3/1995 |
| WO | WO 2012/012698 A1 | 1/2012 |
| WO | WO 2012/012741 A1 | 1/2012 |
| WO | WO 2013/052660 A1 | 4/2013 |
| WO | WO 2013/090814 A3 | 6/2013 |
| WO | WO 2014/100742 A2 | 6/2014 |

OTHER PUBLICATIONS

D'Auria, 2006, Acyltransferases in plants: a good time to be BAHD. Current opinion in plant biology, 9(3), 331-340. (Year: 2006).*

Zhao et al., 2021, Monolignol acyltransferase for lignin p-hydroxybenzoylation in Populus. Nature Plants, 7(9), 1288-1300. (Year: 2021).*

Chedgy, R. J. (2015). The role of BAHD acyltransferases in poplar (*Populus* spp.) secondary metabolism and synthesis of salicinoid phenolic glycosides (Doctoral dissertation, University of Victoria). (Year: 2015).*

Phytozome gene report for Potri.001G448000 in Phytozome (http://www.phytozome.net/) (Accessed Jun. 12, 2023) (Year: 2023).*

Stanton et al., 2009, Populus breeding: from the classical to the genomic approach. In Genetics and genomics of Populus (pp. 309-348). New York, NY: Springer New York. (Year: 2009).*

Zhao et al., 2021, Monolignol acyltransferase for lignin p-hydroxybenzoylation in Populus (Supplementary Information). Nature Plants, 7(9), 1288-1300. (Year: 2021).*

NCI Dictionary of Cancer Terms "recombinant". National Cancer Institute, https://www.cancer.gov/publications/dictionaries/cancer-terms/def/recombinant, Accessed Jun. 14, 2023. (Year: 2023).*

Karlen, 2017, Highly decorated lignins in leaf tissues of the Canary Island date palm Phoenix canariensis. Plant physiology, 175(3), 1058-1067. (Year: 2017).*

Alexandrov et al. (NCBI, GenBank Sequence Accession No. EU970537.1, Published Dec. 10, 2008).

Alexandrov et al. Insights into corn genes derived from large-scale cDNA sequencing, *Plant Mol. Biol.*, (2009) 69 (1-2), 179-194.

Alexandrov et al. (GenBank Sequence Accession No. ACG42655; pp. 1-2; 2008).

Altschul S, Gish W, Miller W, Myers E, Lipman D., Basic local alignment search tool. (1990) J Mol Biol 215(3), 403-410.

An. S.M., et al., Binary ti vectors for plant transformation and promoter analysis, *Methods in Enzymology*. (1987) 153:292.

An. S.M., et al., p-Coumaric acid, a constituent of *Sasa quelpaertensis* Nakai, inhibits cellular melanogenesis stimulated by alpha-melanocyte stimulating hormone, *Brit J Dermatol.*, (2008) 159(2), 292-299.

Bell-Lelong et al., Cinnamate-4-hydroxylase expression in *Arabidopsis*: regulation in response to development and the environment, Plant Physiol. (1997) 113, 729-738.

Bevan et al., Structure and transcription of the nopaline synthase gene region of T-DNA, *Nucleic Acid Research*. (1983)11:369-385.

Beuerle and Pichersky, Anal. Biochem. 302(2): 305-12 (2001).

Bodini et al., Quorum sensing inhibition activity of garlic extract and p-coumaric acid, *Lett Appl Microbiol.* (2009) 49(5), 551-555.

Boerjan et al., Lignin biosynthesis, *Annual Reviews in Plant Biology* (2003) 54, 519-546.

Bork et al., Go hunting in sequence databases but watch out for the traps, *TIG*, (1996) 12:425-427.

Cabrita et al., Conversion of hydroxycinnamic acids into volatile phenols in a synthetic medium and red wine by Dekkera bruxellensis. *Ciencia e Tecnologia de Alimentos, Campinas.* (2012) 32(1):106-11.

Camacho et al., BLAST+: architecture and applications, *BMC Bioinformatics*. (2009) 10:421.

Cech Science, The chemistry of self-splicing RNA and RNA enzymes, 236:1532-1539 (1987).

Cech. Ann. Rev. Biochem., Self-splicing of group I introns, 59:543-568 (1990).

Cech, Thomas R. Ribozyme engineering. Curr. Opin. Struct. Biol. 2:605-609 (1992).

Chandler et al., Two regulatory genes of the maize anthocyanin pathway are homologous: Isolation of B utilizing R genomic sequences, *The Plant Cell*. (1989) 1:1175-1183.

Christou et al., Stable transformation of soybean by electroporation and root formation from transformed callus, *PNAS*. (1987) 84:3962-3966.

Claverie and States, Information Enhancement Methods for Large Scale Sequence Analysis, *Comput. Chem.* (1993) 17:191-201.

Clough et al., Floral dip: A simplified method for *Agrobacterium*-mediated transformation of *Arabidopsis thaliana*, Plant Journal (1998) 16, 735-743.

Coe et al., in *Corn and Corn Improvement*, eds. Sprague, G.F. & Dudley, J.W. (Am. Soc. Agron., Madison, WI), pp. 81-258 (1988).

Corpet, Multiple sequence alignment with hierarchial clustering, *Nucleic Acids Res.* (1988) 16:10881-90.

Coruzzi et al., Tissue-specific and light-regulated expression of a pea nuclear gene encoding the small subunit of ribulose-1,5-bisphosphate carboxylas, *EMBO J.* (1984) (8):1671-1679).

Couture and Stinchcomb, Anti-gene therapy: the use of ribozymes to inhibit gene function, Trends Genet. 12:510-515 (1996).

Current Protocols in Molecular Biology, Chapters 2 and 19, Ausubel, et al., eds, Greene Publishing and Wiley-Interscience, New York (1995).

Da Costa Sousa et al., Next-Generation ammonia pretreatment enhances cellulosic biofuel production,. *Energy Environ. Sci.* (2016), 9, 1215-1223.

Dekeyser et al., Transient gene expression in intact and organized rice tissues, *The Plant Cell*. (1990) 2:591-602.

Dellaporta et al., In: *Chromosome Structure and Function: Impact of New Concepts*, 18th Stadler Genetics Symposium, J.P. Gustafson and R. Appels, eds. (New York: Plenum Press) (1988) pp. 263-282.

Doerks et al., Protein annotation: detective work for function prediction, *TIG*, (1998) 14:248-250.

Ebert et al., Identification of an essential upstream element in the nopaline synthase promoter by stable and transient assays, *Proc. Natl. Acad. Sci. USA*. (1987) 84:5745-5749.

Elbashir et al. Duplexes of 21-nucleotide RNAs mediate RNA interference in cultured mammalian cells, (2001) Nature 411:494-498.

Eudes et al., Exploiting members of the BAHD acyltransferase family to synthesize multiple hydroxycinnamate and benzoate conjugates in yeast, *Microb Cell Fact* (2016) 15:198.

Feng and Doolittle, Progressive Sequence Alignment as a Prerequisite to Correct Phylogenetic Trees, *J. Mol. Evol.*, (1987) 25:351-60.

Ferguson et al., Bacterial antimutagenesis by hydroxycinnamic acids from plant cell walls, *Mutation Research-Genetic Toxicology and Environmental Mutagenesis* (2003) 542(1-2), 49-58.

Ferguson et al., Antioxidant and antigenotoxic effects of plant cell wall hydroxycinnamic acids in cultured HT-29 cells. *Molecular Nutrition & Food Research* (2005) 49(6), 585-593.

Fire et al. Potent and specific genetic interference by double-stranded RNA in Caenorhabditis elegans, (1998) Nature 391:806-811.

Gordon Kamm et al., Transformation of maize cells and regeneration of fertile transgenic plants, *The Plant Cell*. (1990) 2:603 618.

(56) References Cited

OTHER PUBLICATIONS

Grefen et al., A ubiquitin-10 promoter-based vector set for fluorescent protein tagging facilitates temporal stability and native protein distribution in transient and stable expression studies, *The Plant Journal* (2010) 64, 355-365.
Guo et al. Protein tolerance to random amino acid change, *PNAS* (2004) 101:9205-9210, 2004.
Grishok et al., Genetic requirements for inheritance of RNAi in C. elegans, Science 287(5462):2494-7 (2000).
Grishok et al. Genes and mechanisms related to RNA interference regulate expression of the small temporal RNAs that control C. elegans developmental timing, (2001) Cell 106:23-34.
Hamilton & Baulcombe, A species of small antisense RNA in posttranscriptional gene silencing in plants, Science 286(5441):950-952 (1999).
Haseloff et al., Simple RNA enzymes with new and highly specific endoribonuclease activities, Nature 334:585-591 (1988).
Hatfield et al., Composition of cell walls isolated from cell types of grain sorghum stems, *J. Sci. Food Agric.* (1999) 79: 891-899.
Hayashimoto et al., A polyethylene glycol-mediated protoplast transformation system for production of fertile transgenic rice plants, *Plant Physiol.* (1990) 93:857-863.
Helm, R. F., Ralph, J., and Hatfield, R.D., Synthesis of feruloylated and p-coumaroylated methyl glycosides. (1992) Carbohydr. Res. 229(1), 183.194.
Henikoff and Henikoff, Amino acid substitution matrices from protein blocks, *Proc. Natl. Acad. Sci. USA* (1989) 89:10915.
Higgins and Sharp, Clustal: a package for performing multiple sequence alignment on a microcomputer, *Gene* (1988) 73:237-44.
Higgins and Sharp, Fast and sensitive multiple sequence alignments on a microcomputer, *Cabios Communications* (1989) 5:151-3.
Hinchee et al., Production of transgenic soybean plants using *Agrobacterium*-mediated DNA transfer, *Bio/Technology.* (1988) 6:915-922.
Holmberg et al., Syringyl methacrylate, a hardwood lignin-based monomer for high-Tg polymeric materials, *ACS Macro Letters* (2016) 5(5), 574-578.
Horsch et al., Somatic embryogenesis from cultured leaf segments of *Zea mays, Science* (1985) 227:1229-1231.
Hsiao & Chiang, Lignins from the Wood of *Aralia Bipinnata, Phytochemistry*, (1995) 39: 899-902.
Huang et al., Parallelization of a local similarity algorithm, *Computer Applications in the Biosciences* (1992) 8:155-65.
Hudspeth et al., Structure and expression of the maize gene encoding the phosphoenolpyruvate carboxylase isozyme involved in C4 photosynthesis, *Plant Molecular Biology.* (1989) 12:579-589.
Ikuta et al., The α-Amylase gene as a marker for gene cloning: Direct screening of recombinant clones, *Bio/Technology* (1990) 8:241-242.
Jefferson, Assaying Chimeric genes in Plants: The GUS Gene Fusion System, *Plant Molecular Biology Reporter* (1987) 5:387-405.
Kaneko et al., Thermotropic liquid-crystalline polymer derived from natural cinnamoyl biomonomers. (2004) *Macromol Rapid Comm* 25(5), 673-677.
Karimi M, Inze D 5 Depicker A. (2002) GATEWAY vectors for Agrobacterium-mediated plant transformation. Trends in Plant Science 7(5):193-195).
Karlen, S. D. et al., Monolignol ferulate conjugates are naturally incorporated into plant lignins. *Science Advances* (2016) 2 (10), e1600393:1600391-1600399.
Karlen, S.D., Smith, R.A., Kim, H , Padmakshan, D., Bartuce, A., Mobley, J.K., Free, H.C.A., Smith, B.G., Harris, P.J. and Ralph, J. (2017) Highly decorated lignins occur in leaf base cell walls of the Canary Island date palm Phoenix canadensis. Plant Physiology, 175:1058-1067.
Katz et al., Cloning and expression of the tyrosinase gene from *StreptomyKellces antibioticus* in *Streptomyces lividans, J. Gen. Microbiol.* (1983) 129:2703 2714.

Keller et al., Vascular expression of a bean cell wall glycine-rich protein—glucuronidase gene fusion in transgenic tobacco, *EMBO J.* (1989) 8:1309-1314.
Keskin et al. A new, structurally nonredundant, diverse data set of protein-protein interfaces and its implications, *Protein Science*, (2004) 13:1043-1055.
Ketting et al. Mut-7 of C. elegans, required for transposon silencing and RNA interference, is a homolog of Werner syndrome helicase and RNaseD , (1999) Cell 99:133-141.
Kim et al., Solution-state 2D NMR of ball-milled plant cell wall gels in DMSO-$d_6$/pyridine-$d_5$, *Org. Biomol. Chem.* (2010) 8(3), 576-591.
Kim et al., Impact of lignin polymer backbone esters on ionic liquid pretreatment of poplar, *Biotechnology for Biofuels* (2017) 10(1):101.
Kim, H., Ralph, J., and Akiyama, T. (2008) Solution-state 2D NMR of Ball-milled Plant Cell Wall Gels in DMSO-d6. BioEnergy Research 1(1 ):56-66.
Kumar, P.; Barrett, D. M.; Delwiche, M. J.; Stroeve, P. (2009) Methods for Pretreatment of Lignocellulosic Biomass for Efficient Hydrolysis and Biofuel Production . Industrial A Engineering Chemistry Research 48(8):3713-3729.
Lawton et al., Expression of a soybean β-conclycinin gene under the control of the Cauliflower Mosaic Virus 35S and 19S promoters in transformed petunia tissues, *Plant Molecular Biology*. (1987) 9:315-324.
Li et al., Time-course accumulation of main bioactive components in the rhizome of Ligusticum chuanxiong, *Planta medica* (2006) 72.03: 278-280.
Li and Zhang, Reverse genetics by fast neutron mutagenesis in higher plants, 2002, Fund Integr Genomics 2:254-258.
Lin and Avery, RNA interference. Policing rogue genes, (1999) Nature 402:128-129.
Liu et al., Application of CRISPR/Cas9 in plant biology, *Acta pharm. Sinica B*, (2017) 7(3): 292-302.
Lu, F., and Ralph, J. Facile synthesis of 4-hydroxycinnamyl p-coumarates. (1998) J. Agr. Food Chem. 46(8), 2911-2913.
Lu et al., Derivatization followed by reductive cleavage (DFRC Method), A new method for lignin analysis: protocol for analysis of DFRC monomers, *Journal of Agricultural and Food Chemistry* (1997) 45, 2590-2592.
Lu et al., Detection and determination of p-coumaroylated units in lignins, *Journal of Agricultural and Food Chemistry* (1999) 47, 1988-1992.
Lu et al., Non-degradative dissolution and acetylation of ball-milled plant cell walls; high-resolution solution-state NMR, *Plant J.* (2003) 35(4), 535-544).
Lu, F., Karlen, S.D., Regner, M., Kim, H., Ralph, S.A., Sun, R.C., Kuroda, K.I., Augustin, M.A., Mawson, R., Sabarez, H., Singh, T., Jimenez-Monteon, G., Hill, S., Harris, PL., Boeijan, W., Mansfield, S.D. and Ralph, J. (2015) Naturally p-hydroxybenzoylated lignins in palms. Bioenerg Res. 8:934-952.
Luterbacher et al., Nonenzymatic sugar production from biomass using biomass-derived γ-valerolactone, *Science* (2014) 343.6168:277-280.
Luterbacher et al., Solvent-enabled nonenyzmatic sugar production from biomass for chemical and biological upgrading, *ChemSusChem* (2015) 8.8:1317-1322.
Luterbacher et al., Lignin monomer production integrated into the γ-valerolactone sugar platform, *Energy and Environmental Science* (2015) 8(9), 2657-2663.
Makino et al., Cell-free protein synthesis for functional and structural studies, *Methods in Molecular Biology* (2014) 1091, 161-178.
Mansfield, S.D., Kim, H., Lu, F. and Ralph, J. (2012) Whole plant cell wall characterization using solution-state 2D-NMR. Nature Protocols, 7:1579-1589.
Martinez et al. Single-stranded antisense siRNAs guide target RNA cleavage in RNAi, Cell 110(5):563 (2002).
Marita et al., Identification and suppression of the p-coumaroyl CoA:hydroxycinnamyl alcohol transferase in Zea mays L. Plant J. (2014) 78 (5), 850-864.
McCabe et al., Stable transformation of soybean (glycine max) by particle acceleration, *Bio/Technology* (1988) 6:923-926.

(56) References Cited

OTHER PUBLICATIONS

McCallum et al. Targeted screening for induced mutations, (2000) Nat Biotech 18:455.
McCallum et al. Targeting induced local lesions IN genomes (TILLING) for plant functional genomics, (2000) Plant Physiol. 123:439-442.
McConnell et al., Role of PHABULOSA and PHAVOLUTA in determining radial patterning in shoots, *Nature* (2001) 411:709-713.
McElroy et al., Isolation of an Efficient Actin Promoter for Use in Rice Transformation, *The Plant Cell* (1990) 2:163-171.
Meinkoth and Wahl, Hybridization of Nucleic Acids immobilized on Solid Supports, *Anal. Biochem.* (1984) 138:267-84.
Mellmer et al. Effects of γ-valerolactone in hydrolysis of lignocellulosic biomass to monosaccharides, *Green Chemistry* (2014) 16.11:4659-4662.
Meyer et al., Lignin monomer composition is determined by the expression of a cytochrome P450-dependent monooxygenase in *Arabidopsis, Proc. Natl. Acad. Sci. USA* (1998) 95(12), 6619-6623.
Montgomery et al. RNA as a target of double-stranded RNA-mediated genetic interference in Caenorhabditis elegans, (1998) Proc. Natl. Acad. Sci. USA. 95:15502-15507.
Murakami et al., The bialaphos biosynthetic genes of Streptomyces hygroscopicus: Molecular cloning and characterization of the gene cluster, *Mol. Gen. Genet.* (1986) 205:42 50.
Nagata et al., Synthesis and characterization of photocrosslinkable biodegradable polymers derived from 4-hydroxycinnamic acid, *Macromol Biosci* (2003) 3(8), 412-419.
Nambudiri et al., Conversion of p-coumarate into caffeate by Streptomyces nigrifaciens. Purification and properties of the hydroxylating enzyme,. *Biochem J.* (1972)130(2):425-33.
Needleman and Wunsch, A General Method Applicable to the Search for Similarities in the Amino Acid Sequence of Two Proteins, *J. Mol. Biol.* (1970) 48:443-53.
Ngo et al., The Protein Folding Problem and Tertiary Structure Prediction, K. Merz., and S. Le Grand (eds.) (1994) pp. 492-495.
Niedz et al., Green fluorescent protein: an in vivo reporter of plant gene expression, *Plant Cell Reports* (1995) 14:403.
Nishimura et al., Over-Expression of Tobacco knotted1-Type Class1 Homeobox Genes Alters Various Leaf Morphology, *Plant Cell Physiol.*, (2000) 41(5):583-590.
Odell et al., Identification of DNA sequences required for activity of the cauliflower mosaic virus 35S promoter, *Nature* (1985) 313:810-812.
Ow et al., Transient and stable expression of the firefly luciferase gene in plant cells and transgenic plants, *Science* (1986) 234:856-859.
Patterson et al., Hypothetical protein SORBIDRAFT_09g002910 [Sorghum bicolor] (NCBI, Gen Bank Sequence Accession No. XP_002439238.1 Published Jul. 13, 2009).
Paula et al., Lignans from *Ochroma lagopus* Swartz, *Tetrahedron* (1995) 51.45:12453-12462.
PCT International Search Report and Written Opinion, dated Mar. 25, 2020, PCT/US19/60554.
Pearson and Lipman, Improved tools for biological sequence comparison, *Proc. Natl. Acad. Sci. USA* (1988) 85:2444.
Pearson, Using the FASTA Program to Search Protein and DNA Sequence Databases, *Meth. Mol. Biol.* (1994) 24:307-31.
Petrik et al., p-Coumaroyl-CoA:Monolignol Transferase (PMT) acts specifically in the lignin biosynthetic pathway in *Brachypodium distachyon, The Plant Journal* (2014) 77(5), 713-726.
Petrik et al. *BdCESA7, BdCESA8*, and *Bd*PMT utility promoter Reconstructs for targeted expression to secondary cell-wall-forming cells of grasses, (2016) *Frontiers in Plant Science* (2016) 7, 1-14.
Potrykus et al., Direct gene transfer to cells of a graminaceous monocot, *Mol. Gen. Genet.* 199:183-188 (1985).
Potrykus I., Gene transfer to cereals: an assessment, *Trends Biotech.* (1989) 7:269-273.
Prasher et al., Cloning and expression of the cDNA Coding for Aequorin, a Bioluminescent Calcium-Binding Protein, *Biochem. Biophys. Res. Comm.* (1985) 126:1259-1268.

Ralph et al., Pathway of p-coumaric acid incorporation into maize lignin as revealed by NMR, *J. Am. Chem. Soc.* (1994) 116: 9448-9456.
Ralph et al., Lignins: natural polymers from oxidative coupling of 4-hydroxyphenylpropanoids, *Phytochem. Revs.* (2004) 3(1), 29-60.
Ralph, J., Brunow, G., and Boerjan, W. (2007) Lignins. In: Rose, F., and Osborne, K. (eds). Encyclopedia of Life Sciences, DOI: 10.1002/9780470015902.a0020104, John Wiley & Sons, Ltd., Chichester, UK.
Razzaghi-Asl et al., Antioxidant properties of hydroxycinnamic acids: A review of structure-activity relationships, *Current Medicinal Chemistry* (2013) 20(36), 4436-4450.
Regner, M., Bartuce, A., Padmakshan, D., Ralph, J. and Karlen, S.D. (2018) Reductive cleavage method for quantitation of monolignols and low-abundance monolignol conjugates. ChemSusChem 11:1600-1605.
Rinaldi et al. (2016) Paving the way for lignin valorisation: Recent Advances in Bioengineering, Biorefining and Catalysis. Angew Chem Int Ed Engl. 55(29):8164-8215).
Sambrook et al. (Molecular Cloning: A Laboratory Manual. Second Edition (Cold Spring Harbor, NY: Cold Spring Harbor Press (1989).
Sambrook et al., Molecular Cloning: A Laboratory Manual. Third Edition (Cold Spring Harbor, NY: Cold Spring Harbor Press (2000).
Santoro et al., A high-throughput platform for screening milligram quantities of plant biomass for lignocellulose digestibility, *Bioenergy Research* (2010) 3(1), 93-102.
Sawasaki et al., "Construction of an efficient expression vector for coupled transcription/translation in a wheat germ cell-free system." *Nucleic acids Symposium Series.* (2000) vol. 44. No. 1. Oxford University Press.
Seca et al., Phenolic constituents from the core of kenaf (*Hibiscus cannabinus*), *Phytochemistry* (2001) 56.7:759-767.
Sengupta-Gopalan, C., Developmentally regulated expression of the bean β-phaseolin gene in tobacco seed, *Proc. Natl. Acad. Sci. USA.* (1985) 83:3320-3324.
Shuai et al., Formaldehyde stabilization facilitates lignin monomer production during biomass depolymerization, *Science* (2016) 354(6310), 329-333.
Sibout et al., Structural redesigning *Arabidopsis* lignins into alkali-soluble lignins through the expression of p-coumaroyl-CoA:monolignol transferase PMT. *Plant Physiol.* (2016) 170 (3), 1358-66.
Sharp, RNAi and double-strand RNA, (1999) Genes Dev. 13:139-141.
Sharp and Zamore, Molecular biology. RNA interference, (2000) Science 287:2431-2433.
Smith, D.C.C. (1955a) Ester groups in lignin. Nature 176:267-268.
Smith, D.C.C. (1955b) p-Hydroxybenzoates groups in the lignin of Aspen (Populus tremula) Journal of the Chemical Society 2347).
Sievers et al, Fast, scalable generation of high-quality protein multiple sequence alignments using Clustal Omega. *Mol Syst Biol.* (2011) 7:539.
Smith and Waterman, Comparison of Biosequences, (1981) *Adv. Appl. Math* 2:482.
Smith et al., The challenges of genome sequence annotation or "The devil is in the details", *Nature Biotechnology* (1997) 15:1222-1223.
Smith et al., Engineering monolignol p-coumarate conjugates into poplar and *Arabidopsis* lignins, *Plant Physiology* (2015) 169, 2992-3001.
Smith et al., Defining the diverse cell populations contributing to lignification in *Arabidopsis thaliana* 13 stems, *Plant Physiology* (2017) 174, 1028-1036.
Stalker et al., Herbicide resistance in transgenic plants expressing a bacterial detoxification gene, *Science* (1988) 242:419-423.
Stewart et al., The effects on lignin structure of overexpression of ferulate 5-hydroxylase in hybrid poplar, *Plant Physiol.* (2009) 150(2), 621-635.
Stiefel et al., Expression of a maize cell wall hydroxyproline-rich glycoprotein gene in early leaf and root vascular differentiation, *The Plant Cell.* (1990) 2:785-793.
Sullivan et al., Isolation and characterization of a maize chlorophyll a/b binding protein gene that produces high levels of mRNA in the dark, *Mol. Gen. Genet.* (1989) 215:431.

(56) References Cited

OTHER PUBLICATIONS

Sutcliffe, J. G., Complete nucleotide sequence of the *Escherichia coli* plasmid pBR322, *Proc. Natl. Acad. Sci. USA*. (1978) 75:3737-3741.
Tabara et al. The rde-1 gene, RNA interference, and transposon silencing in C. elegans (1999) Cell 99:123-132.
Thillet et al., Site-directed mutagenesis of mouse dihydrofolate reductase. Mutants with increased resistance to methotrexate and trimethoprim, *J. Biol. Chem.* (1988) 263:12500-12508.
Thornton et al., From structure to function: Approaches and limitations, *Nature structural Biology, structural genomics supplement*, (Nov. 2000).
Tijssen, Laboratory Techniques in Biochemistry and Molecular Biology—Hybridization With Nucleic Acid Probes, part 1, chapter 2, "Overview of principles of hybridization and the strategy of nucleic acid probe assays," Elsevier, N.Y. (1993).
Tuominen et al., Differential phylogenetic expansions in BAHD acyltransferases across five angiosperm taxa and evidence of divergent expression among *Polulus* paralogues, *BMC Genomics*, (2011) 12-236.
Twell et al., Transient Expression of Chimeric Genes Delivered into Pollen by Microprojectile Bombardment, *Plant Physiol.* (1989) 91:1270 1274.
UNIPROTKB—A0A2K2CDA7 (A0A2K2CDA7_POPTR), Mar. 28, 2018 [online]. [Retrieved on Jan. 24, 2020]. Retrieved from the internet ,https://www.uniprot.org/uniprot/A0A2K2CDA7>.
Upton et al., Strategies for the conversion of lignin to high-value polymeric materials: Review and perspective, *Chemical Reviews* (2016) 116(4), 2275-2306.
Vanholme et al., Lignin engineering, *Curr. Opin. Plant Biol.* (2008) 11(3), 278-285.
Vanholme et al., Lignin biosynthesis and structure, *Plant Physiol.* (2010) 153(3), 895-905.
Vanholme et al., Metabolic engineering of novel lignin in biomass crops, *New Phytol.* (2012) 196(4), 978-1000.
Walker et al., DNA sequences required for anaerobic expression of the maize alcohol dehydrogenase 1 gene, *Proc. Natl. Acad. Sci. USA*. (1987) 84:6624-6628.
Wang et al., Characterization of cis-acting elements regulating transcription from the promoter of a constitutively active rice actin gene, *Mol. Cell. Biol.* (1992) 12:3399.
Ware NCBI, GenBank Sequence Accession No. AQK78565.1; Published (Feb. 7, 2017).
Wells, Additivity of Mutational Effects in Proteins, Biochemistry (1990) 29:8509-8517.
Wilkerson et al., (GenBank Sequence Accession No. AHL24755; pp. 1-2; 2014).
Wilkerson et al., Monolignol ferulate transferase introduces chemically labile linkages into the lignin backbone, *Science* (2014) 344:91.
Wishart et al., A single Mutation Converts a Novel Phosphotyrosine Binding Domain into a Dual-specificity Phosphatase, *JBC*, (1995) 270:26782-26785.
Withers et al., Identification of a grass-specific enzyme that acylates monolignols with *p*-coumarate, *Journal of Biological Chemistry* (2012) 287, 8347-8355.
Wooten and Federhen, Statistics of Local Complexity in Amino Acid Sequences and Sequence Databases, *Comput. Chem.* (1993) 17:149-63.
Yang et al., Maize sucrose synthase-1 promoter directs phloem cell-specific expression of Gus gene in transgenic tobacco plants, *Proc. Natl. Acad. Sci. USA*. (1990) 87:4144-4148.
Yang et al., Expression of the REB transcriptional activator in rice grains improves the yield of recombinant proteins whose genes are controlled by a *Reb*-responsive promoter, *PNAS*, (2001) 98:11438-11443.
Yelle et al., Characterization of non-derivatized plant cell walls using high-resolution solution-state NMR spectroscopy, *Magn. Reson. Chem.* (2008) 46(6), 508-517.
Zukowski et al., Chromogenic identification of genetic regulatory signals in *Bacillus subtilis* based on expression of a cloned *Pseudomonas* gene, *Proc. Natl. Acad. Sci. USA*. (1983) 80:1101.
Hanzawa, et al. "A single amino acid converts a repressor to an activator of flowering," PNAS, 102, 2005, 7748-7753.
Paterson et al. NCBI, GenBank Sequence Accession No. XP_002441966.1, Published Jul. 13, 2009.

\* cited by examiner monolignols
(ML)

*p*-coumaroyl-CoA
(*p*CA-CoA)

feruloyl-CoA
(FA-CoA)

monolignol *p*-coumarate
(ML-*p*CA)

monolignol ferulate
(ML-FA)

```
CLUSTAL O(1.2.4) multiple sequence alignment

XMT1      ------------MATPTSLSFAVRRCEPELVAPAKATPHEFRQLSDIDRQLYLQFQSPHY  48
XMT2      ------------MATPTSISFAVRRCEPELVAPAKATPHEFRQLSDIDRQLYLQFQSPHY  48
XMT3      ------------MATPPSLSFAVRRCEPELIAPAKATPHEFRQLSDIDRQLYLQFQSPHY  48
XMT4      ------------MATPTSISFAVRRCEPELVAPAKATPHEFRQLSDIDRQLYLQFSPGY   48
XMT5      ------------MAASTPLSFAVRRCEPELVAPAKATPHELRQLSDIDRQLYLQFQSPNY  48
XMT6      ------------MPTPTSLAFNVRRCEPELVAPAKATPHESKPLSDIDRQLYLQFQSPHY  48
XMT7      -----------MADGSNDALKLTVKQGEPTLVPPAEETKKGLYFLSNLDQNIAVIVR-TIY 49
XMT8      MGIEAEKFSAMEYSNGNVFQLVVKQGEPTLVPPAEETEKGLYFLSNLDQNIAVIVR-TIY  59
XMT9      -----------MEGTGKHGGDQLSVKKSEPVLIEPETRTHSGFFFLCNLDHMVTHSVE-TVY 50
                     : *:: ** *: *    *       *.::*:  :   ..    *

XMT1      NLYAHNPSMQGKDPVKVIKEAIAQALVYYYPFAGRIRQGPDNKLIVDCTGEGVLFIEADA 108
XMT2      NLYAHNPSMQGKDPVKVIKEAIAQALVYYYPFAGRIRQGPDNKLIVDCTGEGVLFIEADA 108
XMT3      NLYAHNPSMQGKDPVKVIKEAIAQALVYYYPFAGRIRQGPDNKLIVDCTGEGVLFIEADA 108
XMT4      NLYAHNPSMQGKDPVKVIKEAIAQALVYYYPFAGRIRQGPDNKLIVDCTGEGVLFIEADA 108
XMT5      NLYAHNPSMQGKDPVKVIKEAIAQTLVYYYPFAGRIRQGPDNKLIVECTGEGVLFIEADA 108
XMT6      NFYAHNPSMQGKDPVKVIREGIAQALVYYYPYAGRIRQEPENKLVVDCTGEGVLFIEADA 108
XMT7      CFKSDVKGNE---DAVEVIKNALSKILVHYYPIAGRLTISSKGKLIVDCTGEGAVFVEAET 107
XMT8      CFKSEEKGNE---NAGEVIKNALKKVLVHYYPLAGRLTISSEAKLIINCTGEGAVFVEAEA 117
XMT9      FYKAKKWGGSRDTLSDTFKQSLAKILVHYYPLAGRLRLGSDGKYNVECTNEGVLFVEARA 110
            :.   ..    ..::.: :  **:*** ***:    .*    ::**.**.:*:** :

XMT1      DATVEQFG---DPIPSPFPCFQELLYNVPGSEGILNTPLLIFQVTRLKCGGFVLGLRLNHP 166
XMT2      DATVEQFG---DPIPSPFPCFQELLYNVPGSEGILNTPLLIFQVTRLKCGGFVLGFRLNHP 166
XMT3      DATVEQFG---DPIPSPFPCFQELLYNVPGSEGILNTPLLLFQVTRLKCGGFVLGFRLNHP 166
XMT4      DATVEQFG---DPIPSPFPCFQELLYNVPGSEEILNTPLLLFQVTRLKCGGFVLGLRFNHL 166
XMT5      DATVEQFG---DPIPSPFPCFEELLYNVPGSAGIHNTPLLSFQVTRLKCGGFVLAYRLNHL 166
XMT6      DGTLEQFG---DPIQPPFPCAEELLYNVPGSAGIINTPLLIIQITRLKCGGFILGFRLNHP 166
XMT7      DCEIAELG---DITKPDPVTLGKLVYEIPGAQNILQMPPVTAQVTKFKCGGFVLGLCTNHC 165
XMT8      NCALEEIG---DITKPDPDTLGKLVYDIPGAKNILEMPPLVAQVTKFTCGGFALGLCMNHC 175
XMT9      NCNMDQVDVKVIIDDHSETAGKLVYGSPDPENILENPLMTAQVTRFRCGGFALGLSISHL 170
            : : :..          :*.:*  *.  *   * :*:: **** *.    .*

XMT1      MTDAFGMLQVLNAIGEIARGAQAPSILPVWRRELLCARNPPRVTCRHNEYGNDAPVAVDP 226
XMT2      MTDALGIVQLLNAIGEIARGAQAPSILPVWQRELLCARNPPRVTCRHNEYGNDAPVAVDP 226
XMT3      MTDALGIVQLLNAIGEIARGAQAPSILPVWQRELLCARNPPRVTCRHNEYGNDAPVAVDP 226
XMT4      MSDGLGMLQLFNTIGEMARGAQTPSILPVWQRELLCARNPPRVTCRHNEYGDDAPVAVDP 226
XMT5      MSDALGIVQLLSAIGEIARGAQAPSILPVWQRELLCARNPPRVTRRHSEYGNDGPVVVGP 226
XMT6      MSDAIGLVQLLSAIGEISRGAQAPSILPVWQRELLCARNPPRVTCTHNEYGDHHDLVVDP 226
XMT7      MFDGIGAMEFVNSWGATARGLA-LDVPPFLDRSILKARIPPKIEFPHHEFDDIED--VSN 222
XMT8      MFDGIGAMEFVNSWGETARGLP-LCVPPFIDRSILKARNPPKIEYPHQEFAEIKD--KSS 232
XMT9      IADGLSAMEFIKSWSETARGMP-LTTKPVLDRSILRSRQPPKIDFHFDQYAPAETSNVSN 229
           : *.:. ::..,.: . :**         *.  *.:* :* **::  .  .::    .
```

FIG. 3A

```
XMT1  T-AKVPEFHGQVHAVAHRSFVLNRKELSNIR--RWIPSHLHPCSNFEVITACLWRCYAIA 283
XMT2  T-AKVPEFHGQVHAVAHRSFVLNRKELSNIR--RWIPSHLHPCSNFEVISACLWRCYAMA 283
XMT3  T-AKVPEFHGQVHAVAHRSFVLNRKELSNIR--RWIPSHLHPCSNFEVISACLWRCYAMA 283
XMT4  T-AKVPEFRGEVHAVAHRSFVLNRKELSNIR--RWVPSHLHPCSDFEVISACLWRCYAIA 283
XMT5  T-TNVPEFHGEVYDVAHRSFVLNRKELSNIR--RWIPSHLHPCSNFEVISACLWRCYAIA 283
XMT6  SELNVPEFRGSTDGAAHRCFIIGPKELSNIR--KWIPPHLHPCSKFEIITACLWRCHAIA 284
XMT7  T-S---KLYE--EEMLYRSFCFDPEKLDQLKEKAMEDGVIAKCTTFQVLSAFVWRARCQA 276
XMT8  T-N---DLYK--DEMLYSSFCFDSEMLEKIKMKAMEDGVLGKCTTFEGLSAFVWRARTKA 286
XMT9  ISN---PFQG--EQILTKCFLFDSNKLAILKSMAMEDGTIKSCSNFTALTAFVWRARCKA 284
         :         ,* :. : *  ::      :  *: *  ::* :**.    *

XMT1  SQANPNEEMRMQMLVNARSKFNPPLPKGYYGNVLALPAAVTNARKLCLNSLGYALEMIRN 343
XMT2  SQANPNEEMRMQMLVNARSKFNPPLPKGYYGNVLALPAAVTNARKLCLNSLGYAVEMIRN 343
XMT3  SQANPNEEMRMQMLVNARSKFNPPLPKGYYGNVLALPAAVTNARKLCLNSLGYAVEMIRN 343
XMT4  SQANPNEEMRMQMLVNARSKFNPPLPKGYYGNVLALPAAVTNARKLCLNSLGYALEMIRN 343
XMT5  SQANPNEQMRMQLLVNARSKFNPPLPKGYYGNVLALPAAVTNAKNLCLNSLGYAMELIRN 343
XMT6  SQANPNEEMRICMLVNARSKFNPPLPKGYYGNVLALPAAITSARKLCLNSLGYALELIRQ 344
XMT7  LKMVPDQQIKLLFAADGRSRFEPPIPEGYFGNAIVLTNSLCTAGEIMENQLSFAVRLVQE 336
XMT8  LKMLPDQQTKLLFAVDGRPKFKPPLPKGYFGNGIVLTNSMCQAGELLDRPLSHAVGLVQD 346
XMT9  LQMNPDQTTPLLLVVDVRSKLNPPLPKGYFGNGIVLITCPGRAGELIKNTLSFAVEEVQN 344
       : *::   : : .: * :::***:*:**:**  :.*  .   * ::  . *..*:  :::

XMT1  AKNRITEEYMRSLADLMEITKGQPIGLQSYV-VSDLTGFGFDQVDYGWGNTIYTGPPKAM 402
XMT2  AKNRITEEYMRSLADLMEITKGQPIGLQSYV-VSDLTSIGFDQVDYGWGNTIYTGPPKAM 402
XMT3  AKNRITEEYMRSLADLMEITKGQPIGLQSYV-VSDLTSIGFDQVDYGWGNTIYTGPPKAM 402
XMT4  AKNRITEEYMRSLADLMEITKGQPIALQSYV-VSDLTSFGFDQVDYGWGNTIYSGPPKAM 402
XMT5  AKNAITEEYMRSLADLIEITKGQPIGLQSYV-VSDITSIGFDQVDCGWDKPVYAGPAKAM 402
XMT6  AKNKITEEYIRSLADFIEITKGLPKGLQSYV-VSDLTSVGFDQVDYGWGKPVYTGPSKAM 403
XMT7  AVKMVDDSYMRSAIDYFEVTRARP-SLTATLLITTWSRLSFHTTDFGWGVPILSGPVALP 395
XMT8  AIKMVTDSYMRSAMDYFEATRVRP-SLASTLLITTWSRLSFYTTDFGWGEPVLSGPVALP 405
XMT9  GIKMVNEEFVRSWIDYLEVMGAKDFPLHSYFKVSSWTRLSIECSDFGWGEPAQFACTNLP 404
       . : :  :.::**  *  :*         *  :  ::    *.. *  * **.    .

XMT1  PDEISMAGTYFLPYRFKNGERGVMLLVSLRAPVMERFAILLEELARHDPERSQEQQEMIP 462
XMT2  PDEISIAGTYFLPYRFKNGERGVMLLVSLRAPVMERFAILLEELARHDPERSQEQQEMIP 462
XMT3  PDEISIAGTYFLPYRFKNGERGVMLLVSLRAPVMERFAILLEELARHDPERSQEQQEMIP 462
XMT4  PDEISIAGTFVLPYRFKNGERGVMVLVSLRAPVMERFAILLEELARHDPERSQGQQEMIP 462
XMT5  PDEISIAGTYFLPYRFKNGERGVMLLVSLRAPVMERFAVLLEELARNDPERSQGQQEMIL 462
XMT6  PDDINNSGTYYLPYRNKKGERGVMVLISLRAPVMARFAMLFEELTKHDPDSPAQHHTTL 463
XMT7  EKEV----ILFLSH--GIERKNINVLVGLPASSMKIFEELMQI----------------- 432
XMT8  EKEV----ILFLSH--GKERKSINVLLGLPALAMKTFQEMIQI----------------- 442
XMT9  KN-S----AFFLPD--GKEKKGINLILDLPVTAMSTFQELMLL----------------- 440
         .       *     .:.: :::.* . * *  ::
```

FIG. 3B

```
XMT1   SSL---- 465   (SEQ ID NO:2)
XMT2   SSL---- 465   (SEQ ID NO:4)
XMT3   SSL---- 465   (SEQ ID NO:6)
XMT4   SSL---- 465   (SEQ ID NO:8)
XMT5   SSL---- 465   (SEQ ID NO:10)
XMT6   PIRHRL* 469   (SEQ ID NO:12)
XMT7   ------- 432   (SEQ ID NO:14)
XMT8   ------- 442   (SEQ ID NO:16)
XMT9   ------- 440   (SEQ ID NO:18)
```

FIG. 3C

CLUSTAL O(1.2.4) multiple sequence alignment

```
XMT1    MATPTSLSFAVRRCEPELVAPAKATPHEFRQLSDIDRQLYLQFQSPHYNLYAHNPSMQGK  60
XMT2    MATPTSISFAVRRCEPELVAPAKATPHEFRQLSDIDRQLYLQFQSPHYNLYAHNPSMQGK  60
XMT3    MATPPSLSFAVRRCEPELIAPAKATPHEFRQLSDIDRQLYLQFQSPHYNLYAHNPSMQGK  60
XMT4    MATPTSISFAVRRCEPELVAPAKATPHEFRQLSDIDRQLYLQFQSPGYNLYAHNPSMQGK  60
XMT5    MAASTPLSFAVRRCEPELVAPAKATPHELRQLSDIDRQLYLQFQSPNYNLYAHNPSMQGK  60
XMT6    MPTPTSLAFNVRRCEPELVAPAKATPHESKPLSDIDRQLYLQFQSPHYNFYAHNPSMQGK  60
        * :   ::* *******:******* : ***************  **:***********

XMT1    DPVKVIKEAIAQALVYYYPFAGRIRQGPDNKLIVDCTGEGVLFIEADADATVEQFGDPIP 120
XMT2    DPVKVIKEAIAQALVYYYPFAGRIRQGPDNKLIVDCTGEGVLFIEADADATVEQFGDPIP 120
XMT3    DPVKVIKEAIAQALVYYYPFAGRIRQGPDNKLIVDCTGEGVLFIEADADATVEQFGDPIP 120
XMT4    DPVKVIKEAIAQALVYYYPFAGRIRQGPDNKLIVDCTGEGVLFIEADADATVEQFGDPIP 120
XMT5    DPVKVIKEAIAQTLVYYYPFAGRIRQGPDNKLIVECTGEGVLFIEADADATVEQFGDPIP 120
XMT6    DPVKVIREGIAQALVYYYPYAGRIRQEPENKLVVDCTGEGVLFIEADADGTLEQFGDPIQ 120
        ******:*.***:****:****** *:***:*:**************.*:*******

XMT1    SPFPCFQELLYNVPGSEGILNTPLLIFQVTRLKCGGFVLGLRLNHPMTDAFGMLQVLNAI 180
XMT2    SPFPCFQELLYNVPGSEGILNTPLLIFQVTRLKCGGFVLGFRLNHPMTDALGIVQLLNAI 180
XMT3    SPFPCFQELLYNVPGSEGILNTPLLLFQVTRLKCGGFVLGFRLNHPMTDALGIVQLLNAI 180
XMT4    SPFPCFQELLYNVPGSEEILNTPLLLFQVTRLKCGGFVLGLRFNHLMSDGLGMLQLFNTI 180
XMT5    SPFPCFEELLYNVPGSAGIHNTPLLSFQVTRLKCGGFVLAYRLNHLMSDALGIVQLLSAI 180
XMT6    PPFPCAEELLYNVPGSAGIINTPLLIIQITRLKCGGFILGFRLNHPMSDAIGLVQLLSAI 180
         **** :********  *  *****  :*:********:*  *:** *:** *::.:*

XMT1    GEIARGAQAPSILPVWRRELLCARNPPRVTCRHNEYGNDAPVAVDPT-AKVPEFHGQVHA 239
XMT2    GEIARGAQAPSILPVWQRELLCARNPPRVTCRHNEYGNDAPVAVDPT-AKVPEFHGQVHA 239
XMT3    GEIARGAQAPSILPVWQRELLCARNPPRVTCRHNEYGNDAPVAVDPT-AKVPEFHGQVHA 239
XMT4    GEMARGAQTPSILPVWQRELLCARNPPRVTCRHNEYGDDAPVAVDPT-AKVPEFRGEVHA 239
XMT5    GEIARGAQAPSILPVWQRELLCARNPPRVTRRHSEYGNDGPVVVGPT-TNVPEFHGEVYD 239
XMT6    GEISRGAQAPSILPVWQRELLCARNPPRVTCTHNEYGDHHDLVVDPSELNVPEFRGSTDG 240
        **:.****:*************** *.***:..  :.*.*:  :****:*..

XMT1    VAHRSFVLNRKELSNIRRWIPSHLHPCSNFEVITACLWRCYAIASQANPNEEMRMQMLVN 299
XMT2    VAHRSFVLNRKELSNIRRWIPSHLHPCSNFEVISACLWRCYAMASQANPNEEMRMQMLVN 299
XMT3    VAHRSFVLNRKELSNIRRWIPSHLHPCSNFEVISACLWRCYAMASQANPNEEMRMQMLVN 299
XMT4    VAHRSFVLNRKELSNIRRWVPSHLHPCSDFEVISACLWRCYAIASQANPNEEMRMQMLVN 299
XMT5    VAHRSFVLNRKELSNIRRWIPSHLHPCSNFEVISACLWRCYAIASQANPNEQMRMQLLVN 299
XMT6    AAHRCFIIGPKELSNIRKWIPPHLHPCSKFEIITACLWRHAIASQANPNEEMRICMLVN 300
        .***.*::..  *******:** ****** :**.*:*******:*:*********:*.  :***
```

FIG. 4A

```
XMT1  ARSKFNPPLPKGYYGNVLALPAAVTNARKLCLNSLGYALEMIRNAKNRITEEYMRSLADL 359
XMT2  ARSKFNPPLPKGYYGNVLALPAAVTNARKLCLNSLGYAVEMIRNAKNRITEEYMRSLADL 359
XMT3  ARSKFNPPLPKGYYGNVLALPAAVTNARKLCLNSLGYAVEMIRNAKNRITEEYMRSLADL 359
XMT4  ARSKFNPPLPKGYYGNVLALPAAVTNARKLCLNSLGYALEMIRNAKNRITEEYMRSLADL 359
XMT5  ARSKFNPPLPKGYYGNVLALPAAVTNAKNLCLNSLGYAMELIRNAKNAITEEYMRSLADL 359
XMT6  ARSKFNPPLPKGYYGNVLALPAAITSARKLCLNSLGYALELIRQAKNKITEEYIRSLADF 360
      ********************:*.*:;*********;*;**;*** *****;*****;

XMT1  MEITKGQPIGLQSYVVSDLTGFGFDQVDYGWGNTIYTGPPKAMPDEISMAGTYFLPYRFK 419
XMT2  MEITKGQPIGLQSYVVSDLTSIGFDQVDYGWGNTIYTGPPKAMPDEISIAGTYFLPYRFK 419
XMT3  MEITKGQPIGLQSYVVSDLTSIGFDQVDYGWGNTIYTGPPKAMPDEISIAGTYFLPYRFK 419
XMT4  MEITKGQPIALQSYVVSDLTSFGFDQVDYGWGNTIYSGPPKAMPDEISIAGTFVLPYRFK 419
XMT5  IEITKGQPIGLQSYVVSDITSIGFDQVDCGWDKPVYAGPAKAMPDEISIAGTYFLPYRFK 419
XMT6  IEITKGLPKGLQSYVVSDLTSVGFDQVDYGWGKPVYTGPSKAMPDDINNSGTYYLPYRNK 420
      ;***** * .********:*..****** **.: ;*;** *****;*. ;**; **** *

XMT1  NGERGVMLLVSLRAPVMERFAILLEELARHDPERSQEQQEMI
XMT2  NGERGVMLLVSLRAPVMERFAILLEELARHDPERSQEQQEMI
XMT3  NGERGVMLLVSLRAPVMERFAILLEELARHDPERSQEQQEMI
XMT4  NGERGVMVLVSLRAPVMERFAILLEELARHDPERSQGQQEMI
XMT5  NGERGVMLLVSLRAPVMERFAVLLEELARNDPERSQGQQEMI
XMT6  KGERGVMVLISLRAPVMARFAMLFEELTKHDPDSGPAQHHTT
      ;******;*;******  ***;*;***;;;**;  . *;.

XMT1  PSSL---- 465 (SEQ ID NO:2)
XMT2  PSSL---- 465 (SEQ ID NO:4)
XMT3  PSSL---- 465 (SEQ ID NO:6)
XMT4  PSSL---- 465 (SEQ ID NO:8)
XMT5  LSSL---- 465 (SEQ ID NO:10)
XMT6  LPIRHRL- 469 (SEQ ID NO:12)
```

FIG. 4B

CLUSTAL O(1.2.4) multiple sequence alignment

```
XMT7   ----------MADGSNDALKLTVKQGEPTLVPPAEETKKGLYFLSNLDQNIAVIVRTIYC  50
XMT8   MGIEAEKFSAMEYSNGNVFQLVVKQGEPTLVPPAEETEKGLYFLSNLDQNIAVIVRTIYC  60
XMT9   ----------MEGTGKHGGDQLSVKKSEPVLIEPETRTHSGFFFLCNLDHMVTHSVETVYF  51
                 .. . :* **:.**.*: *  .*..*::**.***:  ::   *.*:*

XMT7   FKSDVKGNE--DAVEVIKNALSKILVHYYPIAGRLTISSKGKLIVDCTGEGAVFVEAETD 108
XMT8   FKSEEKGNE--NAGEVIKNALKKVLVHYYPLAGRLTISSEAKLIINCTGEGAVFVEAEAN 118
XMT9   YKAKKWGGSRDTLSDTFKQSLAKILVHYYPLAGRLRLGSDGKYNVECTNEGVLFVEARAN 111
        :*:.  *..       :.:*:* *:******:****  :.*..*   ::**.**.:****.::

XMT7   CEIAELG--DITKPDPVTLGKLVYEIPGAQNILQMPPVTAQVTKFKCGGFVLGLCTNHCM 166
XMT8   CALEEIG--DITKPDPDTLGKLVYDIPGAKNILEMPPLVAQVTKFTCGGFALGLCMNHCM 176
XMT9   CNMDQVDVKVIIDDHSETAGKLVYGSPDPENILENPLMTAQVTRFRCGGFALGLSISHLI 171
       *  : ::.    *  . * *****  *. :***: * :.****:* ****.***. .* :

XMT7   FDGIGAMEFVNSWGATARGLALDVPPFLDRSILKARIPPKIEFPHHEFDDIED---VSNT- 223
XMT8   FDGIGAMEFVNSWGETARGLPLCVPPFIDRSILKARNPPKIEYPHQEFAEIKD---KSST- 233
XMT9   ADGLSAMEFIKSWSETARGMPLTTKPVLDRSILRSRQPPKIDFHFDQYAPAETSNVSNIS 231
        **:.****::**. ****:  *  . *.:****::* **** ..:: : ..::    *.

XMT7   SKLYEEEMLYRSFCFDPEKLDQLKEKAMEDGVIAKCTTFQVLSAFVWRARCQALKMVPDQ 283
XMT8   NDLYKDEMLYSSFCFDSEMLEKIKMKAMEDGVLGKCTTFEGLSAFVWRARTKALKMLPDQ 293
XMT9   NPFQGEQILTKCFLFDSNKLAILKSMAMEDGTIKSCSNFTALTAFVWRARCKALQMNPDQ 291
        . :   ::::*  .*.** ** :  *  :* ****.: .*:.*  *:*******  :**:* ***

XMT7   QIKLLFAADGRSRFEPPIPEGYFGNAIVLTNSLCTAGEIMENQLSFAVRLVQEAVKMVDD 343
XMT8   QTKLLFAVDGRPKFKPPLPKGYFGNGIVLTNSMCQAGELLDRPLSHAVGLVQDAIKMVTD 353
XMT9   TTPLLLVVDVRSKLNPPLPKGYFGNGIVLITCPGRAGELIKNTLSFAVEEVQNGIKMVNE 351
          **:..* * :::**:*:***.***  ..    ***:.. **.**  *:..:*** :

XMT7   SYMRSAIDYFEVTRARP-SLTATLLITTWSRLSFHTTDFGWGVPILSGPVALPEKEVILF 402
XMT8   SYMRSAMDYFEATRVRP-SLASTLLITTWSRLSFYTTDFGWGEPVLSGPVALPEKEVILF 412
XMT9   EFVRSWIDYLEVMGAKDFPLHSYFKVSSWTRLSIECSDFGWGEPAQFACTNLPKN-SAFF 410
         .::** :**:*. .:  .:   *  :  :::*:***: :***** *   . . **::    :*

XMT7   LSHGIERKNINVLVGLPASSMKIFEELMQI 432 (SEQ ID NO:14)
XMT8   LSHGKERKSINVLLGLPALAMKTFQEMIQI 442 (SEQ ID NO:16)
XMT9   LPDGKEKKGINLILDLPVTAMSTFQELMLL 440 (SEQ ID NO:18)
       * .* *:*.**:::.**. :*. *:*:: :
```

FIG. 5

CLUSTAL O(1.2.4) multiple sequence alignment

XMT7    ----------MADGSNDALKLTVKQGEPTLVPPAEETKKGLYFLSNLDQNIAVIVRTIYC  50
XMT8    MGIEAEKFSAMEYSNGNVFQLVVKQGEPTLVPPAEETEKGLYFLSNLDQNIAVIVRTIYC  60
                 *   ...:.::*.*****************:********************

XMT7    FKSDVKGNEDAVEVIKNALSKILVHYYPIAGRLTISSKGKLIVDCTGEGAVFVEAETDCE  110
XMT8    FKSEEKGNENAGEVIKNALKKVLVHYYPLAGRLTISSEAKLIINCTGEGAVFVEAEANCA  120
        *:  **:.* *******:*::***:**..:*  :*************::*

XMT7    IAELGDITKPDPVTLGKLVYEIPGAQNILQMPPVTAQVTKFKCGGFVLGLCTNHCMFDGI  170
XMT8    LEEIGDITKPDPDTLGKLVYDIPGAKNILEMPPLVAQVTKFTCGGFALGLCMNHCMFDGI  180
        : *:****** ***::*:*:.**..*.******

XMT7    GAMEFVNSWGATARGLALDVPPFLDRSILKARIPPKIEFPHHEFDDIEDVSNTSKLYEEE  230
XMT8    GAMEFVNSWGETARGLPLCVPPFIDRSILKARNPPKIEYPHQEFAEIKDKSSTNDLYKDE  240
        ******** *** *  ***:**  *: ** :*: *.*..**::*

XMT7    MLYRSFCFDPEKLDQLKEKAMEDGVIAKCTTFQVLSAFVWRARCQALKMVPDQQIKLLFA  290
XMT8    MLYSSFCFDSEMLEKIKMKAMEDGVLGKCTTFEGLSAFVWRARTKALKMLPDQQTKLLFA  300
        * *** * *:::* **** *: *****  ::.***

XMT7    ADGRSRFEPPIPEGYFGNAIVLTNSLCTAGEIMENQLSFAVRLVQEAVKMVDDSYMRSAI  350
XMT8    VDGRPKFKPPLPKGYFGNGIVLTNSMCQAGELLDRPLSHAVGLVQDAIKMVTDSYMRSAM  360
        .***  :*:**:*:***.***:* *::.  . *.*:*.*****:

XMT7    DYFEVTRARPSLTATLLITTWSRLSFHTTDFGWGVPILSGPVALPEKEVILFLSHGIERK  410
XMT8    DYFEATRVRPSLASTLLITTWSRLSFYTTDFGWGEPVLSGPVALPEKEVILFLSHGKERK  420
        **. **::******:******.*:*********************  *

XMT7    NINVLVGLPASSMKIFEELMQI  432  (SEQ ID NO:14)
XMT8    SINVLLGLPALAMKTFQEMIQI  442  (SEQ ID NO:16)
        .**::..*:*::**

FIG. 6

| Enzyme | p-BMT | PMT | FMT | BMT |
|---|---|---|---|---|
| XMT1 | ✓ | ✓ | ✓ | ✓ |
| XMT6 | ✓ | | | |
| XMT3 | ✓ | | | ✓ |
| XMT2 | ✓ | | | ✓ |
| XMT9 | | | ✓ | |
| XMT7 | | ✓ | ✓ | |
| XMT8 | | ✓ | ✓ | |
| XMT4 | | ✓ | ✓ | ✓ |

SEQUENCE LISTING

<160> NUMBER OF SEQ ID NOS: 19

<210> SEQ ID NO 1
<211> LENGTH: 1398
<212> TYPE: DNA
<213> ORGANISM: Populus balsamifera subsp. trichocarpa

<400> SEQUENCE: 1

```
atggcaacac caacttcctt atcgttcgcc gtccgaaggt gcgaaccaga attggttgcg      60
ccagctaagg ccacacctca tgaattcaga cagctttctg atattgatcg ccaactatac     120
ctccaatttc aatcaccaca ttacaacttg tatgcacaca atccatcgat gcaagggaaa     180
gatcctgtga aggtaataaa ggaggcaatt gcgcaggcac ttgtgtatta ttacccttt      240 gctggtagga ttagacaagg gccagacaat aagcttatag ttgattgtac tggtgagggt     300
gtcttgttca tcgaagccga tgccgatgcc acggtggagc agtttggtga tccaattcca     360
```

```
tctccattcc catgctttca ggaacttctt tacaacgtcc caggatcaga agggatcctc      420 aatacccat tattgatttt tcaggtgaca cgcttgaagt gtggtggttt tgtacttggg       480
ctccgtctta atcacccaat gactgatgca ttcggcatgc ttcaggtatt gaatgccata      540
ggtgagattg cacgaggtgc tcaagcccct tcaattctac ctgtgtggcg aagggaactc     600
ctctgtgcta ggaatccgcc acgagttact gcagacaca atgaatatgg taatgatgct      660
cctgttgctt tgatcctac agccaaggtg cctgaattcc acggccaggt tcacgctgta     720
gcccaccgta gttttgttct caaccgcaag gaattatcca acattcgtag atggattcct     780
tctcatttac acccatgttc aaattttgag gtaataactg catgcttatg agatgctat      840 gccatagcat ctcaagctaa ccctaatgag gagatgcgca tgcaaatgct tgtcaacgca    900
cgttccaaat ttaaccctcc attaccgaaa ggatattatg gtaacgtgct agctttgcca    960
gcagctgtaa caaatgctag gaagctttgc ttaaactctt tagggtatgc attggaaatg    1020
ataagaaatg ccaagaatag aataactgag gagtacatga gatcattggc tgatctaatg    1080
gagataacca aagggcagcc tatagggtta caatcatatg tcgtgtcaga cttaacaggt    1140
tttgggttcg atcaggtgga ctatggatgg ggcaacacaa tttatactgg gccacccaag   1200
gctatgcctg atgaaatttc tatggcagga acctatttcc tgccgtatcg attcaagaac    1260
ggagagcgtg gggttatgct tttggtttcc ttacgtgcac cagttatgga gagatttgca    1320
atactattag aggaattggc aaggcatgac ccagaaagaa gccaagaaca acaagaaatg    1380
ataccaagct ccctataa                                                    1398

<210> SEQ ID NO 2
<211> LENGTH: 465
<212> TYPE: PRT
<213> ORGANISM: Populus balsamifera subsp. trichocarpa

<400> SEQUENCE: 2

Met Ala Thr Pro Thr Ser Leu Ser Phe Ala Val Arg Arg Cys Glu Pro
1               5                   10                  15

Glu Leu Val Ala Pro Ala Lys Ala Thr Pro His Glu Phe Arg Gln Leu
            20                  25                  30

Ser Asp Ile Asp Arg Gln Leu Tyr Leu Gln Phe Gln Ser Pro His Tyr
        35                  40                  45

Asn Leu Tyr Ala His Asn Pro Ser Met Gln Gly Lys Asp Pro Val Lys
    50                  55                  60

Val Ile Lys Glu Ala Ile Ala Gln Ala Leu Val Tyr Tyr Tyr Pro Phe
65                  70                  75                  80

Ala Gly Arg Ile Arg Gln Gly Pro Asp Asn Lys Leu Ile Val Asp Cys
                85                  90                  95

Thr Gly Glu Gly Val Leu Phe Ile Glu Ala Asp Ala Asp Ala Thr Val
            100                 105                 110

Glu Gln Phe Gly Asp Pro Ile Pro Ser Pro Phe Cys Phe Gln Glu
        115                 120                 125

Leu Leu Tyr Asn Val Pro Gly Ser Glu Gly Ile Leu Asn Thr Pro Leu
    130                 135                 140

Leu Ile Phe Gln Val Thr Arg Leu Lys Cys Gly Gly Phe Val Leu Gly
145                 150                 155                 160

Leu Arg Leu Asn His Pro Met Thr Asp Ala Phe Gly Met Leu Gln Val
                165                 170                 175

Leu Asn Ala Ile Gly Glu Ile Ala Arg Gly Ala Gln Ala Pro Ser Ile
```

```
                    180                 185                 190
Leu Pro Val Trp Arg Glu Leu Leu Cys Ala Arg Asn Pro Pro Arg
            195                 200                 205
Val Thr Cys Arg His Asn Glu Tyr Gly Asn Asp Ala Pro Val Ala Val
        210                 215                 220
Asp Pro Thr Ala Lys Val Pro Glu Phe His Gly Gln Val His Ala Val
225                 230                 235                 240
Ala His Arg Ser Phe Val Leu Asn Arg Lys Glu Leu Ser Asn Ile Arg
            245                 250                 255
Arg Trp Ile Pro Ser His Leu His Pro Cys Ser Asn Phe Glu Val Ile
        260                 265                 270
Thr Ala Cys Leu Trp Arg Cys Tyr Ala Ile Ala Ser Gln Ala Asn Pro
    275                 280                 285
Asn Glu Glu Met Arg Met Gln Met Leu Val Asn Ala Arg Ser Lys Phe
        290                 295                 300
Asn Pro Pro Leu Pro Lys Gly Tyr Tyr Gly Asn Val Leu Ala Leu Pro
305                 310                 315                 320
Ala Ala Val Thr Asn Ala Arg Lys Leu Cys Leu Asn Ser Leu Gly Tyr
                325                 330                 335
Ala Leu Glu Met Ile Arg Asn Ala Lys Asn Arg Ile Thr Glu Glu Tyr
            340                 345                 350
Met Arg Ser Leu Ala Asp Leu Met Glu Ile Thr Lys Gly Gln Pro Ile
        355                 360                 365
Gly Leu Gln Ser Tyr Val Val Ser Asp Leu Thr Gly Phe Gly Phe Asp
    370                 375                 380
Gln Val Asp Tyr Gly Trp Gly Asn Thr Ile Tyr Thr Gly Pro Pro Lys
385                 390                 395                 400
Ala Met Pro Asp Glu Ile Ser Met Ala Gly Thr Tyr Phe Leu Pro Tyr
                405                 410                 415
Arg Phe Lys Asn Gly Glu Arg Gly Val Met Leu Leu Val Ser Leu Arg
            420                 425                 430
Ala Pro Val Met Glu Arg Phe Ala Ile Leu Leu Glu Glu Leu Ala Arg
        435                 440                 445
His Asp Pro Glu Arg Ser Gln Glu Gln Gln Glu Met Ile Pro Ser Ser
    450                 455                 460
Leu
465

<210> SEQ ID NO 3
<211> LENGTH: 1398
<212> TYPE: DNA
<213> ORGANISM: Populus balsamifera subsp. trichocarpa

<400> SEQUENCE: 3
atggcaacac caacttccat atcgttcgcc gtccgaaggt gcgaaccaga attggttgcg      60
ccagctaagg ccacacctca tgaattcaga cagctttctg atattgatcg ccaactatac    120
ctccaatttc aataccacca ttacaacttg tatgcacaca tccatcgat gcaagggaaa     180 gatcctgtga aggtaataaa ggaggcaatt gcgcaggcac ttgtgtatta ttaccctttt    240
gctggtagga ttagacaagg ccagacaat aagcttatag ttgattgtac tggtgagggt     300
gtcttgttca tcgaagccga tgccgatgcc acggtggagc agtttggtga tccaattcca    360
tctccattcc catgctttca ggaacttctt tacaacgtcc caggatcaga agggatcctc    420 aatacccccat tattgatttt tcaggtgaca cgcttgaagt gtggcggttt tgtacttggg   480
```

-continued

```
ttccgtctta atcacccaat gaccgatgca ctcggcatag ttcagctatt gaatgccata    540
ggtgagattg cacgaggtgc ccaagcccct tcaattctac ctgtgtggca aagggaactc    600
ctctgtgcta ggaatccgcc acgagttaca tgcagacaca atgaatatgg taatgatgct    660
cctgttgctg ttgatcctac agccaaggtg cctgaattcc acggccaggt tcacgctgta    720
gcccaccgta gttttgttct caaccgcaag gaattatcca acattcgtag atggattcct    780
tctcatttac acccatgttc aaattttgag gtaataagtg catgcttatg agatgctat    840
gccatggcat ctcaagctaa ccctaatgag gagatgcgca tgcaaatgct tgttaacgca    900
cgttccaaat ttaaccctcc attaccgaaa ggatattatg gtaacgtgct agctttgcca    960
gcagctgtaa caaatgctag gaagctttgc ttaaactctt tagggtatgc tgtggaaatg   1020
ataagaaatg ccaagaatag aataactgag gagtacatga gatcattggc tgatctaatg   1080
gagataacca agggcagcc tatagggtta caatcatatg tcgtgtcaga cttaacaagt   1140
attgggttcg atcaggtgga ctatggatgg ggcaacacaa tttacactgg gccacccaag   1200
gccatgcctg atgaaatttc tattgcagga acctatttcc tgccgtatcg attcaagaac   1260
ggagagcgtg gggttatgct tttggtttcc ttacgtgcac cagttatgga gagatttgca   1320
atactattag aggaattggc aaggcatgac ccagaaagaa gccaagaaca acaagaaatg   1380
ataccaagct ccctataa                                                 1398
```

<210> SEQ ID NO 4
<211> LENGTH: 465
<212> TYPE: PRT
<213> ORGANISM: Populus balsamifera subsp. trichocarpa
<400> SEQUENCE: 4

```
Met Ala Thr Pro Thr Ser Ile Ser Phe Ala Val Arg Arg Cys Glu Pro
  1               5                  10                  15

Glu Leu Val Ala Pro Ala Lys Ala Thr Pro His Glu Phe Arg Gln Leu
             20                  25                  30

Ser Asp Ile Asp Arg Gln Leu Tyr Leu Gln Phe Gln Ser Pro His Tyr
         35                  40                  45

Asn Leu Tyr Ala His Asn Pro Ser Met Gln Gly Lys Asp Pro Val Lys
     50                  55                  60

Val Ile Lys Glu Ala Ile Ala Gln Ala Leu Val Tyr Tyr Tyr Pro Phe
 65                  70                  75                  80

Ala Gly Arg Ile Arg Gln Gly Pro Asp Asn Lys Leu Ile Val Asp Cys
                 85                  90                  95

Thr Gly Glu Gly Val Leu Phe Ile Glu Ala Asp Ala Asp Ala Thr Val
            100                 105                 110

Glu Gln Phe Gly Asp Pro Ile Pro Ser Pro Phe Pro Cys Phe Gln Glu
        115                 120                 125

Leu Leu Tyr Asn Val Pro Gly Ser Glu Gly Ile Leu Asn Thr Pro Leu
    130                 135                 140

Leu Ile Phe Gln Val Thr Arg Leu Lys Cys Gly Gly Phe Val Leu Gly
145                 150                 155                 160

Phe Arg Leu Asn His Pro Met Thr Asp Ala Leu Gly Ile Val Gln Leu
                165                 170                 175

Leu Asn Ala Ile Gly Glu Ile Ala Arg Gly Ala Gln Ala Pro Ser Ile
            180                 185                 190

Leu Pro Val Trp Gln Arg Glu Leu Leu Cys Ala Arg Asn Pro Pro Arg
        195                 200                 205
```

```
Val Thr Cys Arg His Asn Glu Tyr Gly Asn Asp Ala Pro Val Ala Val
    210                 215                 220

Asp Pro Thr Ala Lys Val Pro Glu Phe His Gly Gln Val His Ala Val
225                 230                 235                 240

Ala His Arg Ser Phe Val Leu Asn Arg Lys Glu Leu Ser Asn Ile Arg
                245                 250                 255

Arg Trp Ile Pro Ser His Leu His Pro Cys Ser Asn Phe Glu Val Ile
            260                 265                 270

Ser Ala Cys Leu Trp Arg Cys Tyr Ala Met Ala Ser Gln Ala Asn Pro
        275                 280                 285

Asn Glu Glu Met Arg Met Gln Met Leu Val Asn Ala Arg Ser Lys Phe
    290                 295                 300

Asn Pro Pro Leu Pro Lys Gly Tyr Tyr Gly Asn Val Leu Ala Leu Pro
305                 310                 315                 320

Ala Ala Val Thr Asn Ala Arg Lys Leu Cys Leu Asn Ser Leu Gly Tyr
                325                 330                 335

Ala Val Glu Met Ile Arg Asn Ala Lys Asn Arg Ile Thr Glu Glu Tyr
            340                 345                 350

Met Arg Ser Leu Ala Asp Leu Met Glu Ile Thr Lys Gly Gln Pro Ile
        355                 360                 365

Gly Leu Gln Ser Tyr Val Val Ser Asp Leu Thr Ser Ile Gly Phe Asp
    370                 375                 380

Gln Val Asp Tyr Gly Trp Gly Asn Thr Ile Tyr Thr Gly Pro Pro Lys
385                 390                 395                 400

Ala Met Pro Asp Glu Ile Ser Ile Ala Gly Thr Tyr Phe Leu Pro Tyr
                405                 410                 415

Arg Phe Lys Asn Gly Glu Arg Gly Val Met Leu Leu Val Ser Leu Arg
            420                 425                 430

Ala Pro Val Met Glu Arg Phe Ala Ile Leu Leu Glu Glu Leu Ala Arg
        435                 440                 445

His Asp Pro Glu Arg Ser Gln Glu Gln Gln Glu Met Ile Pro Ser Ser
    450                 455                 460

Leu
465

<210> SEQ ID NO 5
<211> LENGTH: 1398
<212> TYPE: DNA
<213> ORGANISM: Populus balsamifera subsp. trichocarpa

<400> SEQUENCE: 5
atggcaacac caccttcctt atcgttcgcc gtccgaaggt gcgaaccaga attgattgct      60
ccagctaagg ccacacctca tgaattcaga cagctttctg atattgatcg acaactatac     120
ctccaatttc aatcaccaca ttacaacttg tatgcacaca atccatcgat gcaagggaaa     180
gatcctgtga aggtaataaa ggaggcaatt gcgcaggcac ttgtgtatta ttaccctttt     240
gctggtagga ttagacaagg gccagacaat aagcttatag ttgattgtac tggtgagggt     300
gtcttgttca tcgaagccga tgccgatgcc acggtcgagc agtttggtga tccaattcca     360
tctccattcc catgttttca ggaacttctt tacaacgtcc aggatcaga agggatcctc     420 aataccccat tattgctttt tcaggtgaca cgcttgaagt gtggcggttt tgtacttggg     480
ttccgtctta atcacccaat gaccgatgca ctcggcatag ttcagctatt gaatgccata     540
ggtgagattg cacgaggtgc ccaagcccct tcaattctac ctgtgtggca aagggaactc     600
```

```
ctctgtgcta ggaatccgcc acgagttaca tgcagacaca atgaatatgg taatgatgct    660
cctgttgctg ttgatcctac agccaaggtg cctgaattcc acggccaggt tcacgctgta    720
gcccaccgta gttttgttct caaccgcaag gaattatcca acattcgtag atggattcct    780
tctcatttac acccatgttc aaattttgag gtaataagtg catgcttatg agatgctat    840
gccatggcat ctcaagctaa ccctaatgag gagatgcgca tgcaaatgct tgttaacgca    900
cgttccaaat ttaaccctcc attaccgaaa ggatattatg gtaacgtgct agctttgcca    960
gcagctgtaa caaatgctag gaagctttgc ttaaactctt tagggtatgc tgtggaaatg   1020
ataagaaatg ccaagaatag aataactgag gagtacatga gatcattggc tgatctaatg   1080
gagataacca agggcagcc tatagggtta caatcatatg tcgtgtcaga cttaacaagt   1140
attgggttcg atcaggtgga ctatggatgg ggcaacacaa tttacactgg gccacccaag   1200
gccatgcctg atgaaatttc tattgcagga acctatttcc tgccgtatcg attcaagaac   1260
ggagagcgtg gggttatgct tttggtttcc ttacgtgcac cagttatgga gagatttgca   1320
atactattag aggaattggc aaggcatgac ccagaaagaa gccaagaaca acaagaaatg   1380
ataccaagct ccctataa                                                  1398

<210> SEQ ID NO 6
<211> LENGTH: 465
<212> TYPE: PRT
<213> ORGANISM: Populus balsamifera subsp. trichocarpa

<400> SEQUENCE: 6

Met Ala Thr Pro Pro Ser Leu Ser Phe Ala Val Arg Arg Cys Glu Pro
1               5                   10                  15

Glu Leu Ile Ala Pro Ala Lys Ala Thr Pro His Glu Phe Arg Gln Leu
            20                  25                  30

Ser Asp Ile Asp Arg Gln Leu Tyr Leu Gln Phe Gln Ser Pro His Tyr
        35                  40                  45

Asn Leu Tyr Ala His Asn Pro Ser Met Gln Gly Lys Asp Pro Val Lys
    50                  55                  60

Val Ile Lys Glu Ala Ile Ala Gln Ala Leu Val Tyr Tyr Tyr Pro Phe
65                  70                  75                  80

Ala Gly Arg Ile Arg Gln Gly Pro Asp Asn Lys Leu Ile Val Asp Cys
                85                  90                  95

Thr Gly Glu Gly Val Leu Phe Ile Glu Ala Asp Ala Asp Ala Thr Val
            100                 105                 110

Glu Gln Phe Gly Asp Pro Ile Pro Ser Pro Phe Pro Cys Phe Gln Glu
        115                 120                 125

Leu Leu Tyr Asn Val Pro Gly Ser Glu Gly Ile Leu Asn Thr Pro Leu
    130                 135                 140

Leu Leu Phe Gln Val Thr Arg Leu Lys Cys Gly Gly Phe Val Leu Gly
145                 150                 155                 160

Phe Arg Leu Asn His Pro Met Thr Asp Ala Leu Gly Ile Val Gln Leu
                165                 170                 175

Leu Asn Ala Ile Gly Glu Ile Ala Arg Gly Ala Gln Ala Pro Ser Ile
            180                 185                 190

Leu Pro Val Trp Gln Arg Glu Leu Leu Cys Ala Arg Asn Pro Pro Arg
        195                 200                 205

Val Thr Cys Arg His Asn Glu Tyr Gly Asn Asp Ala Pro Val Ala Val
    210                 215                 220
```

```
Asp Pro Thr Ala Lys Val Pro Glu Phe His Gly Gln Val His Ala Val
225                 230                 235                 240

Ala His Arg Ser Phe Val Leu Asn Arg Lys Glu Leu Ser Asn Ile Arg
            245                 250                 255

Arg Trp Ile Pro Ser His Leu His Pro Cys Ser Asn Phe Glu Val Ile
        260                 265                 270

Ser Ala Cys Leu Trp Arg Cys Tyr Ala Met Ala Ser Gln Ala Asn Pro
    275                 280                 285

Asn Glu Glu Met Arg Met Gln Met Leu Val Asn Ala Arg Ser Lys Phe
290                 295                 300

Asn Pro Pro Leu Pro Lys Gly Tyr Tyr Gly Asn Val Leu Ala Leu Pro
305                 310                 315                 320

Ala Ala Val Thr Asn Ala Arg Lys Leu Cys Leu Asn Ser Leu Gly Tyr
            325                 330                 335

Ala Val Glu Met Ile Arg Asn Ala Lys Asn Arg Ile Thr Glu Glu Tyr
        340                 345                 350

Met Arg Ser Leu Ala Asp Leu Met Glu Ile Thr Lys Gly Gln Pro Ile
    355                 360                 365

Gly Leu Gln Ser Tyr Val Val Ser Asp Leu Thr Ser Ile Gly Phe Asp
370                 375                 380

Gln Val Asp Tyr Gly Trp Gly Asn Thr Ile Tyr Thr Gly Pro Pro Lys
385                 390                 395                 400

Ala Met Pro Asp Glu Ile Ser Ile Ala Gly Thr Tyr Phe Leu Pro Tyr
            405                 410                 415

Arg Phe Lys Asn Gly Glu Arg Gly Val Met Leu Leu Val Ser Leu Arg
        420                 425                 430

Ala Pro Val Met Glu Arg Phe Ala Ile Leu Leu Glu Glu Leu Ala Arg
    435                 440                 445

His Asp Pro Glu Arg Ser Gln Glu Gln Gln Glu Met Ile Pro Ser Ser
450                 455                 460

Leu
465

<210> SEQ ID NO 7
<211> LENGTH: 1398
<212> TYPE: DNA
<213> ORGANISM: Populus balsamifera subsp. trichocarpa

<400> SEQUENCE: 7
atggcaacac caacttcgat atcgttcgca gtccgaaggt gcgaaccaga attggtcgca     60
ccagctaagg ccacacctca tgaattcaga cagctttctg atattgatcg ccaactatac    120
ctccaatttc aataccaggt tacaacttg tatgcacaca atccatcgat gcaagggaaa     180
gatcctgtga aggtaataaa ggaggcaatt gcgcaggcac ttgtgtatta ttaccctttt    240
gctggtagga ttagacaagg ccagacaat aagcttatag ttgattgtac tggtgagggt     300
gtcttgttca tcgaagctga tgccgatgcc acggtcgagc agtttggtga tccaattcca    360
tctccattcc catgctttca ggaacttctt tacaacgtcc aggatcaga agagatcctc     420 aataccccat tattgctttt tcaggtgaca cgcttgaagt gtggtggttt tgtacttggg    480
ctccgtttta atcacctaat gagtgatgga ctcggcatgc ttcagttatt taataccata    540
ggtgagatgg cacgaggtgc tcaaacccct tcaattctac ctgtgtggca aagggaactc    600
ctctgtgcta ggaatccgcc acgagttaca tgcagacaca tgaatatgg tgatgatgct     660 cctgttgctg ttgatcctac agccaaggtg cctgaattcc gcggcgaggt tcacgctgta    720
```

```
gcccaccgta gttttgttct taaccgcaag gaattatcca acattcgtag atgggttcct      780
tctcatttac acccatgttc agattttgag gtaataagtg catgcttatg gagatgctat      840
gccatagcat ctcaagctaa ccctaatgag gagatgcgca tgcaaatgct tgtcaacgca      900
cgttccaaat ttaccctcc attaccgaaa ggatattatg gtaacgtgct agctttgcca       960
gcagctgtaa caaatgctag gaagctttgc ttaaactctt tagggtatgc attggaaatg     1020
ataagaaatg ccaagaatag aataactgag gagtacatga gatcattggc tgatctgatg     1080
gagataacca aagggcagcc tatagcgtta caatcatatg tcgtgtcaga cttaacaagt     1140
tttgggttcg atcaggtgga ctatggatgg ggcaacacaa tttactctgg gccacctaag     1200
gctatgccgg atgaaatttc tattgcagga acctttgtcc tgccgtatcg attcaagaac     1260
ggagagcgtg gggttatggt tttggtttcc ttacgtgcac cagttatgga gagatttgca     1320
atactattag aggaattggc aaggcatgac ccagaaagaa gccaaggaca caagaaatg     1380 ataccaagct ccctataa                                                    1398
```

<210> SEQ ID NO 8
<211> LENGTH: 465
<212> TYPE: PRT
<213> ORGANISM: Populus balsamifera subsp. trichocarpa

<400> SEQUENCE: 8

```
Met Ala Thr Pro Thr Ser Ile Ser Phe Ala Val Arg Arg Cys Glu Pro
1               5                  10                  15

Glu Leu Val Ala Pro Ala Lys Ala Thr Pro His Glu Phe Arg Gln Leu
            20                  25                  30

Ser Asp Ile Asp Arg Gln Leu Tyr Leu Gln Phe Gln Ser Pro Gly Tyr
        35                  40                  45

Asn Leu Tyr Ala His Asn Pro Ser Met Gln Gly Lys Asp Pro Val Lys
    50                  55                  60

Val Ile Lys Glu Ala Ile Ala Gln Ala Leu Val Tyr Tyr Tyr Pro Phe
65                  70                  75                  80

Ala Gly Arg Ile Arg Gln Gly Pro Asp Asn Lys Leu Ile Val Asp Cys
                85                  90                  95

Thr Gly Glu Gly Val Leu Phe Ile Glu Ala Asp Ala Asp Ala Thr Val
            100                 105                 110

Glu Gln Phe Gly Asp Pro Ile Pro Ser Pro Phe Pro Cys Phe Gln Glu
        115                 120                 125

Leu Leu Tyr Asn Val Pro Gly Ser Glu Glu Ile Leu Asn Thr Pro Leu
    130                 135                 140

Leu Leu Phe Gln Val Thr Arg Leu Lys Cys Gly Gly Phe Val Leu Gly
145                 150                 155                 160

Leu Arg Phe Asn His Leu Met Ser Asp Gly Leu Gly Met Leu Gln Leu
                165                 170                 175

Phe Asn Thr Ile Gly Glu Met Ala Arg Gly Ala Gln Thr Pro Ser Ile
            180                 185                 190

Leu Pro Val Trp Gln Arg Glu Leu Leu Cys Ala Arg Asn Pro Pro Arg
        195                 200                 205

Val Thr Cys Arg His Asn Glu Tyr Gly Asp Asp Ala Pro Val Ala Val
    210                 215                 220

Asp Pro Thr Ala Lys Val Pro Glu Phe Arg Gly Glu Val His Ala Val
225                 230                 235                 240

Ala His Arg Ser Phe Val Leu Asn Arg Lys Glu Leu Ser Asn Ile Arg
```

```
                    245                 250                 255
Arg Trp Val Pro Ser His Leu His Pro Cys Ser Asp Phe Glu Val Ile
            260                 265                 270
Ser Ala Cys Leu Trp Arg Cys Tyr Ala Ile Ala Ser Gln Ala Asn Pro
            275                 280                 285
Asn Glu Glu Met Arg Met Gln Met Leu Val Asn Ala Arg Ser Lys Phe
        290                 295                 300
Asn Pro Pro Leu Pro Lys Gly Tyr Tyr Gly Asn Val Leu Ala Leu Pro
305                 310                 315                 320
Ala Ala Val Thr Asn Ala Arg Lys Leu Cys Leu Asn Ser Leu Gly Tyr
                325                 330                 335
Ala Leu Glu Met Ile Arg Asn Ala Lys Asn Arg Ile Thr Glu Glu Tyr
            340                 345                 350
Met Arg Ser Leu Ala Asp Leu Met Glu Ile Thr Lys Gly Gln Pro Ile
        355                 360                 365
Ala Leu Gln Ser Tyr Val Val Ser Asp Leu Thr Ser Phe Gly Phe Asp
    370                 375                 380
Gln Val Asp Tyr Gly Trp Gly Asn Thr Ile Tyr Ser Gly Pro Pro Lys
385                 390                 395                 400
Ala Met Pro Asp Glu Ile Ser Ile Ala Gly Thr Phe Val Leu Pro Tyr
                405                 410                 415
Arg Phe Lys Asn Gly Glu Arg Gly Val Met Val Leu Val Ser Leu Arg
            420                 425                 430
Ala Pro Val Met Glu Arg Phe Ala Ile Leu Leu Glu Glu Leu Ala Arg
        435                 440                 445
His Asp Pro Glu Arg Ser Gln Gly Gln Gln Glu Met Ile Pro Ser Ser
    450                 455                 460
Leu
465

<210> SEQ ID NO 9
<211> LENGTH: 1398
<212> TYPE: DNA
<213> ORGANISM: Populus balsamifera subsp. trichocarpa

<400> SEQUENCE: 9
atggcagcat ctactccctt atcatttgcg gtccgacgat gcgaacctga attggttgcc      60
ccagctaaag ccactcctca tgaactcaga cagcttttctg atattgatcg ccaattatac    120
```

```
                    245                 250                 255
Arg Trp Val Pro Ser His Leu His Pro Cys Ser Asp Phe Glu Val Ile
            260                 265                 270
Ser Ala Cys Leu Trp Arg Cys Tyr Ala Ile Ala Ser Gln Ala Asn Pro
            275                 280                 285
Asn Glu Glu Met Arg Met Gln Met Leu Val Asn Ala Arg Ser Lys Phe
        290                 295                 300
Asn Pro Pro Leu Pro Lys Gly Tyr Tyr Gly Asn Val Leu Ala Leu Pro
305                 310                 315                 320
Ala Ala Val Thr Asn Ala Arg Lys Leu Cys Leu Asn Ser Leu Gly Tyr
                325                 330                 335
Ala Leu Glu Met Ile Arg Asn Ala Lys Asn Arg Ile Thr Glu Glu Tyr
            340                 345                 350
Met Arg Ser Leu Ala Asp Leu Met Glu Ile Thr Lys Gly Gln Pro Ile
        355                 360                 365
Ala Leu Gln Ser Tyr Val Val Ser Asp Leu Thr Ser Phe Gly Phe Asp
    370                 375                 380
Gln Val Asp Tyr Gly Trp Gly Asn Thr Ile Tyr Ser Gly Pro Pro Lys
385                 390                 395                 400
Ala Met Pro Asp Glu Ile Ser Ile Ala Gly Thr Phe Val Leu Pro Tyr
                405                 410                 415
Arg Phe Lys Asn Gly Glu Arg Gly Val Met Val Leu Val Ser Leu Arg
            420                 425                 430
Ala Pro Val Met Glu Arg Phe Ala Ile Leu Leu Glu Glu Leu Ala Arg
        435                 440                 445
His Asp Pro Glu Arg Ser Gln Gly Gln Gln Glu Met Ile Pro Ser Ser
    450                 455                 460
Leu
465

<210> SEQ ID NO 9
<211> LENGTH: 1398
<212> TYPE: DNA
<213> ORGANISM: Populus balsamifera subsp. trichocarpa

<400> SEQUENCE: 9
atggcagcat ctactccctt atcatttgcg gtccgacgat gcgaacctga attggttgcc      60
ccagctaaag ccactcctca tgaactcaga cagcttttctg atattgatcg ccaattatac    120
ctccaattcc aatcaccgaa ttacaacttg tatgcacaca tccctcaat gcaagggaaa      180
gatcccgtga aggtaataaa agaggcgatt gcacaaacac ttgtttatta ttacccttttt   240
gctggtagga ttagacaagg gccagacaat aagcttatag ttgaatgtac tggggagggt    300
gttttgttca tcgaagccga tgccgatgct acagttgagc agtttggtga tccaattcca    360
tctccattcc cttgctttga agaacttcta tacaacgtcc caggatctgc agggatccac    420
aataccccat tattgtcttt tcaggtgaca cgcttgaagt gtggtggttt tgtacttgcc    480
tatcgtctga atcacctaat gagtgatgct cttggcatag ttcagctatt gagtgccata    540
ggggagattg cacgaggtgc gcaagccct tcaattctac ctgtgtggca aagggaactt     600
ctctgtgcta ggaatccacc acgcgttact cgcagacaca gtgaatatgg taatgatggt    660
ccagttgttg ttggtcctac aaccaacgtt cctgaattcc acggcgaagt ttacgatgta    720
gcccaccgta gtttcgttct taaccgcaaa gaattatcaa acattcgtag atggattcct    780
tctcatttac accccttgttc aaattttgag gtcataagtg catgcttatg gagatgctat    840
```

```
gccatagcat ctcaagcaaa ccctaatgag cagatgcgca tgcaattgct tgtcaatgca    900
cgttccaagt tcaacccacc attaccaaaa ggatattacg gtaacgtgct agctttgcca    960
gcagctgtaa caaatgctaa gaacctttgt ttaaactcat tagggtatgc aatggagttg   1020
ataaggaatg ccaagaatgc aataactgag gagtacatga gatcattggc tgatctaata   1080
gagatcacca aaggccagcc tatcgggtta cagtcatatg ttgtgtcaga cataacaagt   1140
attgggtttg atcaagtgga ttgtgggtgg gataagccag tttatgctgg gccagctaag   1200
gccatgcctg atgaaatttc tattgctgga acctattttc tgccctatag attcaagaac   1260
ggagagcgag gggttatgct gttagttttcc ttacgcgcac cagttatgga gagatttgca   1320
gtcctcttag aggaattggc aaggaatgat ccagaaagaa gccaaggaca acaagaaatg   1380
atactaagct ccctttaa                                                 1398
```

<210> SEQ ID NO 10
<211> LENGTH: 465
<212> TYPE: PRT
<213> ORGANISM: Populus balsamifera subsp. trichocarpa

<400> SEQUENCE: 10

```
Met Ala Ala Ser Thr Pro Leu Ser Phe Ala Val Arg Arg Cys Glu Pro
1               5                   10                  15

Glu Leu Val Ala Pro Ala Lys Ala Thr Pro His Glu Leu Arg Gln Leu
            20                  25                  30

Ser Asp Ile Asp Arg Gln Leu Tyr Leu Gln Phe Gln Ser Pro Asn Tyr
        35                  40                  45

Asn Leu Tyr Ala His Asn Pro Ser Met Gln Gly Lys Asp Pro Val Lys
    50                  55                  60

Val Ile Lys Glu Ala Ile Ala Gln Thr Leu Val Tyr Tyr Tyr Pro Phe
65                  70                  75                  80

Ala Gly Arg Ile Arg Gln Gly Pro Asp Asn Lys Leu Ile Val Glu Cys
                85                  90                  95

Thr Gly Glu Gly Val Leu Phe Ile Glu Ala Asp Ala Asp Ala Thr Val
            100                 105                 110

Glu Gln Phe Gly Asp Pro Ile Pro Ser Pro Phe Pro Cys Phe Glu Glu
        115                 120                 125

Leu Leu Tyr Asn Val Pro Gly Ser Ala Gly Ile His Asn Thr Pro Leu
    130                 135                 140

Leu Ser Phe Gln Val Thr Arg Leu Lys Cys Gly Gly Phe Val Leu Ala
145                 150                 155                 160

Tyr Arg Leu Asn His Leu Met Ser Asp Ala Leu Gly Ile Val Gln Leu
                165                 170                 175

Leu Ser Ala Ile Gly Glu Ile Ala Arg Gly Ala Gln Ala Pro Ser Ile
            180                 185                 190

Leu Pro Val Trp Gln Arg Glu Leu Leu Cys Ala Arg Asn Pro Pro Arg
        195                 200                 205

Val Thr Arg Arg His Ser Glu Tyr Gly Asn Asp Gly Pro Val Val Val
    210                 215                 220

Gly Pro Thr Thr Asn Val Pro Glu Phe His Gly Glu Val Tyr Asp Val
225                 230                 235                 240

Ala His Arg Ser Phe Val Leu Asn Arg Lys Glu Leu Ser Asn Ile Arg
                245                 250                 255

Arg Trp Ile Pro Ser His Leu His Pro Cys Ser Asn Phe Glu Val Ile
            260                 265                 270
```

Ser Ala Cys Leu Trp Arg Cys Tyr Ala Ile Ala Ser Gln Ala Asn Pro
        275                 280                 285

Asn Glu Gln Met Arg Met Gln Leu Leu Val Asn Ala Arg Ser Lys Phe
    290                 295                 300

Asn Pro Pro Leu Pro Lys Gly Tyr Tyr Gly Asn Val Leu Ala Leu Pro
305                 310                 315                 320

Ala Ala Val Thr Asn Ala Lys Asn Leu Cys Leu Asn Ser Leu Gly Tyr
                325                 330                 335

Ala Met Glu Leu Ile Arg Asn Ala Lys Asn Ala Ile Thr Glu Glu Tyr
            340                 345                 350

Met Arg Ser Leu Ala Asp Leu Ile Glu Ile Thr Lys Gly Gln Pro Ile
        355                 360                 365

Gly Leu Gln Ser Tyr Val Val Ser Asp Ile Thr Ser Ile Gly Phe Asp
    370                 375                 380

Gln Val Asp Cys Gly Trp Asp Lys Pro Val Tyr Ala Gly Pro Ala Lys
385                 390                 395                 400

Ala Met Pro Asp Glu Ile Ser Ile Ala Gly Thr Tyr Phe Leu Pro Tyr
                405                 410                 415

Arg Phe Lys Asn Gly Glu Arg Gly Val Met Leu Leu Val Ser Leu Arg
            420                 425                 430

Ala Pro Val Met Glu Arg Phe Ala Val Leu Leu Glu Glu Leu Ala Arg
        435                 440                 445

Asn Asp Pro Glu Arg Ser Gln Gly Gln Gln Glu Met Ile Leu Ser Ser
    450                 455                 460

Leu
465

<210> SEQ ID NO 11
<211> LENGTH: 1410
<212> TYPE: DNA
<213> ORGANISM: Populus balsamifera subsp. trichocarpa

<400> SEQUENCE: 11
atgccaactc ctacttcctt agcattcaat gtgcgaaggt gcgagccaga attggttgca      60
ccagctaaag ccacacccca tgaatccaaa ccactttctg atatcgatcg ccaactatac     120
ctacaatttc aatcaccaca ttacaacttt tatgcacaca acccgtccat gcaagggaaa     180
gatcctgtga aggtaataag agagggaatt gctcaggcac ttgtgtatta ttatccttat     240
gccgggagga ttagacaaga gccagaaaat aagcttgtag tagattgtac aggagagggt     300
gtcttgttca ttgaagctga tgctgatggc acactggagc agtttggtga tccaattcag     360
cctccgttcc cttgtgctga ggaacttctt tacaatgtcc cagggtcagc aggaatcatc     420
aataccccgt gctgatcat tcagataaca cgcttgaagt gtggtggttt tatacttggc     480
ttccgtctta atcacccaat gagtgatgcc attggcctag ttcagctatt gagtgccata     540
ggtgagatct cacgaggtgc tcaagcccct tcaattctac ctgtgtggca aagagaactc     600
ctttgtgcta ggaatccacc tcgtgttact tgcacacaca acgaatatgg cgatcatcat     660
gatcttgttg tggatcctag cgagctcaac gttcctgaat tcggggtag cactgacggt     720 gcagcccacc gttgtttcat catcggccct aaagaattat ccaacattcg taatggatt      780 cctcctcatt tacacccatg ttccaagttt gaaataataa ccgcatgctt atggagatgc     840
catgccatag catctcaagc aaaccctaat gaggagatgc gcatttgtat gctcgtcaat     900
gcacgttcca aattcaaccc tccgttacca aagggttatt atggtaacgt gctggcattg     960

```
ccagcagcta taaccagtgc taggaagctt tgtttgaact cattagggta tgctctggag    1020
ctgataaggc aagccaagaa caagatcact gaggagtaca taagatcgtt ggccgatttc    1080
attgagatta ccaagggcct gcctaagggg ttacagtcat atgttgtgtc agatttaaca    1140
agtgttgggt tcgatcaggt ggattatggt tggggtaagc cagtttatac cgggccatct    1200
aaggctatgc ctgatgacat taataattct ggaacctatt acttaccccta tagaaacaag    1260 aaaggagagc gtggagtcat ggttctgatc tccttgcgtg caccagttat ggcaagattt    1320
gcaatgctat tcgaggagtt gaccaagcac gatccagata gtggtccagc acaacaccac    1380
actactctcc ctataagaca caggctttga                                     1410
```

<210> SEQ ID NO 12
<211> LENGTH: 469
<212> TYPE: PRT
<213> ORGANISM: Populus balsamifera subsp. trichocarpa

<400> SEQUENCE: 12

```
Met Pro Thr Pro Thr Ser Leu Ala Phe Asn Val Arg Arg Cys Glu Pro
1               5                   10                  15

Glu Leu Val Ala Pro Ala Lys Ala Thr Pro His Glu Ser Lys Pro Leu
            20                  25                  30

Ser Asp Ile Asp Arg Gln Leu Tyr Leu Gln Phe Gln Ser Pro His Tyr
        35                  40                  45

Asn Phe Tyr Ala His Asn Pro Ser Met Gln Gly Lys Asp Pro Val Lys
    50                  55                  60

Val Ile Arg Glu Gly Ile Ala Gln Ala Leu Val Tyr Tyr Tyr Pro Tyr
65                  70                  75                  80

Ala Gly Arg Ile Arg Gln Glu Pro Glu Asn Lys Leu Val Val Asp Cys
                85                  90                  95

Thr Gly Glu Gly Val Leu Phe Ile Glu Ala Asp Ala Asp Gly Thr Leu
            100                 105                 110

Glu Gln Phe Gly Asp Pro Ile Gln Pro Pro Phe Pro Cys Ala Glu Glu
        115                 120                 125

Leu Leu Tyr Asn Val Pro Gly Ser Ala Gly Ile Ile Asn Thr Pro Leu
    130                 135                 140

Leu Ile Ile Gln Ile Thr Arg Leu Lys Cys Gly Gly Phe Ile Leu Gly
145                 150                 155                 160

Phe Arg Leu Asn His Pro Met Ser Asp Ala Ile Gly Leu Val Gln Leu
                165                 170                 175

Leu Ser Ala Ile Gly Glu Ile Ser Arg Gly Ala Gln Ala Pro Ser Ile
            180                 185                 190

Leu Pro Val Trp Gln Arg Glu Leu Leu Cys Ala Arg Asn Pro Pro Arg
        195                 200                 205

Val Thr Cys Thr His Asn Glu Tyr Gly Asp His His Asp Leu Val Val
    210                 215                 220

Asp Pro Ser Glu Leu Asn Val Pro Glu Phe Arg Gly Ser Thr Asp Gly
225                 230                 235                 240

Ala Ala His Arg Cys Phe Ile Ile Gly Pro Lys Glu Leu Ser Asn Ile
                245                 250                 255

Arg Lys Trp Ile Pro Pro His Leu His Pro Cys Ser Lys Phe Glu Ile
            260                 265                 270

Ile Thr Ala Cys Leu Trp Arg Cys His Ala Ile Ala Ser Gln Ala Asn
        275                 280                 285
```

```
Pro Asn Glu Glu Met Arg Ile Cys Met Leu Val Asn Ala Arg Ser Lys
    290                 295                 300
Phe Asn Pro Pro Leu Pro Lys Gly Tyr Tyr Gly Asn Val Leu Ala Leu
305                 310                 315                 320
Pro Ala Ala Ile Thr Ser Ala Arg Lys Leu Cys Leu Asn Ser Leu Gly
                325                 330                 335
Tyr Ala Leu Glu Leu Ile Arg Gln Ala Lys Asn Lys Ile Thr Glu Glu
            340                 345                 350
Tyr Ile Arg Ser Leu Ala Asp Phe Ile Glu Ile Thr Lys Gly Leu Pro
        355                 360                 365
Lys Gly Leu Gln Ser Tyr Val Val Ser Asp Leu Thr Ser Val Gly Phe
    370                 375                 380
Asp Gln Val Asp Tyr Gly Trp Gly Lys Pro Val Tyr Thr Gly Pro Ser
385                 390                 395                 400
Lys Ala Met Pro Asp Asp Ile Asn Asn Ser Gly Thr Tyr Tyr Leu Pro
                405                 410                 415
Tyr Arg Asn Lys Lys Gly Glu Arg Gly Val Met Val Leu Ile Ser Leu
            420                 425                 430
Arg Ala Pro Val Met Ala Arg Phe Ala Met Leu Phe Glu Glu Leu Thr
        435                 440                 445
Lys His Asp Pro Asp Ser Gly Pro Ala Gln His His Thr Thr Leu Pro
    450                 455                 460
Ile Arg His Arg Leu
465

<210> SEQ ID NO 13
<211> LENGTH: 1299
<212> TYPE: DNA
<213> ORGANISM: Populus balsamifera subsp. trichocarpa

<400> SEQUENCE: 13
atggcagatg gtagtaacga tgctttaaaa cttactgtta agcaaggaga accgactctg      60
gttcctccag cagaggagac aaagaagggc ctgtactttc tctcaaacct tgatcaaaat     120
atcgcagtca tagttcgtac aatttactgc tttaagtctg acgtgaaagg aaatgaggat     180
gctgtggaag tcattaagaa tgccttgtca aaaattcttg tgcactacta ccaatagct      240
gggcggctaa caattagctc aaaaggaaag ctgatagtgg attgcaccgg gaaggtgct      300
gttttttgttg aggctgaaac ggattgtgaa atagccgagc ttggagacat aacaaaacct     360
gatcctgtga ctcttgggaa gttggtttat gaaattcctg gtgcacaaaa catacttcag     420
atgcctcctg taacggctca ggtgactaaa ttcaaatgtg gaggatttgt tcttgggcta     480
tgcacgaacc attgtatgtt cgatggaatt ggtgctatgg agtttgtgaa ttcatgggga     540
gctactgcta ggggtttggc tcttgatgta cctccatttc tagataagag catactcaaa     600
gctcgaatcc cgcctaagat agagtttcca caccatgaat tgatgacat tgaagatgtg     660
tcaaatacca gcaagcttta tgaagaggaa atgctctata gatctttctg ttttgacccc     720
gagaaacttg atcaactcaa ggaaaaagct atggaagacg agttatagc caagtgcaca     780
acatttcaag ttctctcagc ctttgtgtgg agagctcgat gccaggcatt gaagatggtg     840
cctgatcaac agataaagct cctgtttgct gcagatggac ggtctagatt tgagccacca     900
attcctgaag atactttggg caatgcgatc gtgttaacaa attctctgtg cacagcagga     960
gagataatgg aaaaccagtt gtcctttgct gtaaggctag ttcaggaggc agttaaaatg    1020
gttgatgaca gttatatgag atcagcgata gattattttg aagttacaag agccaggccc    1080
```

```
tctctgactg caactcttct aatcacaact tggtctaggc tatctttcca cacaacagac      1140
ttcggatggg gggtgcctat tttatcaggg cctgtggctc taccagagaa ggaagtaatt      1200
ctcttccttt ctcatgggat tgagaggaaa aacataaacg ttctcgtagg cctgccagct      1260
tcttccatga agatatttga agaactaatg cagatttga                             1299

<210> SEQ ID NO 14
<211> LENGTH: 432
<212> TYPE: PRT
<213> ORGANISM: Populus balsamifera subsp. trichocarpa

<400> SEQUENCE: 14
```

| Met | Ala | Asp | Gly | Ser | Asn | Asp | Ala | Leu | Lys | Leu | Thr | Val | Lys | Gln | Gly |
|---|---|---|---|---|---|---|---|---|---|---|---|---|---|---|---|
| 1 | | | | 5 | | | | | 10 | | | | | 15 | |

| Glu | Pro | Thr | Leu | Val | Pro | Pro | Ala | Glu | Glu | Thr | Lys | Lys | Gly | Leu | Tyr |
|---|---|---|---|---|---|---|---|---|---|---|---|---|---|---|---|
| | | | 20 | | | | | 25 | | | | | 30 | | |

| Phe | Leu | Ser | Asn | Leu | Asp | Gln | Asn | Ile | Ala | Val | Ile | Val | Arg | Thr | Ile |
|---|---|---|---|---|---|---|---|---|---|---|---|---|---|---|---|
| | | | 35 | | | | | 40 | | | | | 45 | | |

| Tyr | Cys | Phe | Lys | Ser | Asp | Val | Lys | Gly | Asn | Glu | Asp | Ala | Val | Glu | Val |
|---|---|---|---|---|---|---|---|---|---|---|---|---|---|---|---|
| | 50 | | | | | 55 | | | | | 60 | | | | |

| Ile | Lys | Asn | Ala | Leu | Ser | Lys | Ile | Leu | Val | His | Tyr | Tyr | Pro | Ile | Ala |
|---|---|---|---|---|---|---|---|---|---|---|---|---|---|---|---|
| 65 | | | | | 70 | | | | | 75 | | | | | 80 |

| Gly | Arg | Leu | Thr | Ile | Ser | Ser | Lys | Gly | Lys | Leu | Ile | Val | Asp | Cys | Thr |
|---|---|---|---|---|---|---|---|---|---|---|---|---|---|---|---|
| | | | | 85 | | | | | 90 | | | | | 95 | |

| Gly | Glu | Gly | Ala | Val | Phe | Val | Glu | Ala | Glu | Thr | Asp | Cys | Glu | Ile | Ala |
|---|---|---|---|---|---|---|---|---|---|---|---|---|---|---|---|
| | | | | 100 | | | | | 105 | | | | | 110 | |

| Glu | Leu | Gly | Asp | Ile | Thr | Lys | Pro | Asp | Pro | Val | Thr | Leu | Gly | Lys | Leu |
|---|---|---|---|---|---|---|---|---|---|---|---|---|---|---|---|
| | | | 115 | | | | | 120 | | | | | 125 | | |

| Val | Tyr | Glu | Ile | Pro | Gly | Ala | Gln | Asn | Ile | Leu | Gln | Met | Pro | Pro | Val |
|---|---|---|---|---|---|---|---|---|---|---|---|---|---|---|---|
| | 130 | | | | | 135 | | | | | 140 | | | | |

| Thr | Ala | Gln | Val | Thr | Lys | Phe | Lys | Cys | Gly | Gly | Phe | Val | Leu | Gly | Leu |
|---|---|---|---|---|---|---|---|---|---|---|---|---|---|---|---|
| 145 | | | | | 150 | | | | | 155 | | | | | 160 |

| Cys | Thr | Asn | His | Cys | Met | Phe | Asp | Gly | Ile | Gly | Ala | Met | Glu | Phe | Val |
|---|---|---|---|---|---|---|---|---|---|---|---|---|---|---|---|
| | | | | 165 | | | | | 170 | | | | | 175 | |

| Asn | Ser | Trp | Gly | Ala | Thr | Ala | Arg | Gly | Leu | Ala | Leu | Asp | Val | Pro | Pro |
|---|---|---|---|---|---|---|---|---|---|---|---|---|---|---|---|
| | | | | 180 | | | | | 185 | | | | | 190 | |

| Phe | Leu | Asp | Arg | Ser | Ile | Leu | Lys | Ala | Arg | Ile | Pro | Pro | Lys | Ile | Glu |
|---|---|---|---|---|---|---|---|---|---|---|---|---|---|---|---|
| | | | 195 | | | | | 200 | | | | | 205 | | |

| Phe | Pro | His | His | Glu | Phe | Asp | Asp | Ile | Glu | Asp | Val | Ser | Asn | Thr | Ser |
|---|---|---|---|---|---|---|---|---|---|---|---|---|---|---|---|
| | 210 | | | | | 215 | | | | | 220 | | | | |

| Lys | Leu | Tyr | Glu | Glu | Glu | Met | Leu | Tyr | Arg | Ser | Phe | Cys | Phe | Asp | Pro |
|---|---|---|---|---|---|---|---|---|---|---|---|---|---|---|---|
| 225 | | | | | 230 | | | | | 235 | | | | | 240 |

| Glu | Lys | Leu | Asp | Gln | Leu | Lys | Glu | Lys | Ala | Met | Glu | Asp | Gly | Val | Ile |
|---|---|---|---|---|---|---|---|---|---|---|---|---|---|---|---|
| | | | | 245 | | | | | 250 | | | | | 255 | |

| Ala | Lys | Cys | Thr | Thr | Phe | Gln | Val | Leu | Ser | Ala | Phe | Val | Trp | Arg | Ala |
|---|---|---|---|---|---|---|---|---|---|---|---|---|---|---|---|
| | | | 260 | | | | | 265 | | | | | 270 | | |

| Arg | Cys | Gln | Ala | Leu | Lys | Met | Val | Pro | Asp | Gln | Gln | Ile | Lys | Leu | Leu |
|---|---|---|---|---|---|---|---|---|---|---|---|---|---|---|---|
| | | 275 | | | | | 280 | | | | | 285 | | | |

| Phe | Ala | Ala | Asp | Gly | Arg | Ser | Arg | Phe | Glu | Pro | Pro | Ile | Pro | Glu | Gly |
|---|---|---|---|---|---|---|---|---|---|---|---|---|---|---|---|
| | | 290 | | | | | 295 | | | | | 300 | | | |

| Tyr | Phe | Gly | Asn | Ala | Ile | Val | Leu | Thr | Asn | Ser | Leu | Cys | Thr | Ala | Gly |
|---|---|---|---|---|---|---|---|---|---|---|---|---|---|---|---|
| 305 | | | | | 310 | | | | | 315 | | | | | 320 |

| Glu | Ile | Met | Glu | Asn | Gln | Leu | Ser | Phe | Ala | Val | Arg | Leu | Val | Gln | Glu |
|---|---|---|---|---|---|---|---|---|---|---|---|---|---|---|---|
| | | | | 325 | | | | | 330 | | | | | 335 | |

```
Ala Val Lys Met Val Asp Asp Ser Tyr Met Arg Ser Ala Ile Asp Tyr
            340                 345                 350

Phe Glu Val Thr Arg Ala Arg Pro Ser Leu Thr Ala Thr Leu Leu Ile
        355                 360                 365

Thr Thr Trp Ser Arg Leu Ser Phe His Thr Thr Asp Phe Gly Trp Gly
    370                 375                 380

Val Pro Ile Leu Ser Gly Pro Val Ala Leu Pro Glu Lys Glu Val Ile
385                 390                 395                 400

Leu Phe Leu Ser His Gly Ile Glu Arg Lys Asn Ile Asn Val Leu Val
                405                 410                 415

Gly Leu Pro Ala Ser Ser Met Lys Ile Phe Glu Glu Leu Met Gln Ile
            420                 425                 430

<210> SEQ ID NO 15
<211> LENGTH: 1329
<212> TYPE: DNA
<213> ORGANISM: Populus balsamifera subsp. trichocarpa

<400> SEQUENCE: 15
atgggtatag aggctgaaaa gttttctgca atggagtact ctaatggcaa tgtatttcaa      60
ctagttgtga acaaggaga gccaactctt gttcctccag ccgaggagac agagaagggt     120
ctttactttc tctccaacct tgaccaaaac attgcagtga ttgtgcgtac aatctactgc    180
ttcaagtcag aagagaaagg aaatgaaaat gctggagaag tgatcaagaa tgccttgaaa    240
aaggttcttg tgcactacta tcctcttgcc gggcggctaa caataagctc agaggcaaag    300
cttattataa attgcactgg agaaggtgct gttttgttg aggctgaagc aaactgtgca     360
ctggaagaga ttggtgacat aacaaagccc gatccagaca ctcttgggaa gctggtttat    420
gacattcctg gtgcaaagaa catactggag atgcctcctt ggtggctca ggtcaccaag     480 ttcacatgtg aggatttgc actaggattg tgcatgaatc attgtatgtt tgatggcatt     540
ggtgctatgg aatttgtgaa ctcatggggt gaaacagcca gaggcttgcc actctgtgtc    600
cctccattca ttgacagaag catacttaaa gcccggaacc ctccaaagat tgagtacccc    660
caccaagaat tcgccgagat aaaagacaag tccagcacaa atgaccttta caagatgaa     720 atgctctaca gctccttctg tttcgattct gaaatgcttg aaaagatcaa atgaaagcc     780 atggaagatg gggttcttgg aaagtgcact acttttgaag gctctcagc ttttgtatgg     840 agagctcgaa ccaaggcact caaaatgctg cctgatcaac aaacaaagct cctatttgct    900
gtcgatggaa ggccaaaatt taaaccccc ctaccaaaag ggtacttcgg aaatggaatt    960
gtgttgacca attcgatgtg ccaagcaggg gaactactag acaggccact atcacatgca   1020
gtggggcttg ttcaagatgc aattaaaatg gtcacagaca gttacatgag atctgctatg   1080
gattattttg aagcaacaag agttaggcct tctctggctt cgactctact gataacaact   1140
tggtctaggc tatctttcta cactacagat tttgggtggg gagagccagt tctatctggg   1200
ccagtggcat taccagagaa ggaagtcatc ctgttcctat ctcatggcaa agagagaaaa   1260
agcataaatg tgcttctggg tctgccagct ttagccatga agaccttcca agaaatgata   1320
cagatttag                                                            1329

<210> SEQ ID NO 16
<211> LENGTH: 442
<212> TYPE: PRT
<213> ORGANISM: Populus balsamifera subsp. trichocarpa
```

<400> SEQUENCE: 16

```
Met Gly Ile Glu Ala Glu Lys Phe Ser Ala Met Glu Tyr Ser Asn Gly
1               5                   10                  15

Asn Val Phe Gln Leu Val Val Lys Gln Gly Glu Pro Thr Leu Val Pro
                20                  25                  30

Pro Ala Glu Glu Thr Glu Lys Gly Leu Tyr Phe Leu Ser Asn Leu Asp
            35                  40                  45

Gln Asn Ile Ala Val Ile Val Arg Thr Ile Tyr Cys Phe Lys Ser Glu
    50                  55                  60

Glu Lys Gly Asn Glu Asn Ala Gly Glu Val Ile Lys Asn Ala Leu Lys
65                  70                  75                  80

Lys Val Leu Val His Tyr Tyr Pro Leu Ala Gly Arg Leu Thr Ile Ser
                85                  90                  95

Ser Glu Ala Lys Leu Ile Ile Asn Cys Thr Gly Glu Gly Ala Val Phe
            100                 105                 110

Val Glu Ala Glu Ala Asn Cys Ala Leu Glu Glu Ile Gly Asp Ile Thr
        115                 120                 125

Lys Pro Asp Pro Asp Thr Leu Gly Lys Leu Val Tyr Asp Ile Pro Gly
    130                 135                 140

Ala Lys Asn Ile Leu Glu Met Pro Leu Val Ala Gln Val Thr Lys
145                 150                 155                 160

Phe Thr Cys Gly Gly Phe Ala Leu Gly Leu Cys Met Asn His Cys Met
                165                 170                 175

Phe Asp Gly Ile Gly Ala Met Glu Phe Val Asn Ser Trp Gly Glu Thr
            180                 185                 190

Ala Arg Gly Leu Pro Leu Cys Val Pro Pro Phe Ile Asp Arg Ser Ile
        195                 200                 205

Leu Lys Ala Arg Asn Pro Pro Lys Ile Glu Tyr Pro His Gln Glu Phe
    210                 215                 220

Ala Glu Ile Lys Asp Lys Ser Ser Thr Asn Asp Leu Tyr Lys Asp Glu
225                 230                 235                 240

Met Leu Tyr Ser Ser Phe Cys Phe Asp Ser Glu Met Leu Glu Lys Ile
                245                 250                 255

Lys Met Lys Ala Met Glu Asp Gly Val Leu Gly Lys Cys Thr Thr Phe
            260                 265                 270

Glu Gly Leu Ser Ala Phe Val Trp Arg Ala Arg Thr Lys Ala Leu Lys
        275                 280                 285

Met Leu Pro Asp Gln Gln Thr Lys Leu Leu Phe Ala Val Asp Gly Arg
    290                 295                 300

Pro Lys Phe Lys Pro Pro Leu Pro Lys Gly Tyr Phe Gly Asn Gly Ile
305                 310                 315                 320

Val Leu Thr Asn Ser Met Cys Gln Ala Gly Glu Leu Leu Asp Arg Pro
                325                 330                 335

Leu Ser His Ala Val Gly Leu Val Gln Asp Ala Ile Lys Met Val Thr
            340                 345                 350

Asp Ser Tyr Met Arg Ser Ala Met Asp Tyr Phe Glu Ala Thr Arg Val
        355                 360                 365

Arg Pro Ser Leu Ala Ser Thr Leu Leu Ile Thr Thr Trp Ser Arg Leu
    370                 375                 380

Ser Phe Tyr Thr Thr Asp Phe Gly Trp Gly Glu Pro Val Leu Ser Gly
385                 390                 395                 400

Pro Val Ala Leu Pro Glu Lys Glu Val Ile Leu Phe Leu Ser His Gly
                405                 410                 415
```

Lys Glu Arg Lys Ser Ile Asn Val Leu Leu Gly Leu Pro Ala Leu Ala
            420                 425                 430

Met Lys Thr Phe Gln Glu Met Ile Gln Ile
            435                 440

<210> SEQ ID NO 17
<211> LENGTH: 1323
<212> TYPE: DNA
<213> ORGANISM: Populus balsamifera subsp. trichocarpa

<400> SEQUENCE: 17

| | |
|---|---|
| atggaaggaa cgggaaaaca tggaggtgac cagctttcag ttaagaagtc agaacccgtt | 60 |
| ctaatagaac ctgaaacaag gactcatagt gggttttttt tcttatgcaa tcttgatcac | 120 |
| atggtcactc attccgtgga aacagtgtac ttctacaagg caaagaaatg ggaggcagt | 180 |
| cgtgacaccc tcagtgacac atttaaacaa tctctggcca agattctggt gcattattac | 240 |
| cctctcgcag ggagattaag attaggatct gatgggaaga taatgtgga gtgtaccaat | 300 |
| gaagggtgt tgtttgtgga agcaagagca aattgtaaca tggatcaagt tgacgttaaa | 360 |
| gtaattattg atgatcattc tgaaacagca gggaagcttg tctatggatc tccagatcct | 420 |
| gagaacatac tggaaaaccc tctaatgact gcacaggtta caaggttcag gtgtggaggt | 480 |
| tttgctttgg gattatcaat tagccactta atagctgatg ggctatcagc aatggagttt | 540 |
| atcaaatcat ggtctgaaac agccagaggg atgccgttaa ccactaaacc agttcttgat | 600 |
| agatcaattt tgaggtctag acaacctcct aaaattgatt tcatttcga ccagtacgct | 660 |
| cctgcagaaa ccagtaacgt atcaaacata tcaaatccat tcaaggaga gcagattctg | 720 |
| acgaaatgct tcctgtttga ttccaacaag cttgcaatac tgaagagcat ggcaatggag | 780 |
| gacggaacca tcaaaagctg ctcaaacttc acagcgctca cagcttttgt gtggcgtgct | 840 |
| cgctgcaagg cactgcagat gaatcctgat caaacaactc cacttctgtt agtagtcgac | 900 |
| gttcgatcca agcttaatcc accacttccc aaaggatact ttggcaacgg aattgtctta | 960 |
| atcacttgcc ctgggagggc aggagaattg attaaaaaca cactatcttt tgcagtggaa | 1020 |
| gaagtgcaga atgaataaa atggtgaat gaggagtttg tcaggtcttg gattgattac | 1080 |
| cttgaagtga tgggagcaaa ggactttcct ttacactcct attttaaagt ttcttcatgg | 1140 |
| acaagacttt caattgagtg ttcagacttt ggatggggag agccagcaca gtttgcttgc | 1200 |
| acaaacttgc ctaaaaattc agcttttttc ctaccagatg gaaaagaaaa gaagggcatt | 1260 |
| aatttgattt tggatttgcc agttactgcc atgagcacct tccaggagct aatgcttctg | 1320 |
| taa | 1323 |

<210> SEQ ID NO 18
<211> LENGTH: 440
<212> TYPE: PRT
<213> ORGANISM: Populus balsamifera subsp. trichocarpa

<400> SEQUENCE: 18

Met Glu Gly Thr Gly Lys His Gly Gly Asp Gln Leu Ser Val Lys Lys
1               5                   10                  15

Ser Glu Pro Val Leu Ile Glu Pro Glu Thr Arg Thr His Ser Gly Phe
            20                  25                  30

Phe Phe Leu Cys Asn Leu Asp His Met Val Thr His Ser Val Glu Thr
        35                  40                  45

Val Tyr Phe Tyr Lys Ala Lys Lys Trp Gly Gly Ser Arg Asp Thr Leu

```
              50                  55                  60
Ser Asp Thr Phe Lys Gln Ser Leu Ala Lys Ile Leu Val His Tyr Tyr
 65                  70                  75                  80

Pro Leu Ala Gly Arg Leu Arg Leu Gly Ser Asp Gly Lys Tyr Asn Val
                 85                  90                  95

Glu Cys Thr Asn Glu Gly Val Leu Phe Val Glu Ala Arg Ala Asn Cys
                100                 105                 110

Asn Met Asp Gln Val Asp Val Lys Val Ile Ile Asp Asp His Ser Glu
                115                 120                 125

Thr Ala Gly Lys Leu Val Tyr Gly Ser Pro Asp Pro Glu Asn Ile Leu
                130                 135                 140

Glu Asn Pro Leu Met Thr Ala Gln Val Thr Arg Phe Arg Cys Gly Gly
145                 150                 155                 160

Phe Ala Leu Gly Leu Ser Ile Ser His Leu Ile Ala Asp Gly Leu Ser
                165                 170                 175

Ala Met Glu Phe Ile Lys Ser Trp Ser Glu Thr Ala Arg Gly Met Pro
                180                 185                 190

Leu Thr Thr Lys Pro Val Leu Asp Arg Ser Ile Leu Arg Ser Arg Gln
                195                 200                 205

Pro Pro Lys Ile Asp Phe His Phe Asp Gln Tyr Ala Pro Ala Glu Thr
                210                 215                 220

Ser Asn Val Ser Asn Ile Ser Asn Pro Phe Gln Gly Glu Gln Ile Leu
225                 230                 235                 240

Thr Lys Cys Phe Leu Phe Asp Ser Asn Lys Leu Ala Ile Leu Lys Ser
                245                 250                 255

Met Ala Met Glu Asp Gly Thr Ile Lys Ser Cys Ser Asn Phe Thr Ala
                260                 265                 270

Leu Thr Ala Phe Val Trp Arg Ala Arg Cys Lys Ala Leu Gln Met Asn
                275                 280                 285

Pro Asp Gln Thr Thr Pro Leu Leu Leu Val Val Asp Val Arg Ser Lys
                290                 295                 300

Leu Asn Pro Pro Leu Pro Lys Gly Tyr Phe Gly Asn Gly Ile Val Leu
305                 310                 315                 320

Ile Thr Cys Pro Gly Arg Ala Gly Glu Leu Ile Lys Asn Thr Leu Ser
                325                 330                 335

Phe Ala Val Glu Glu Val Gln Asn Gly Ile Lys Met Val Asn Glu Glu
                340                 345                 350

Phe Val Arg Ser Trp Ile Asp Tyr Leu Glu Val Met Gly Ala Lys Asp
                355                 360                 365

Phe Pro Leu His Ser Tyr Phe Lys Val Ser Ser Trp Thr Arg Leu Ser
                370                 375                 380

Ile Glu Cys Ser Asp Phe Gly Trp Gly Glu Pro Ala Gln Phe Ala Cys
385                 390                 395                 400

Thr Asn Leu Pro Lys Asn Ser Ala Phe Phe Leu Pro Asp Gly Lys Glu
                405                 410                 415

Lys Lys Gly Ile Asn Leu Ile Leu Asp Leu Pro Val Thr Ala Met Ser
                420                 425                 430

Thr Phe Gln Glu Leu Met Leu Leu
                435                 440

<210> SEQ ID NO 19
<211> LENGTH: 2951
<212> TYPE: DNA
<213> ORGANISM: Arabidopsis thaliana
```

<400> SEQUENCE: 19

```
aagcttagag gagaaactga gaaaatcagc gtaatgagag acgagagcaa tgtgctaaga     60
gaagagattg ggaagagaga agagacgata aaggaaacgg aaaagcatat ggaggagctt    120
catatggagc aagtgaggct gagaagacgg tcgagtgagc ttacggaaga agtggaaagg    180
acgagagtgt ctgcatcgga aatggctgag cagaaaagag aagctataag acagctttgt    240
atgtctcttg accattacag agatgggtac gacaggcttt ggagagttgt tgccggccat    300
aagagtaaga gagtagtggt tttaacaact tgaagtgtaa aacaatgag tcaatgacta    360
cgtgcaggac attggacata ccgtgtgttc ttttggattg aaatgttgtt tcgaagggct    420
gttagttgat gttgaaaata ggttgaagtt gaataatgca tgttgatata gtaaatatca    480
atggtaatat tttctcattt cccaaaactc aaatgatatc atttaattat aaactaacgt    540
aaactgttga caatacactt atggttaaaa atttggagtc ttgttttagt atacgtatca    600
ccaccgcacg gtttcaaaac cacataattg taaatgttat tggaaaaaag aacccgcaat    660
acgtattgta ttttggtaaa catagctcta agcctctaat atataagctc tcaacaattc    720
tggctaatgg tcccaagtaa gaaaagccca tgtattgtaa ggtcatgatc tcaaaaacga    780
gggtgaggtg gaatactaac atgaggagaa agtaaggtga caaatttttg gggcaatagt    840
ggtggatatg gtggggaggt aggtagcatc atttctccaa gtcgctgtct ttcgtggtaa    900
tggtaggtgt gtctctcttt atattattta ttactactca ttgttaattt cttttttcct    960
acaatttgtt tcttactcca aaatacgtca caaatataat actaggcaaa taattattta   1020
attgtaagtc aatagagtgg ttgttgtaaa attgattttt gatattgaaa gagttcatgg   1080
acggatgtgt atgcgccaaa tgctaagccc ttgtagtctt gtactgtgcc gcgcgtatat   1140
tttaaccacc actagttgtt tctcttttc aaaaacacac aaaaaataat ttgttttcgt   1200
aacggcgtca aatctgacgg cgtctcaata cgttcaattt tttctttctt tcacatggtt   1260
tctcatagct ttgcattgac cataggtaaa gggataagga taaggttttt ttctcttgtt   1320
tgttttatcc ttattattca aaatggataa aaaaacagtc ttattttgat ttctttgatt   1380
aaaaaagtca ttgaaattca tatttgattt tttgctaaat gtcaactcag agacacaaac   1440
gtaatgcact gtcgccaata ttcatggatc atgaccatga atatcactag aataattgaa   1500
aatcagtaaa atgcaaacaa agcatttctc aattaaaaca gtcttctaca ttcacttaat   1560
tggaatttcc tttatcaaac ccaaagtcca aaacaatcgg caatgttttg caaaatgttc   1620
aaaactattg gcgggttggt ctatccgaat tgaagatctt ttctccatat gatagaccaa   1680
cgaaattcgg catacgtgtt ttttttttttg ttttgaaaac cctttaaaca accttaattc   1740
aaaatactaa tgtaacttta ttgaacgtgc atctaaaaat tttgaacttt gcttttgaga   1800
aataatcaat gtaccaataa agaagatgta gtacatacat tataattaaa tacaaaaaag   1860
gaatcaccat atagtacatg gtagacaatg aaaaacttta aaacatatac aatcaataat   1920
actctttgtg cataactttt tttgtcgtct cgagtttata tttgagtact tatacaaact   1980
attagattac aaactgtgct cagatacatt aagttaatct tatatacaag agcactcgag   2040
tgttgtcctt aagttaatct taagatatct tgaggtaaat agaaatagtt aactcgtttt   2100
tattttcttt ttttaccat gagcaaaaaa agatgaagta agttcaaaac gtgacgaatc   2160
tacatgttac tacttagtat gtgtcaatca ttaaatcggg aaaacttcat catttcagga   2220
gtactacaaa actcctaaga gtgagaacga ctacatagta catattttga taaaagactt   2280
```

-continued

```
gaaaacttgc taaaacgaat ttgcgaaaat ataatcatac aagtagaacc actgatttga    2340
tcgaattatt catagctttg taggatgaac ttaactaaat aatatctcac aaaagtattg    2400
acagtaacct agtactatac tatctatgtt agaatatgat tatgatataa tttatcccct    2460
cacttattca tatgattttt gaagcaacta ctttcgtttt tttaacattt tcttttttgg    2520
tttttgttaa tgaacatatt tagtcgtttc ttaattccac tcaaatagaa aatacaaaga    2580
gaactttatt taatagatat gaacataatc tcacatcctc ctcctacctt caccaaacac    2640
ttttacatac actttgtggt ctttctttac ctaccaccat caacaacaac accaagcccc    2700
actcacacac acgcaatcac gttaaatcta acgccgttta ttatctcatc attcaccaac    2760
tcccacgtac ctaacgccgt ttaccttttg ccgttggtcc tcatttctca aaccaaccaa    2820
acctctccct cttataaaat cctctctccc ttctttattt cttcctcagc agcttcttct    2880
gctttcaatt actctcgccg acgattttct caccggaaaa aaacaatatc attgcggata    2940
cacaaactat a                                                        2951
```

BAHD ACYLTRANSFERASES

STATEMENT REGARDING FEDERALLY SPONSORED RESEARCH

This invention was made with government support under DE-FC02-07ER64494 awarded by the US Department of Energy. The government has certain rights in the invention.

FIELD OF THE INVENTION

The invention is directed to BAHD acyltransferase enzymes, nucleic acids encoding BAHD acyltransferase enzymes, and inhibitory nucleic acids adapted to inhibit the expression and/or translation of BAHD acyltransferase RNA; expression cassettes, plant cells, and plants that have or encode such nucleic acids and enzymes; and methods of making and using such nucleic acids, enzymes, expression cassettes, cells, and plants.

BACKGROUND

Lignin is an important cell wall component that provides structural support to plants and is needed for plant vascular tissue function. Lignin is also a source of organic material for the synthesis of chemicals. Lignin is the second most abundant organic polymer on Earth, constituting about 30% of non-fossil organic carbon and from a quarter to a third of the dry mass of wood. Because the chemical structure of lignin is difficult to degrade by chemical and enzymatic means, lignin makes the task of producing paper and biofuels from plant cell walls difficult. Modifying lignin to make it more amenable to degradation or suitable for the production of certain chemicals is desirable.

SUMMARY OF THE INVENTION

The invention relates to the identification and isolation of new BAHD acyltransferase nucleic acids and polypeptides. The BAHD acyltransferases have one or more BAHD acyltransferase activities selected from at least feruloyl-coenzyme-A (CoA):monolignol transferase (FMT) activity, p-coumaroyl-CoA:monolignol transferase (PMT) activity, p-hydroxybenzoyl-CoA:monolignol transferase (pBMT) activity, benzoyl-CoA:monolignol transferase (BMT) activity, acetyl-CoA:monolignol transferase (AMT) activity, or a combination thereof. The BAHD acyltransferases can be used for making plants that contain modified lignin. The modified lignin is amenable to degradation and production of commodity chemicals.

One aspect of the invention is a BAHD acyltransferase nucleic acid encoding a BAHD acyltransferases polypeptide. The BAHD acyltransferase nucleic acid may be an isolated nucleic acid, a recombinant nucleic acid, or both. In some embodiments, the BAHD acyltransferase nucleic acid encodes a BAHD acyltransferase polypeptide comprising a sequence identical or substantially identical to SEQ ID NO:2, SEQ ID NO:4, SEQ ID NO:6, SEQ ID NO:8, SEQ ID NO:12, SEQ ID NO:14, SEQ ID NO:16, and/or SEQ ID NO:18. In some embodiments, the nucleic acids can encode a BAHD acyltransferase with at least about 50% of at least one BAHD acyltransferase activity of a BAHD acyltransferase with the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence.

Another aspect of the invention is a transgenic plant cell comprising an isolated or recombinant nucleic acid encoding a BAHD acyltransferase. The nucleic acid can include any of the BAHD acyltransferase nucleic acids described herein. For example, the nucleic acid can include a nucleic acid segment that can selectively hybridize to a DNA with a SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence, and/or a nucleic acid that encodes a SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase polypeptide comprising a sequence substantially identical to the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase with at least about 50% of at least one BAHD acyltransferase activity of a BAHD acyltransferase with the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence.

Another aspect of the invention is an expression cassette comprising one of the BAHD acyltransferase nucleic acids described herein that is operably linked to a promoter functional in a host cell. Such a nucleic acid can include a nucleic acid segment that can selectively hybridize to a DNA with a SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence, and/or a nucleic acid that encodes a SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase polypeptide comprising a sequence substantially identical to the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase with at least about 50% of at least one BAHD acyltransferase activity of a BAHD acyltransferase with the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence. The expression cassette can further comprise a selectable marker gene. In some embodiments, the expression cassette further comprises plasmid DNA. For example, the expression cassette can be within an expression vector. Promoters that can be used within such expression cassettes include promoters functional during plant development or growth.

Another aspect of the invention is a plant cell that includes an expression cassette comprising one of the BAHD acyltransferase nucleic acids described herein that is operably linked to a promoter functional in a host cell. Such a nucleic acid can include a nucleic acid segment that can selectively hybridize to a DNA with a SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence, and/or a nucleic acid that encodes a SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase polypeptide comprising a sequence substantially identical to the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase with at least about 50% of at least one BAHD acyltransferase activity of a BAHD acyltransferase with the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence. The plant cell can be a monocot cell. The plant cell can also be a gymnosperm cell. For example, the plant cell can be a maize, grass or softwood cell. In some embodiments, the plant cell is a dicot cell. For example, the plant cell can be a hardwood cell, such as poplar or Eucalyptus.

Another aspect of the invention is a plant that includes an expression cassette comprising one of the BAHD acyltransferase nucleic acids described herein that is operably linked to a promoter functional in a host cell. Such a plant can be a monocot. Such a nucleic acid can include a nucleic acid segment that can selectively hybridize to a DNA with a SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence, and/or a nucleic acid that encodes a SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase polypeptide comprising a sequence substantially identical to the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase with at least about 50% of at least one BAHD acyltransferase activity of a BAHD acyltransferase with the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence. The plant can also be a gymnosperm. For example, the plant can be a maize, grass or softwood plant. In some embodiments, the plant is a dicot plant. For example, the plant can be a hardwood plant, such as poplar or Eucalyptus.

Another aspect of the invention is a method for incorporating monolignol ester conjugates into lignin of a plant that includes:
a) stably transforming plant cells with the expression cassette comprising one of the BAHD acyltransferase nucleic acids described herein to generate transformed plant cells;
b) regenerating the transformed plant cells into at least one transgenic plant, wherein a BAHD acyltransferase is expressed from the BAHD acyltransferase nucleic acid in at least one transgenic plant in an amount sufficient to incorporate monolignol ester conjugates into the lignin of the transgenic plant.

The BAHD acyltransferase nucleic acid can be a nucleic acid that can selectively hybridize to a DNA with a SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence, and/or a nucleic acid that encodes a SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase polypeptide comprising a sequence substantially identical to the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase with at least about 50% of at least one BAHD acyltransferase activity of a BAHD acyltransferase with the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence. The monolignol ester conjugates can comprise one or more of monolignol ferulate, monolignol p-coumarate, monolignol p-hydroxybenzoate, monolignol benzoate, and monolignol acetate, and the monolignol group in the monolignol ester conjugates can comprise one or more of a p-coumaryl group, a coniferyl group, and a sinapyl group. The method can be used to generate a transgenic plant that is fertile. The method can further include recovering transgenic seeds from the transgenic plant, wherein the transgenic seeds include the nucleic acid encoding a BAHD acyltransferase. The plant containing monolignol ester conjugates within its lignin can be a monocot. The plant can also be a gymnosperm. For example, the plant can be a maize, grass or softwood plant. In some embodiments, the plant is a dicot plant. For example, the plant can also be a hardwood plant. Such a method can further include stably transforming the plant cell(s) or the plant with at least one selectable marker gene. The selectable marker can be linked or associated with the expression cassette.

The method for incorporating monolignol ester conjugates into lignin of a plant can also include breeding the fertile transgenic plant to yield a progeny plant, where the progeny plant has an increase in the percentage of one or more of one or more of the monolignol ester conjugates made by the BAHD acyltransferase in the lignin of the progeny plant relative to the corresponding untransformed plant.

Another aspect of the invention is a lignin isolated from the transgenic plant comprising any of the BAHD acyltransferase nucleic acids described herein. Another aspect of the invention is a woody material isolated from the transgenic plant comprising any of the BAHD acyltransferase nucleic acids described herein. The lignin or woody tissue can include any of the nucleic acids described herein that encode a BAHD acyltransferase. In other embodiments, the lignin or woody tissue can include any of the BAHD acyltransferase amino acid or polypeptide sequences described herein.

Another aspect of the invention is a method of making a product from a transgenic plant comprising: (a) providing a transgenic plant that includes one of the isolated or recombinant nucleic acids described herein that encodes a BAHD acyltransferase; and (b) processing the transgenic plant's tissues under conditions sufficient to digest the lignin; to thereby generate the product from the transgenic plant, wherein the transgenic plant's tissues comprise lignin having an increased percent of monolignol ester conjugates relative to a corresponding untransformed plant. Such a corresponding untransformed plant is typically a plant of the same species, strain and/or accession as the transformed plant. The conditions sufficient to digest the lignin can include conditions sufficient to cleave ester bonds within monolignol ester conjugate-containing lignin. In some embodiments, the conditions sufficient to digest the lignin include mildly alkaline conditions. In some embodiments, the conditions sufficient to digest the lignin include treating the transgenic plant's tissues with ammonia for a time and a temperature sufficient to cleave ester bonds within monolignol ester conjugate-containing lignin. In some embodiments, the conditions sufficient to digest the lignin include acidic conditions.

Another aspect of the invention is an isolated or recombinant nucleic acid encoding a BAHD acyltransferase, wherein the nucleic acid can selectively hybridize to a DNA with a SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence. For example, the nucleic acid can selectively hybridize to a DNA with a SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence under stringent hybridization conditions. In some embodiments, the stringent hybridization conditions comprise a wash in 0.1×SSC, 0.1% SDS at 65° C. Such an isolated or recombinant nucleic acid can have at least about 79%, at least about 80%, at least about 90%, or at least 95% sequence identity with SEQ ID NO:1, SEQ ID NO:3, SEQ ID NO:5, SEQ ID NO:7, SEQ ID NO:11, SEQ ID NO:13, SEQ ID NO:15, or SEQ ID NO:17. In some embodiments, the nucleic acid with the SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence encodes a BAHD acyltransferase.

Other aspects of the invention include inhibitory nucleic acids adapted to inhibit expression and/or translation of a BAHD acyltransferase mRNA; expression cassettes, plant cells, and plants comprising the inhibitory nucleic acids; methods pertaining to the use of the inhibitory nucleic acids; transgenic plants comprising a knockdown or knockout of the plant's endogenous BAHD acyltransferase; and other aspects as described in the following statements of the invention and elsewhere herein.

Therefore, the invention embraces BAHD acyltransferase enzymes, nucleic acids encoding or inhibiting expression of BAHD acyltransferase enzymes, as well as expression cassettes, plant cells, and plants that have or encode such nucleic acids and enzymes, and methods of making and using such nucleic acids, polypeptides, expression cassettes, cells, and plants. All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting. The following is presented by way of illustration and does not limit the scope of the invention.

BRIEF DESCRIPTION OF THE DRAWINGS

FIGS. 1A and 1B show examples of lignin structures that may be found in a softwood (spruce). FIGS. 1C and 1D show examples of lignin structures that may be present in a hardwood (poplar). (Ralph, J., Brunow, G., and Boerjan, W. (2007) Lignins. In: Rose, F., and Osborne, K. (eds). Encyclopedia of Life Sciences, DOI: 10.1002/9780470015902.a0020104, John Wiley & Sons, Ltd., Chichester, UK). The softwood lignin is generally more branched and contains a lower proportion of β-ether units. Note that each of these structures represents only one of billions of possible isomers (Ralph, J., Lundquist, K., Brunow, G., Lu, F., Kim, H., Schatz, P. F., Marita, J. M., Hatfield, R. D., Ralph, S. A., Christensen, J. H., and Boerjan, W. (2004) Lignins: natural polymers from oxidative coupling of 4-hydroxyphenylpropanoids. *Phytochem. Revs.* 3(1):29-60). Thus, these structures are merely illustrative of some of the linkage types that may be present different lignins. An "S" within a ring indicates a syringyl unit while a "G" within a unit indicates a guaiacyl unit.

FIG. 2A shows the structure of sinapyl alcohol as a possible reactant. Coniferyl alcohol, another possible reactant, lacks one of the two methoxy groups present on sinapyl alcohol. p-Hydroxycinnamyl alcohol (p-coumaryl alcohol), another possible reactant, lacks both of the two methoxy groups present on sinapyl alcohol. FIG. 2B shows the structure of p-coumaroyl-CoA, another possible reactant. FIG. 2C shows the structure of feruloyl-CoA, another possible reactant. FIG. 2D shows the structure of sinapyl p-coumarate as a possible product resulting from the conjugation of sinapyl alcohol with p-coumaryl-CoA. Coniferyl p-coumarate, a possible product resulting from the conjugation of coniferyl alcohol with p-coumaryl-CoA, lacks one of the two methoxy groups present on sinapyl p-coumarate. p-Hydroxycinnamyl coumarate (p-coumaryl coumarate), a possible product resulting from the conjugation of p-hydroxycinnamyl alcohol and p-coumaryl-CoA, lacks both of the two methoxy groups present on sinapyl p-coumarate. FIG. 2E shows the structure of sinapyl ferulate as a possible product resulting from the conjugation of sinapyl alcohol with feruloyl-CoA. Coniferyl ferulate, a possible product resulting from the conjugation of coniferyl alcohol with feruloyl-CoA, lacks one of the two methoxy groups present on sinapyl ferulate. p-Hydroxycinnamyl ferulate (p-coumaryl ferulate), a possible product resulting from the conjugation of p-hydroxycinnamyl alcohol and feruloyl-CoA, lacks both of the two methoxy groups present on sinapyl ferulate.

FIGS. 3A-6 show alignments of amino acid sequences of exemplary BAHD acyltransferases (XMTs) of the invention generated by Clustal 0 (version 1.2.4). FIGS. 3A-3C show an alignment of all the exemplary XMTs. FIGS. 4A-4B show an alignment of a first group of XMTs. FIG. 5 shows an alignment of a second group of XMTs. FIG. 6 shows a subgroup within the second group of XMTs.

FIG. 7A shows three representative liquid chromatography (LC) absorption chromatograms (left) depicting the elution window for the assayed transferase products (center). XMT1 is a ubiquitous acyltransferase, having activity with all five CoA substrates tested. XMT2 is an example of an enzyme with primarily pBMT activity. XMT4 is an example of an enzyme with primarily FMT activity. FIG. 7B shows a table summarizing activities of the XMT enzymes.

DETAILED DESCRIPTION OF THE INVENTION

Figure 1A:
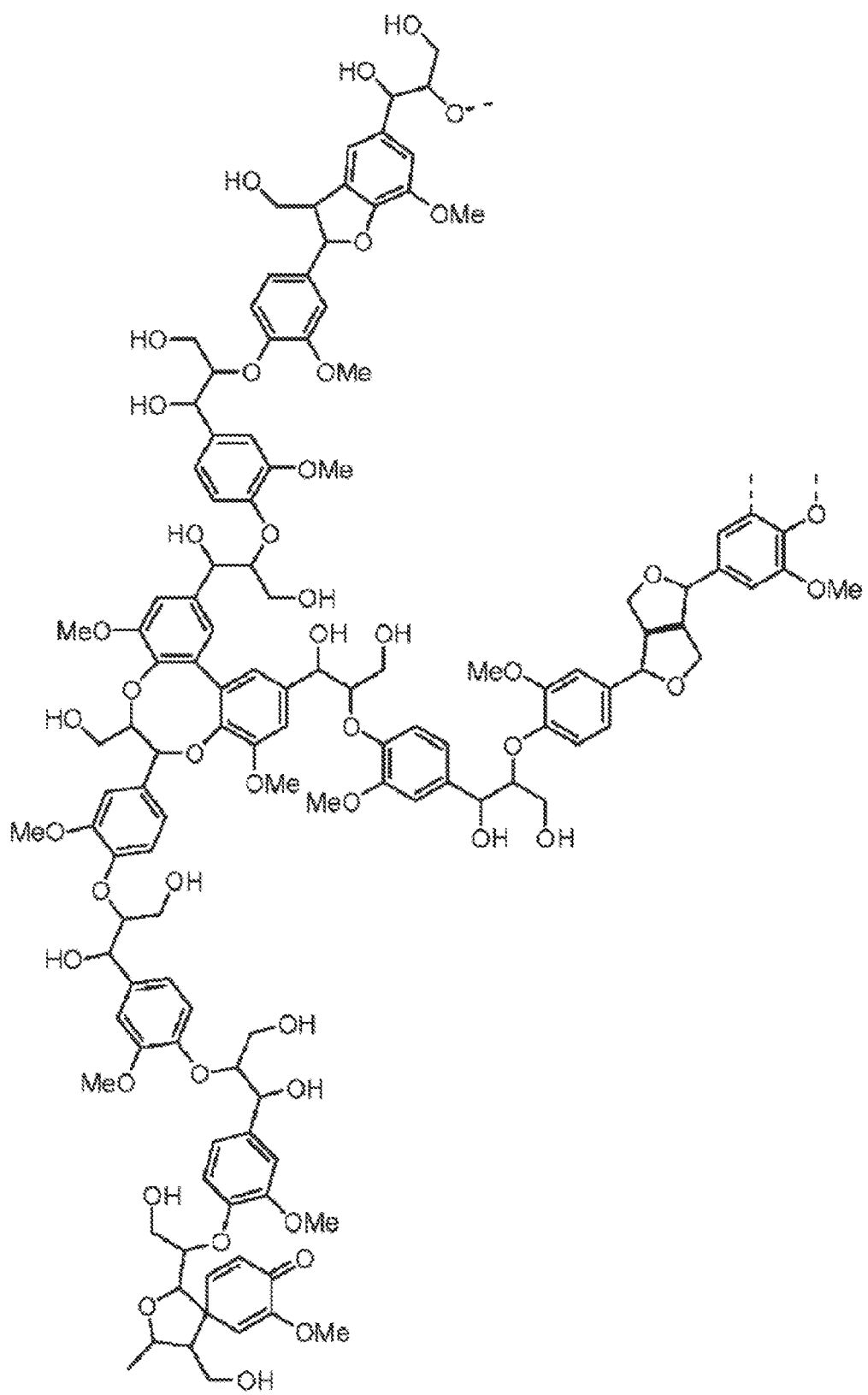
FIGS. 1A-1D illustrate structural models for some types of lignin polymers.
Figure 1B:
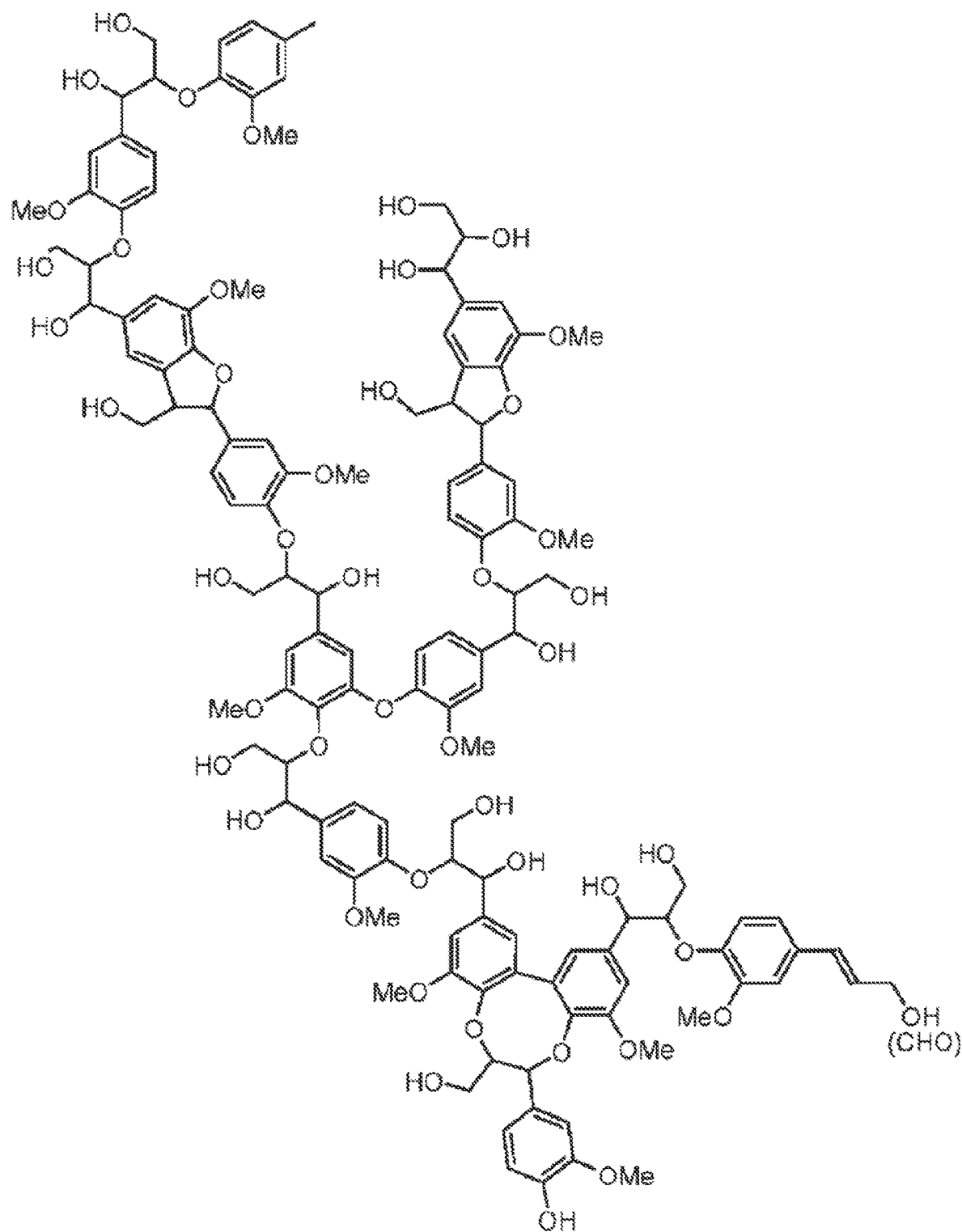
Figure 1C:
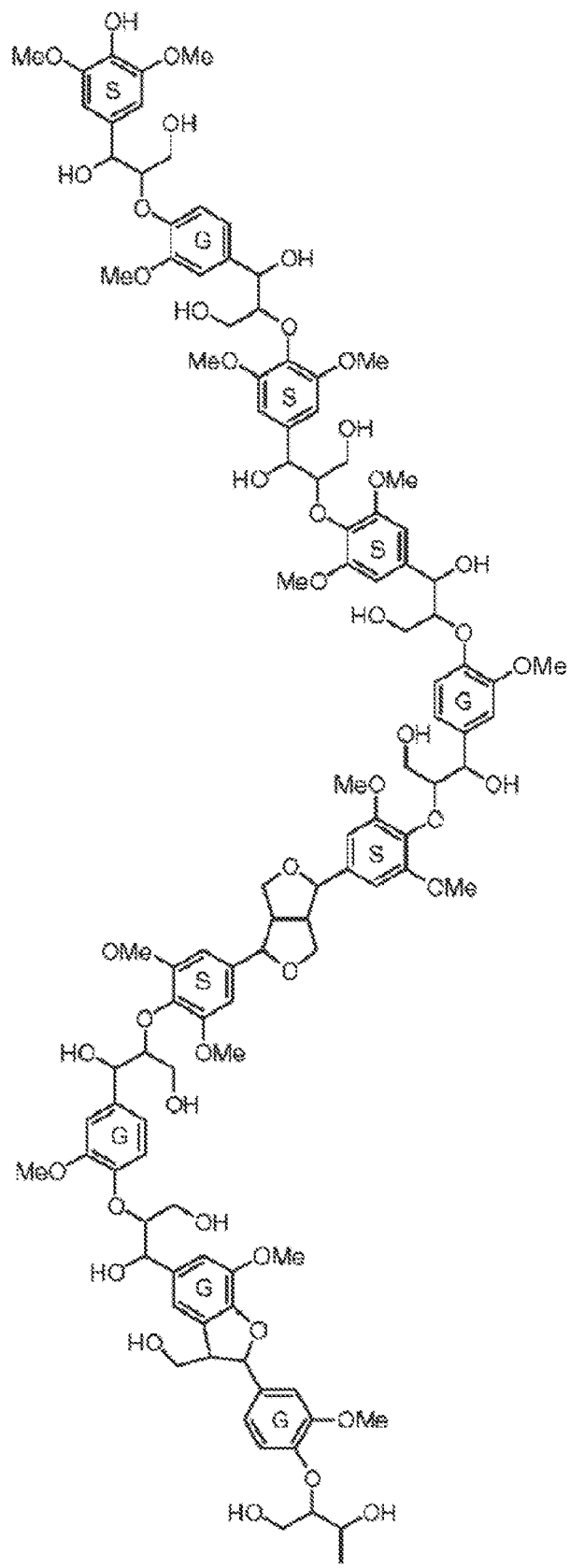
Figure 1D:
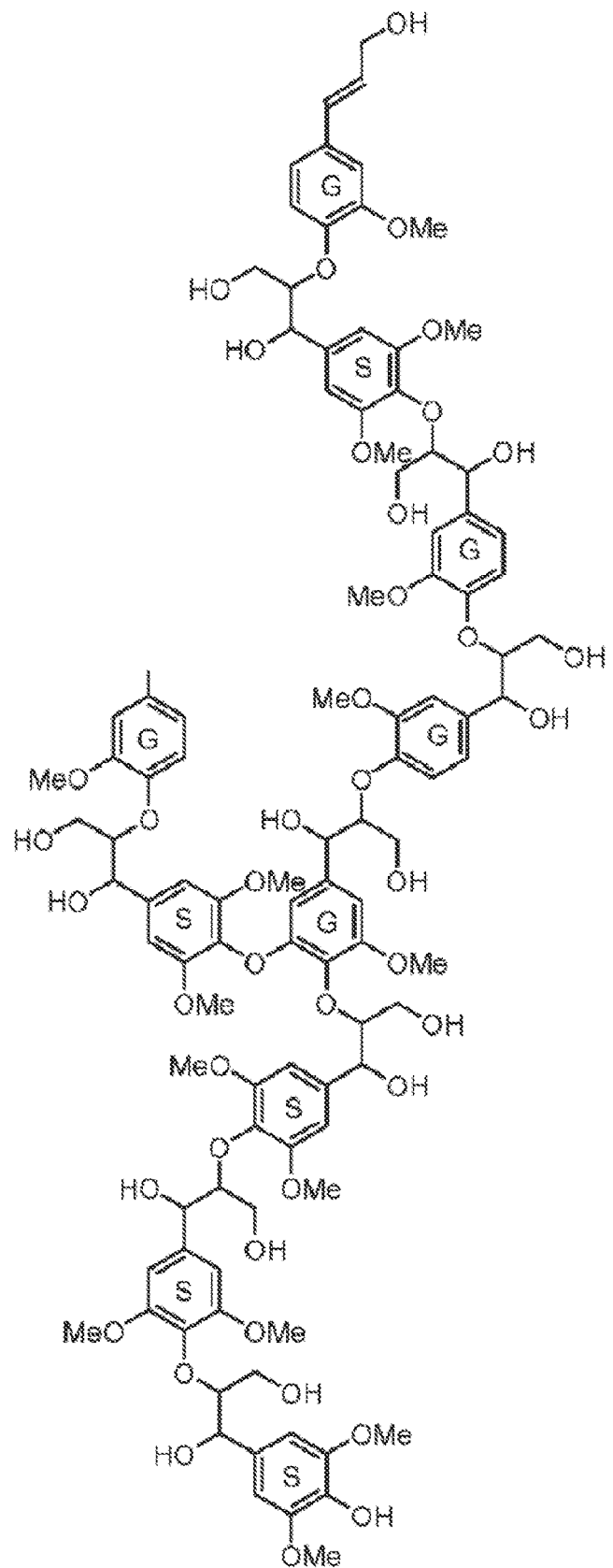
Figure 2A:
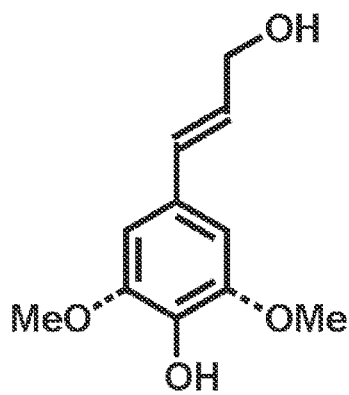
FIGS. 2A-2E show the structures of possible reactants and products of the activity of certain BAHD acyltransferase enzymes of the invention.
Figure 2B:
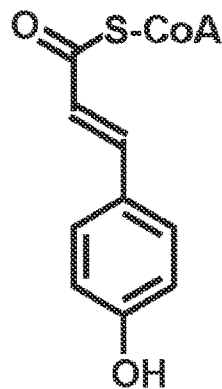
Figure 2C:
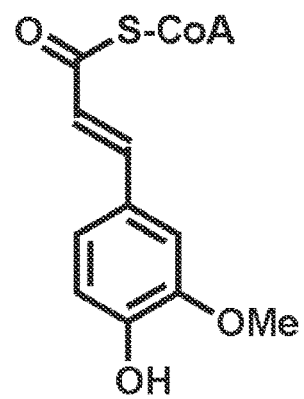
Figure 2D:
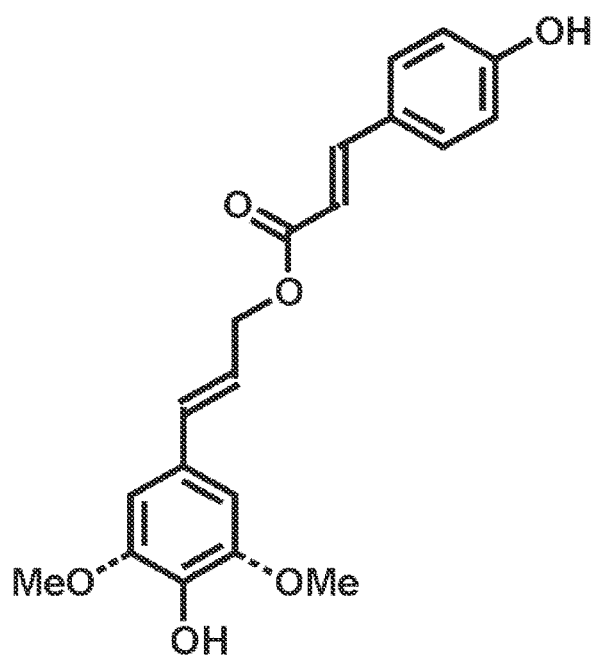
Figure 2E:
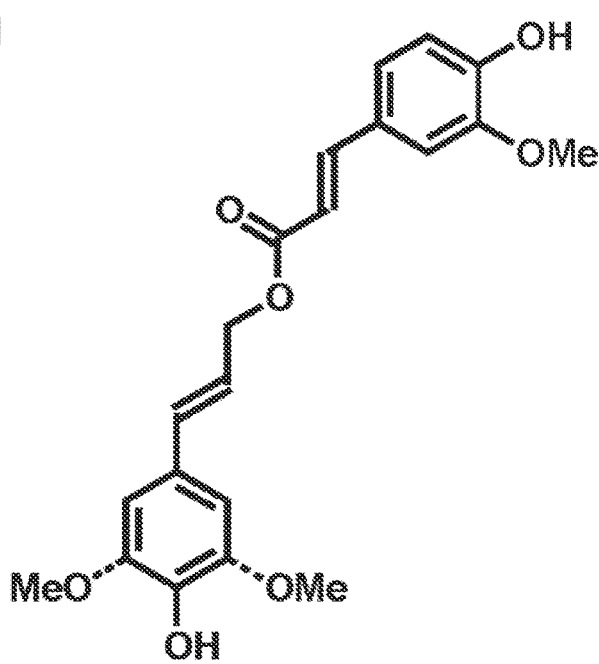

The invention provides nucleic acids and methods useful for altering lignin structure and/or the lignin content in plants. Plants with such altered lignin structure/content are more easily or economically processed into useful products such as biofuels, paper, or commodity chemicals.

Acyl-CoA Dependent Acyltransferases

Plant acyl-CoA dependent acyltransferases constitute a large but specific protein superfamily, named BAHD. Members of this family take an activated carboxylic acid (i.e., a CoA thioester form of the acid) as an acyl donor and either an alcohol or, more rarely, a primary amine, as an acyl acceptor and catalyze the formation of an ester or an amide bond, respectively. The acyl donors and acyl acceptors that act as substrates by BAHD acyltransferases are quite diverse, and different BAHD family members exhibit a range of substrate specificities.

The invention relates to new BAHD acyltransferase nucleic acids and enzymes that enable the production of transgenic plants with altered lignin. The BAHD nucleic acids can be used in the expression cassettes, expression vectors, transgenic plant cells, transgenic plants, and transgenic seeds as described herein.

The BAHD nucleic acids and encoded proteins may be isolated or recombinant nucleic acids or proteins.

The term "isolated" when used in conjunction with a nucleic acid, polypeptide, or cell refers to a nucleic acid segment, polypeptide, or cell that is present in a form or setting that is different from that in which it is found in nature. An example of an isolated nucleic acid, polypeptide, or cell is one that is identified and separated from at least one contaminant nucleic acid, polypeptide, or cell with which it is ordinarily associated in its natural state. An example of an isolated nucleic acid or polypeptide is one that has been removed from its natural or native cell. Thus, the nucleic acid or polypeptide can be physically isolated from the cell or the nucleic acid or polypeptide can be present or maintained in another cell where it is not naturally present or synthesized.

The term "recombinant" when used in reference to a nucleic acid or polypeptide refers to a nucleic acid or polypeptide that has a non-natural nucleotide or amino acid sequence, i.e., a nucleotide or amino acid sequence not found in nature. For example, a recombinant nucleic acid includes a nucleic acid segment from one species that has been introduced into a nucleic acid of another species. A recombinant nucleic acid also includes a nucleic acid segment that is native to an organism but has been altered in some way (e.g., mutated, linked to a heterologous promoter or enhancer sequence, etc.). A recombinant nucleic acid also includes a nucleic acid comprising a combination of genetic elements wherein the combination does not occur in nature. Non-limiting examples of such genetic elements include coding sequences, promoters, enhancers, ribosome binding sites (e.g., Shine Dalgarno sequences, Kozak sequences), etc. The term "heterologous" refers to any such individual genetic element or nucleic acid segment when included in such a non-naturally occurring combination. Recombinant nucleic acids can include codon-optimized coding sequences that are distinct from any coding sequences found in nature. Recombinant nucleic acids include nucleic acid segments comprising one or more differences (i.e., substitutions, deletions, insertions) with respect to any nucleic acid segments found in nature. Recombinant nucleic acids can include nucleic acids such as cDNA forms of a plant gene where the cDNA sequences are expressed in a sense direction to produce mRNA. In some embodiments, recombinant nucleic acids can be distinguished from endogenous plant genes in that heterologous nucleic acid segments are joined to nucleotide sequences comprising regulatory elements such as promoters that are not found naturally associated with the endogenous gene in its natural chromosome. In some embodiments, recombinant nucleic acids can be distinguished from endogenous plant genes in that the recombinant nucleic acids express the encoded protein (or portion of a protein) in parts of the plant where the protein (or portion thereof) is not normally expressed. The term "cDNA" refers to any DNA that includes a coding sequence for a polypeptide and lacks one or more introns present in naturally occurring genomic DNA also comprising that coding sequence, regardless of whether or not the cDNA is directly generated from mRNA.

The term "recombinant" when used in reference to a cell refers to a cell comprising a recombinant nucleic acid or a recombinant polypeptide.

The term "native," when used at least in reference to a nucleic acid or polypeptide, refers to a nucleic acid or polypeptide as it exists in nature. Native nucleic acids or polypeptides include DNA, RNA, or amino acid sequences or segments that have not been manipulated in vitro, i.e., have not been isolated, purified, amplified, and/or recombined in any way.

Feruloyl-CoA:monolignol transferases (FMTs) constitute one type of BAHD acyltransferase. Feruloyl-CoA:monolignol transferases have the activity of catalyzing the acylation of any one or more of three monolignols (e.g., p-coumaryl alcohol, coniferyl alcohol, and/or sinapyl alcohol) with feruloyl-CoA to generate any one or more of three monolignol ferulates (e.g., p-coumaryl ferulate, coniferyl ferulate, and/or sinapyl ferulate). An example of one of these reactions is shown below:

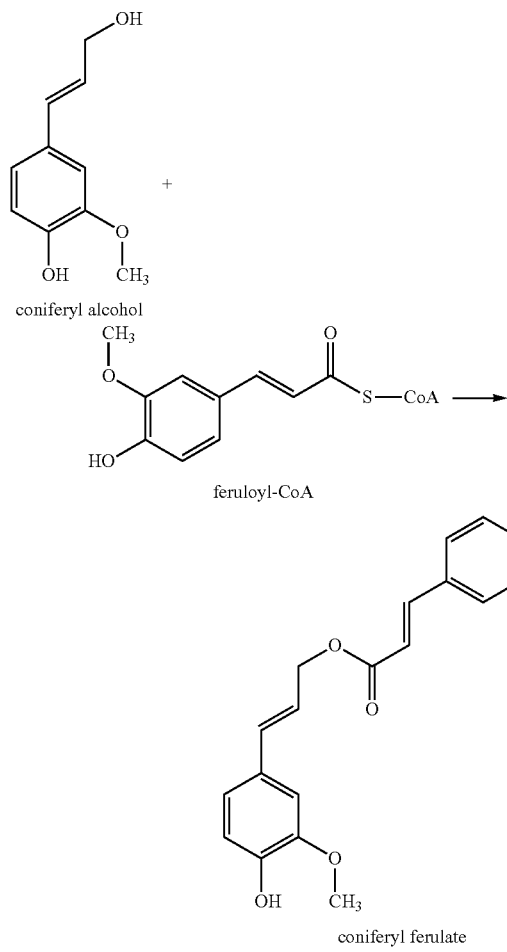

Exemplary feruloyl-CoA:monolignol transferases are described in U.S. Appl. 62/481,281, U.S. Pat. Nos. 9,441,235, 9,487,794, 9,493,783, U.S. Pub. 2015/0020234A1, U.S. Pub. 2015/0307892A1, WO 2012/012698A1, WO 2012/012741A1, and WO 2013/052660A1. The terms "feruloyl-CoA:monolignol transferase(s)," "feruloyl-CoA monolignol transferase(s)," and "monolignol ferulate transferase(s)" are used interchangeably herein.

Feruloyl-CoA:monolignol transferases enable production of plants with lignin that is readily cleaved and/or removed, for example, because the lignin in these plants contains monolignol ferulates such as coniferyl ferulate (CAFA). See Karlen, S. D.; Zhang, C.; Peck, M. L.; Smith, R. A.; Padmakshan, D.; Helmich, K. E.; Free, H. C. A.; Lee, S.; Smith, B. G.; Lu, F.; Sedbrook, J. C.; Sibout, R.; Grabber, J. H.; Runge, T. M.; Mysore, K. S.; Harris, P. J.; Bartley, L. E.; Ralph, J. (2016) Monolignol ferulate conjugates are naturally incorporated into plant lignins. Science Advances, 2(10):e1600393.

p-Coumaroyl-CoA:monolignol transferases (PMTs) constitute another type of BAHD acyltransferase. p-Coumaroyl-CoA:monolignol transferases have the activity of catalyzing the acylation of any one or more of three monolignols (e.g., p-coumaryl alcohol, coniferyl alcohol, and/or sinapyl alcohol) with p-coumaroyl-CoA to generate any one or more of three monolignol p-coumarates (e.g., p-coumaryl p-coumarate, coniferyl p-coumarate, and/or sinapyl p-coumarate). Examples of these reactions are shown below:

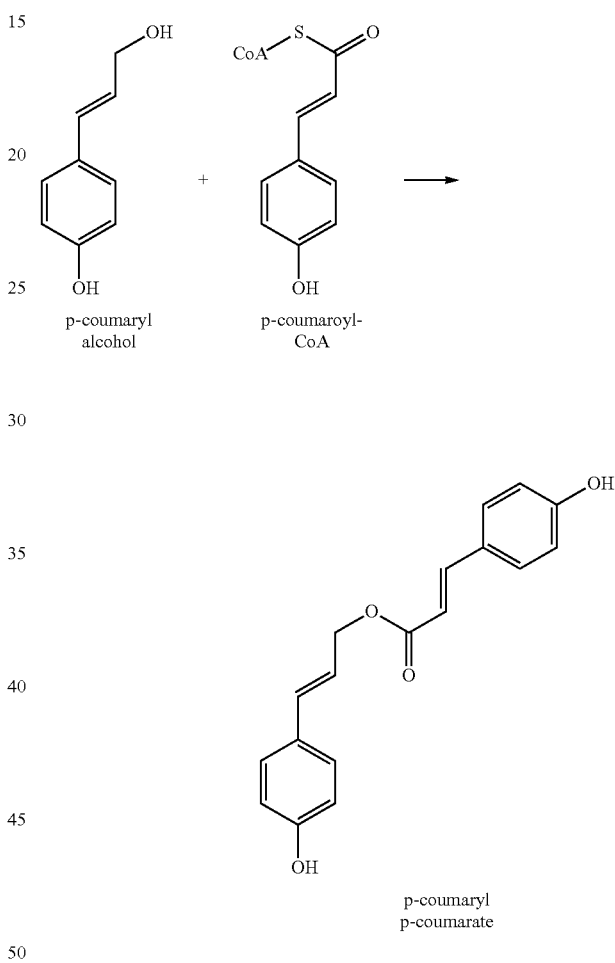

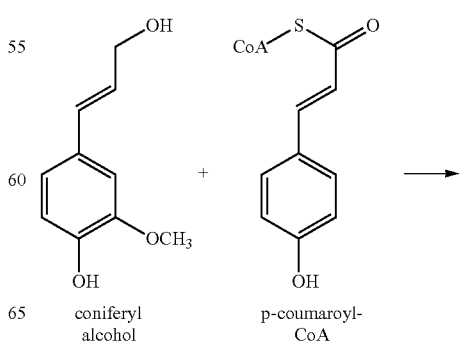

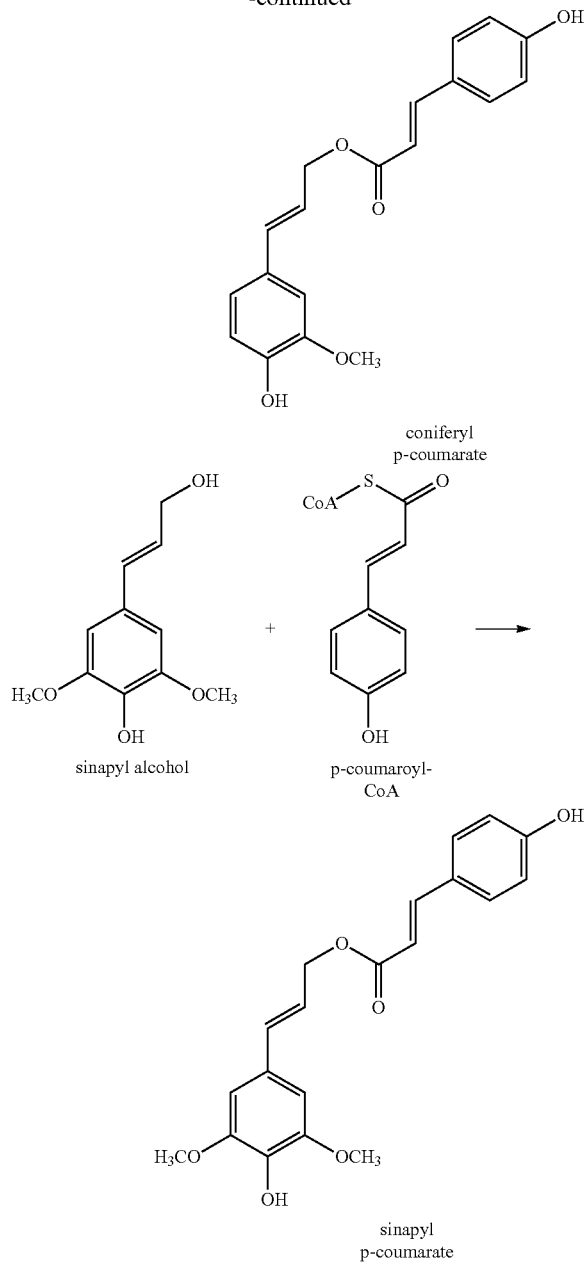

Exemplary p-coumaroyl-CoA:monolignol transferases are described in U.S. Pub. 2018/0298353 and U.S. Pub. 2016/0046955. The terms "p-coumaroyl-CoA:monolignol transferase(s)," "p-coumaroyl-CoA monolignol transferase(s)," and "monolignol p-coumarate transferases" are used interchangeably herein.

p-Hydroxybenzoyl-CoA:monolignol transferases (pBMTs) constitute another type of BAHD acyltransferase. p-Hydroxybenzoyl-CoA:monolignol transferases have the activity of catalyzing the acylation of any one or more of three monolignols (e.g., p-coumaryl alcohol, coniferyl alcohol, and/or sinapyl alcohol) with p-hydroxybenzoyl-CoA (4-hydroxybenzoyl-CoA) to generate any one or more of three monolignol p-hydroxybenzoates (e.g., p-coumaryl p-hydroxybenzoate, coniferyl p-hydroxybenzoate, and/or sinapyl p-hydroxybenzoate). The terms "p-hydroxybenzoyl-CoA:monolignol transferase(s)," "p-hydroxybenzoyl-CoA monolignol transferase(s)," and "monolignol p-hydroxybenzoate transferases" are used interchangeably herein.

Benzoyl-CoA:monolignol transferases (BMTs) constitute another type of BAHD acyltransferase. Benzoyl-CoA:monolignol transferases have the activity of catalyzing the acylation of any one or more of three monolignols (e.g., p-coumaryl alcohol, coniferyl alcohol, and/or sinapyl alcohol) with benzoyl-CoA to generate any one or more of three monolignol benzoates (e.g., p-coumaryl benzoate, coniferyl benzoate, and/or sinapyl benzoate). The terms "benzoyl-CoA:monolignol transferase(s)," "benzoyl-CoA monolignol transferase(s)," and "monolignol benzoate transferases" are used interchangeably herein.

Acetyl-CoA:monolignol transferases (AMTs) constitute another type of BAHD acyltransferase. Acetyl-CoA:monolignol transferases have the activity of catalyzing the acylation of any one or more of three monolignols (e.g., p-coumaryl alcohol, coniferyl alcohol, and/or sinapyl alcohol) with acetyl-CoA to generate any one or more of three monolignol acetates (e.g., p-coumaryl acetate, coniferyl acetate, and/or sinapyl acetate). The terms "acetyl-CoA:monolignol transferase(s)," "acetyl-CoA monolignol transferase(s)," and "monolignol acetate transferases" are used interchangeably herein.

The various types of BAHD acyltransferases are not mutually exclusive of each other. Thus, an enzyme can be both an FMT and a PMT if the enzyme has both FMT and PMT activity.

The term "monolignol ester conjugate" is used herein to refer to a compound or moiety comprising a monolignol group conjugated to an ester group. Exemplary monolignol groups include p-coumaryl, coniferyl, and sinapyl groups. Exemplary ester groups include ferulate, p-coumarate, p-hydroxybenzoate, benzoate, and acetate groups. Exemplary monolignol ester conjugates include monolignol ferulates, monolignol p-coumarates, monolignol p-hydroxybenzoates, monolignol benzoates, and monolignol acetates. Exemplary monolignol ferulates include p-coumaryl ferulate, coniferyl ferulate, and sinapyl ferulate. Exemplary monolignol p-coumarates include p-coumaryl p-coumarate, coniferyl p-coumarate, and sinapyl p-coumarate. Exemplary monolignol p-hydroxybenzoates include p-coumaryl p-hydroxybenzoate, coniferyl p-hydroxybenzoate, and sinapyl p-hydroxybenzoate. Exemplary monolignol benzoates include p-coumaryl benzoate, coniferyl benzoate, and sinapyl benzoate. Exemplary monolignol acetates include p-coumaryl acetate, coniferyl acetate, and/or sinapyl acetate.

An exemplary BAHD acyltransferase of the invention is referred to herein as "XMT1." XMT1 has pBMT, FMT, PMT, AMT, and BMT activity. An exemplary coding sequence for XMT1 comprises SEQ ID NO:1:

```
                                          (SEQ ID NO: 1)
ATGGCAACACCAACTTCCTTATCGTTCGCCGTCCGAAGGTGCGAACCAG

AATTGGTTGCGCCAGCTAAGGCCACACCTCATGAATTCAGACAGCTTTC

TGATATTGATCGCCAACTATACCTCCAATTTCAATCACCACATTACAAC

TTGTATGCACACAATCCATCGATGCAAGGGAAAGATCCTGTGAAGGTAA

TAAAGGAGGCAATTGCGCAGGCACTTGTGTATTATTACCCTTTTGCTGG

TAGGATTAGACAAGGGCCAGACAATAAGCTTATAGTTGATTGTACTGGT

GAGGGTGTCTTGTTCATCGAAGCCGATGCCGATGCCACGGTGGAGCAGT

TTGGTGATCCAATTCCATCTCCATTCCCATGCTTTCAGGAACTTCTTTA
```

```
CAACGTCCCAGGATCAGAAGGGATCCTCAATACCCCATTATTGATTTTT
CAGGTGACACGCTTGAAGTGTGGTGGTTTTGTACTTGGGCTCCGTCTTA
ATCACCCAATGACTGATGCATTCGGCATGCTTCAGGTATTGAATGCCAT
AGGTGAGATTGCACGAGGTGCTCAAGCCCCTTCAATTCTACCTGTGTGG
CGAAGGGAACTCCTCTGTGCTAGGAATCCGCCACGAGTTACTTGCAGAC
ACAATGAATATGGTAATGATGCTCCTGTTGCTGTTGATCCTACAGCCAA
GGTGCCTGAATTCCACGGCCAGGTTCACGCTGTAGCCCACCGTAGTTTT
GTTCTCAACCGCAAGGAATTATCCAACATTCGTAGATGGATTCCTTCTC
ATTTACACCCATGTTCAAATTTTGAGGTAATAACTGCATGCTTATGGAG
ATGCTATGCCATAGCATCTCAAGCTAACCCTAATGAGGAGATGCGCATG
CAAATGCTTGTCAACGCACGTTCCAAATTTAACCCTCCATTACCGAAAG
GATATTATGGTAACGTGCTAGCTTTGCCAGCAGCTGTAACAAATGCTAG
GAAGCTTTGCTTAAACTCTTTAGGGTATGCATTGGAAATGATAAGAAAT
GCCAAGAATAGAATAACTGAGGAGTACATGAGATCATTGGCTGATCTAA
TGGAGATAACCAAAGGGCAGCCTATAGGGTTACAATCATATGTCGTGTC
AGACTTAACAGGTTTTGGGTTCGATCAGGTGGACTATGGATGGGGCAAC
ACAATTTATACTGGGCCACCCAAGGCTATGCCTGATGAAATTTCTATGG
CAGGAACCTATTTCCTGCCGTATCGATTCAAGAACGGAGAGCGTGGGGT
TATGCTTTTGGTTTCCTTACGTGCACCAGTTATGGAGAGATTTGCAATA
CTATTAGAGGAATTGGCAAGGCATGACCCAGAAAGAAGCCAAGAACAAC
AAGAAATGATACCAAGCTCCCTATAA
```

XMT1 comprises an amino acid sequence of SEQ ID NO:2:

```
                                         (SEQ ID NO: 2)
MATPTSLSFAVRRCEPELVAPAKATPHEFRQLSDIDRQLYLQFQSPHYN
LYAHNPSMQGKDPVKVIKEAIAQALVYYYPFAGRIRQGPDNKLIVDCTG
EGVLFIEADADATVEQFGDPIPSPFPCFQELLYNVPGSEGILNTPLLIF
QVTRLKCGGFVLGLRLNHPMTDAFGMLQVLNAIGEIARGAQAPSILPVW
RRELLCARNPPRVTCRHNEYGNDAPVAVDPTAKVPEFHGQVHAVAHRSF
VLNRKELSNIRRWIPSHLHPCSNFEVITACLWRCYAIASQANPNEEMRM
QMLVNARSKFNPPLPKGYYGNVLALPAAVTNARKLCLNSLGYALEMIRN
AKNRITEEYMRSLADLMEITKGQPIGLQSYVVSDLTGFGFDQVDYGWGN
TIYTGPPKAMPDEISMAGTYFLPYRFKNGERGVMLLVSLRAPVMERFAI
LLEELARHDPERSQEQQEMIPSSL
```

Another exemplary BAHD acyltransferase of the invention is referred to herein as "XMT2." XMT2 has pBMT, AMT, and BMT activity. An exemplary coding sequence for XMT2 comprises SEQ ID NO:3:

```
                                         (SEQ ID NO: 3)
ATGGCAACACCAACTTCCATATCGTTCGCCGTCCGAAGGTGCGAACCAG
AATTGGTTGCGCCAGCTAAGGCCACACCTCATGAATTCAGACAGCTTTC
TGATATTGATCGCCAACTATACCTCCAATTTCAATCACCACATTACAAC
TTGTATGCACACAATCCATCGATGCAAGGGAAAGATCCTGTGAAGGTAA
TAAAGGAGGCAATTGCGCAGGCACTTGTGTATTATTACCCTTTTGCTGG
TAGGATTAGACAAGGGCCAGACAATAAGCTTATAGTTGATTGTACTGGT
GAGGGTGTCTTGTTCATCGAAGCCGATGCCGATGCCACGGTGGAGCAGT
TTGGTGATCCAATTCCATCTCCATTCCCATGCTTTCAGGAACTTCTTTA
CAACGTCCCAGGATCAGAAGGGATCCTCAATACCCCATTATTGATTTTT
CAGGTGACACGCTTGAAGTGTGGCGGTTTTGTACTTGGGTTCCGTCTTA
ATCACCCAATGACCGATGCACTCGGCATAGTTCAGCTATTGAATGCCAT
AGGTGAGATTGCACGAGGTGCCCAAGCCCCTTCAATTCTACCTGTGTGG
CAAAGGGAACTCCTCTGTGCTAGGAATCCGCCACGAGTTACATGCAGAC
ACAATGAATATGGTAATGATGCTCCTGTTGCTGTTGATCCTACAGCCAA
GGTGCCTGAATTCCACGGCCAGGTTCACGCTGTAGCCCACCGTAGTTTT
GTTCTCAACCGCAAGGAATTATCCAACATTCGTAGATGGATTCCTTCTC
ATTTACACCCATGTTCAAATTTTGAGGTAATAAGTGCATGCTTATGGAG
ATGCTATGCCATGCATCTCAAGCTAACCCTAATGAGGAGATGCGCATG
CAAATGCTTGTTAACGCACGTTCCAAATTTAACCCTCCATTACCGAAAG
GATATTATGGTAACGTGCTAGCTTTGCCAGCAGCTGTAACAAATGCTAG
GAAGCTTTGCTTAAACTCTTTAGGGTATGCTGTGGAAATGATAAGAAAT
GCCAAGAATAGAATAACTGAGGAGTACATGAGATCATTGGCTGATCTAA
TGGAGATAACCAAAGGGCAGCCTATAGGGTTACAATCATATGTCGTGTC
AGACTTAACAAGTATTGGGTTCGATCAGGTGGACTATGGATGGGGCAAC
ACAATTTACACTGGGCCACCCAAGGCCATGCCTGATGAAATTTCTATTG
CAGGAACCTATTTCCTGCCGTATCGATTCAAGAACGGAGAGCGTGGGGT
TATGCTTTTGGTTTCCTTACGTGCACCAGTTATGGAGAGATTTGCAATA
CTATTAGAGGAATTGGCAAGGCATGACCCAGAAAGAAGCCAAGAACAAC
AAGAAATGATACCAAGCTCCCTATAA
```

XMT2 comprises an amino acid sequence of SEQ ID NO:4:

```
                                         (SEQ ID NO: 4)
MATPTSISFAVRRCEPELVAPAKATPHEFRQLSDIDRQLYLQFQSPHYN
LYAHNPSMQGKDPVKVIKEAIAQALVYYYPFAGRIRQGPDNKLIVDCTG
EGVLFIEADADATVEQFGDPIPSPFPCFQELLYNVPGSEGILNTPLLIF
QVTRLKCGGFVLGFRLNHPMTDALGIVQLLNAIGEIARGAQAPSILPVW
QRELLCARNPPRVTCRHNEYGNDAPVAVDPTAKVPEFHGQVHAVAHRSF
VLNRKELSNIRRWIPSHLHPCSNFEVISACLWRCYAMASQANPNEEMRM
QMLVNARSKFNPPLPKGYYGNVLALPAAVTNARKLCLNSLGYAVEMIRN
AKNRITEEYMRSLADLMEITKGQPIGLQSYVVSDLTSIGFDQVDYGWGN
TIYTGPPKAMPDEISIAGTYFLPYRFKNGERGVMLLVSLRAPVMERFAI
LLEELARHDPERSQEQQEMIPSSL
```

Another exemplary BAHD acyltransferase of the invention is referred to herein as "XMT3." XMT3 has pBMT, AMT, and BMT activity. An exemplary coding sequence for XMT3 comprises SEQ ID NO:5:

(SEQ ID NO: 5)
ATGGCAACACCACCTTCCTTATCGTTCGCCGTCCGAAGGTGCGAACCAG
AATTGATTGCTCCAGCTAAGGCCACACCTCATGAATTCAGACAGCTTTC
TGATATTGATCGACAACTATACCTCCAATTTCAATCACCACATTACAAC
TTGTATGCACACAATCCATCGATGCAAGGGAAAGATCCTGTGAAGGTAA
TAAAGGAGGCAATTGCGCAGGCACTTGTGTATTATTACCCTTTTGCTGG
TAGGATTAGACAAGGGCCAGACAATAAGCTTATAGTTGATTGTACTGGT
GAGGGTGTCTTGTTCATCGAAGCCGATGCCGATGCCACGGTCGAGCAGT
TTGGTGATCCAATTCCATCTCCATTCCCATGTTTTCAGGAACTTCTTTA
CAACGTCCCAGGATCAGAAGGGATCCTCAATACCCCATTATTGCTTTTT
CAGGTGACACGCTTGAAGTGTGGCGGTTTTGTACTTGGGTTCCGTCTTA
ATCACCCAATGACCGATGCACTCGGCATAGTTCAGCTATTGAATGCCAT
AGGTGAGATTGCACGAGGTGCCCAAGCCCCTTCAATTCTACCTGTGTGG
CAAAGGGAACTCCTCTGTGCTAGGAATCCGCCACGAGTTACATGCAGAC
ACAATGAATATGGTAATGATGCTCCTGTTGCTGTTGATCCTACAGCCAA
GGTGCCTGAATTCCACGGCCAGGTTCACGCTGTAGCCCACCGTAGTTTT
GTTCTCAACCGCAAGGAATTATCCAACATTCGTAGATGGATTCCTTCTC
ATTTACACCCATGTTCAAATTTTGAGGTAATAAGTGCATGCTTATGGAG
ATGCTATGCCATGGCATCTCAAGCTAACCCTAATGAGGAGATGCGCATG
CAAATGCTTGTTAACGCACGTTCCAAATTTAACCCTCCATTACCGAAAG
GATATTATGGTAACGTGCTAGCTTTGCCAGCAGCTGTAACAAATGCTAG
GAAGCTTTGCTTAAACTCTTTAGGGTATGCTGTGGAAATGATAAGAAAT
GCCAAGAATAGAATAACTGAGGAGTACATGAGATCATTGGCTGATCTAA
TGGAGATAACCAAAGGGCAGCCTATAGGGTTACAATCATATGTCGTGTC
AGACTTAACAAGTATTGGGTTCGATCAGGTGGACTATGGATGGGGCAAC
ACAATTTACACTGGGCCACCCAAGGCCATGCCTGATGAAATTTCTATTG
CAGGAACCTATTTCCTGCCGTATCGATTCAAGAACGGAGAGCGTGGGGT
TATGCTTTTGGTTTCCTTACGTGCACCAGTTATGGAGAGATTTGCAATA
CTATTAGAGGAATTGGCAAGGCATGACCCAGAAAGAAGCCAAGAACAAC
AAGAAATGATACCAAGCTCCCTATAA

XMT3 comprises an amino acid sequence of SEQ ID NO:6:

(SEQ ID NO: 6)
MATPPSLSFAVRRCEPELIAPAKATPHEFRQLSDIDRQLYLQFQSPHYN
LYAHNPSMQGKDPVKVIKEAIAQALVYYYPFAGRIRQGPDNKLIVDCTG
EGVLFIEADADATVEQFGDPIPSPFPCFQELLYNVPGSEGILNTPLLLF
QVTRLKCGGFVLGFRLNHPMTDALGIVQLLNAIGEIARGAQAPSILPVW
QRELLCARNPPRVTCRHNEYGNDAPVAVDPTAKVPEFHGQVHAVAHRSF
VLNRKELSNIRRWIPSHLHPCSNFEVISACLWRCYAMASQANPNEEMRM
QMLVNARSKFNPPLPKGYYGNVLALPAAVTNARKLCLNSLGYAVEMIRN
AKNRITEEYMRSLADLMEITKGQPIGLQSYVVSDLTSIGFDQVDYGWGN
TIYTGPPKAMPDEISIAGTYFLPYRFKNGERGVMLLVSLRAPVMERFAI
LLEELARHDPERSQEQQEMIPSSL

Another exemplary BAHD acyltransferase of the invention is referred to herein as "XMT4." XMT4 has FMT, PMT, and BMT activity. An exemplary coding sequence for XMT4 comprises SEQ ID NO:7:

(SEQ ID NO: 7)
ATGGCAACACCAACTTCGATATCGTTCGCAGTCCGAAGGTGCGAACCAG
AATTGGTCGCACCAGCTAAGGCCACACCTCATGAATTCAGACAGCTTTC
TGATATTGATCGCCAACTATACCTCCAATTTCAATCACCAGGTTACAAC
TTGTATGCACACAATCCATCGATGCAAGGGAAAGATCCTGTGAAGGTAA
TAAAGGAGGCAATTGCGCAGGCACTTGTGTATTATTACCCTTTTGCTGG
TAGGATTAGACAAGGGCCAGACAATAAGCTTATAGTTGATTGTACTGGT
GAGGGTGTCTTGTTCATCGAAGCTGATGCCGATGCCACGGTCGAGCAGT
TTGGTGATCCAATTCCATCTCCATTCCCATGCTTTCAGGAACTTCTTTA
CAACGTCCCAGGATCAGAAGAGATCCTCAATACCCCATTATTGCTTTTT
CAGGTGACACGCTTGAAGTGTGGTGGTTTTGTACTTGGGCTCCGTTTTA
ATCACCTAATGAGTGATGGACTCGGCATGCTTCAGTTATTTAATACCAT
AGGTGAGATGGCACGAGGTGCTCAAACCCCTTCAATTCTACCTGTGTGG
CAAAGGGAACTCCTCTGTGCTAGGAATCCGCCACGAGTTACATGCAGAC
ACAATGAATATGGTGATGATGCTCCTGTTGCTGTTGATCCTACAGCCAA
GGTGCCTGAATTCCGCGGCGAGGTTCACGCTGTAGCCCACCGTAGTTTT
GTTCTTAACCGCAAGGAATTATCCAACATTCGTAGATGGGTTCCTTCTC
ATTTACACCCATGTTCAGATTTTGAGGTAATAAGTGCATGCTTATGGAG
ATGCTATGCCATAGCATCTCAAGCTAACCCTAATGAGGAGATGCGCATG
CAAATGCTTGTCAACGCACGTTCCAAATTTAACCCTCCATTACCGAAAG
GATATTATGGTAACGTGCTAGCTTTGCCAGCAGCTGTAACAAATGCTAG
GAAGCTTTGCTTAAACTCTTTAGGGTATGCATTGGAAATGATAAGAAAT
GCCAAGAATAGAATAACTGAGGAGTACATGAGATCATTGGCTGATCTGA
TGGAGATAACCAAAGGGCAGCCTATAGCGTTACAATCATATGTCGTGTC
AGACTTAACAAGTTTTGGGTTCGATCAGGTGGACTATGGATGGGGCAAC
ACAATTTACTCTGGGCCACCTAAGGCTATGCCGGATGAAATTTCTATTG
CAGGAACCTTTGTCCTGCCGTATCGATTCAAGAACGGAGAGCGTGGGGT
TATGGTTTTGGTTTCCTTACGTGCACCAGTTATGGAGAGATTTGCAATA
CTATTAGAGGAATTGGCAAGGCATGACCCAGAAAGAAGCCAAGGACAAC
AAGAAATGATACCAAGCTCCCTATAA

XMT4 comprises an amino acid sequence of SEQ ID NO:8:

(SEQ ID NO: 8)
MATPTSISFAVRRCEPELVAPAKATPHEFRQLSDIDRQLYLQFQSPGYN

LYAHNPSMQGKDPVKVIKEAIAQALVYYYPFAGRIRQGPDNKLIVDCTG

EGVLFIEADADATVEQFGDPIPSPFPCFQELLYNVPGSEEILNTPLLLF

QVTRLKCGGFVLGLRFNHLMSDGLGMLQLFNTIGEMARGAQTPSILPVW

QRELLCARNPPRVTCRHNEYGDDAPVAVDPTAKVPEFRGEVHAVAHRSF

VLNRKELSNIRRWVPSHLHPCSDFEVISACLWRCYAIASQANPNEEMRM

QMLVNARSKFNPPLPKGYYGNVLALPAAVTNARKLCLNSLGYALEMIRN

AKNRITEEYMRSLADLMEITKGQPIALQSYVVSDLTSFGFDQVDYGWGN

TIYSGPPKAMPDEISIAGTFVLPYRFKNGERGVMVLVSLRAPVMERFAI

LLEELARHDPERSQGQQEMIPSSL

A putative BAHD acyltransferase is referred to herein as "XMT5." An exemplary coding sequence for XMT5 comprises SEQ ID NO:9:

(SEQ ID NO: 9)
ATGGCAGCATCTACTCCCTTATCATTTGCGGTCCGACGATGCGAACCTG

AATTGGTTGCCCCAGCTAAAGCCACTCCTCATGAACTCAGACAGCTTTC

TGATATTGATCGCCAATTATACCTCCAATTCCAATCACCGAATTACAAC

TTGTATGCACACAATCCCTCAATGCAAGGGAAAGATCCCGTGAAGGTAA

TAAAAGAGGCGATTGCACAAACACTTGTTTATTATTACCCTTTTGCTGG

TAGGATTAGACAAGGGCCAGACAATAAGCTTATAGTTGAATGTACTGGG

GAGGGTGTTTTGTTCATCGAAGCCGATGCCGATGCTACAGTTGAGCAGT

TTGGTGATCCAATTCCATCTCCATTCCCTTGCTTTGAAGAACTTCTATA

CAACGTCCCAGGATCTGCAGGGATCCACAATACCCCATTATTGTCTTTT

CAGGTGACACGCTTGAAGTGTGGTGGTTTTGTACTTGCCTATCGTCGA

ATCACCTAATGAGTGATGCTCTTGGCATAGTTCAGCTATTGAGTGCCAT

AGGGGAGATTGCACGAGGTGCGCAAGCCCCTTCAATTCTACCTGTGTGG

CAAAGGGAACTTCTCTGTGCTAGGAATCCACCACGCGTTACTCGCAGAC

ACAGTGAATATGGTAATGATGGTCCAGTTGTTGTTGGTCCTACAACCAA

CGTTCCTGAATTCCACGGCGAAGTTTACGATGTAGCCCACCGTAGTTTC

GTTCTTAACCGCAAAGAATTATCAAACATTCGTAGATGGATTCCTTCTC

ATTTACACCCTTGTTCAAATTTTGAGGTCATAAGTGCATGCTTATGGAG

ATGCTATGCCATAGCATCTCAAGCAAACCCTAATGAGCAGATGCGCATG

CAATTGCTTGTCAATGCACGTTCCAAGTTCAACCCACCATTACCAAAAG

GATATTACGGTAACGTGCTAGCTTTGCCAGCAGCTGTAACAAATGCTAA

GAACCTTTGTTTAAACTCATTAGGGTATGCAATGGAGTTGATAAGGAAT

GCCAAGAATGCAATAACTGAGGAGTACATGAGATCATTGGCTGATCTAA

TAGAGATCACCAAAGGCCAGCCTATCGGGTTACAGTCATATGTTGTGTC

AGACATAACAAGTATTGGGTTTGATCAAGTGGATTGTGGGTGGGATAAG

CCAGTTTATGCTGGGCCAGCTAAGGCCATGCCTGATGAAATTTCTATTG

CTGGAACCTATTTTCTGCCCTATAGATTCAAGAACGGAGAGCGAGGGGT

TATGCTGTTAGTTTCCTTACGCGCACCAGTTATGGAGAGATTTGCAGTC

CTCTTAGAGGAATTGGCAAGGAATGATCCAGAAAGAAGCCAAGGACAAC

AAGAAATGATACTAAGCTCCCTTTAA

XMT5 comprises an amino acid sequence of SEQ ID NO:10:

(SEQ ID NO: 10)
MAASTPLSFAVRRCEPELVAPAKATPHELRQLSDIDRQLYLQFQSPNYN

LYAHNPSMQGKDPVKVIKEAIAQTLVYYYPFAGRIRQGPDNKLIVECTG

EGVLFIEADADATVEQFGDPIPSPFPCFEELLYNVPGSAGIHNTPLLSF

QVTRLKCGGFVLAYRLNHLMSDALGIVQLLSAIGEIARGAQAPSILPVW

QRELLCARNPPRVTRRHSEYGNDGPVVVGPTTNVPEFHGEVYDVAHRSF

VLNRKELSNIRRWIPSHLHPCSNFEVISACLWRCYAIASQANPNEQMRM

QLLVNARSKFNPPLPKGYYGNVLALPAAVTNAKNLCLNSLGYAMELIRN

AKNAITEEYMRSLADLIEITKGQPIGLQSYVVSDITSIGFDQVDCGWDK

PVYAGPAKAMPDEISIAGTYFLPYRFKNGERGVMLLVSLRAPVMERFAV

LLEELARNDPERSQGQQEMILSSL

Another exemplary BAHD acyltransferase of the invention is referred to herein as "XMT6." XMT6 has pBMT activity. An exemplary coding sequence for XMT6 comprises SEQ ID NO:11:

(SEQ ID NO: 11)
ATGCCAACTCCTACTTCCTTAGCATTCAATGTGCGAAGGTGCGAGCCAG

AATTGGTTGCACCAGCTAAAGCCACACCCCATGAATCCAAACCACTTTC

TGATATCGATCGCCAACTATACCTACAATTTCAATCACCACATTACAAC

TTTTATGCACACAACCCGTCCATGCAAGGGAAAGATCCTGTGAAGGTAA

TAAGAGAGGGAATTGCTCAGGCACTTGTGTATTATTATCCTTATGCCGG

GAGGATTAGACAAGAGCCAGAAAATAAGCTTGTAGTAGATTGTACAGGA

GAGGGTGTCTTGTTCATTGAAGCTGATGCTGATGGCACACTGGAGCAGT

TTGGTGATCCAATTCAGCCTCCGTTCCCTTGTGCTGAGGAACTTCTTTA

CAATGTCCCAGGGTCAGCAGGAATCATCAATACCCCGTTGCTGATCATT

CAGATAACACGCTTGAAGTGTGGTGGTTTTATACTTGGCTTCCGTCTTA

ATCACCCAATGAGTGATGCCATTGGCCTAGTTCAGCTATTGAGTGCCAT

AGGTGAGATCTCACGAGGTGCTCAAGCCCCTTCAATTCTACCTGTGTGG

CAAAGAGAACTCCTTTGTGCTAGGAATCCACCTCGTGTTACTTGCACAC

ACAACGAATATGGCGATCATCATGATCTTGTTGTGGATCCTAGCGAGCT

CAACGTTCCTGAATTTCGGGGTAGCACTGACGGTGCAGCCCACCGTTGT

TTCATCATCGGCCCTAAAGAATTATCCAACATTCGTAAATGGATTCCTC

CTCATTTACACCCATGTTCCAAGTTTGAAATAATAACCGCATGCTTATG

GAGATGCCATGCCATAGCATCTCAAGCAAACCCTAATGAGGAGATGCGC

ATTTGTATGCTCGTCAATGCACGTTCCAAATTCAACCCTCCGTTACCAA

AGGGTTATTATGGTAACGTGCTGGCATTGCCAGCAGCTATAACCAGTGC

```
TAGGAAGCTTTGTTTGAACTCATTAGGGTATGCTCTGGAGCTGATAAGG

CAAGCCAAGAACAAGATCACTGAGGAGTACATAAGATCGTTGGCCGATT

TCATTGAGATTACCAAGGGCCTGCCTAAGGGGTTACAGTCATATGTTGT

GTCAGATTTAACAAGTGTTGGGTTCGATCAGGTGGATTATGGTTGGGGT

AAGCCAGTTTATACCGGGCCATCTAAGGCTATGCCTGATGACATTAATA

ATTCTGGAACCTATTACTTACCCTATAGAAACAAGAAAGGAGAGCGTGG

AGTCATGGTTCTGATCTCCTTGCGTGCACCAGTTATGGCAAGATTTGCA

ATGCTATTCGAGGAGTTGACCAAGCACGATCCAGATAGTGGTCCAGCAC

AACACCACACTACTCTCCCTATAAGACACAGGCTTTGA
```

XMT6 comprises an amino acid sequence of SEQ ID NO:12:

```
                                        (SEQ ID NO: 12)
MPTPTSLAFNVRRCEPELVAPAKATPHESKPLSDIDRQLYLQFQSPHYN

FYAHNPSMQGKDPVKVIREGIAQALVYYYPYAGRIRQEPENKLVVDCTG

EGVLFIEADADGTLEQFGDPIQPPFPCAEELLYNVPGSAGIINTPLLII

QITRLKCGGFILGFRLNHPMSDAIGLVQLLSAIGEISRGAQAPSILPVW

QRELLCARNPPRVTCTHNEYGDHHDLVVDPSELNVPEFRGSTDGAAHRC

FIIGPKELSNIRKWIPPHLHPCSKFEIITACLWRCHAIASQANPNEEMR

ICMLVNARSKFNPPLPKGYYGNVLALPAAITSARKLCLNSLGYALELIR

QAKNKITEEYIRSLADFIEITKGLPKGLQSYVVSDLTSVGFDQVDYGWG

KPVYTGPSKAMPDDINNSGTYYLPYRNKKGERGVMVLISLRAPVMARFA

MLFEELTKHDPDSGPAQHHTTLPIRHRL
```

Another exemplary BAHD acyltransferase of the invention is referred to herein as "XMT7." XMT7 has FMT and PMT activity. An exemplary coding sequence for XMT7 comprises SEQ ID NO:13:

```
                                        (SEQ ID NO: 13)
ATGGCAGATGGTAGTAACGATGCTTTAAAACTTACTGTTAAGCAAGGAG

AACCGACTCTGGTTCCTCCAGCAGAGGAGACAAAGAAGGGCCTGTACTT

TCTCTCAAACCTTGATCAAAATATCGCAGTCATAGTTCGTACAATTTAC

TGCTTTAAGTCTGACGTGAAAGGAAATGAGGATGCTGTGGAAGTCATTA

AGAATGCCTTGTCAAAAATTCTTGTGCACTACTATCCAATAGCTGGGCG

GCTAACAATTAGCTCAAAAGGAAAGCTGATAGTGGATTGCACCGGGGAA

GGTGCTGTTTTTGTTGAGGCTGAAACGGATTGTGAAATAGCCGAGCTTG

GAGACATAACAAAACCTGATCCTGTGACTCTTGGGAAGTTGGTTTATGA

AATTCCTGGTGCACAAAACATACTTCAGATGCCTCCTGTAACGGCTCAG

GTGACTAAATTCAAATGTGGAGGATTTGTTCTTGGGCTATGCACGAACC

ATTGTATGTTCGATGGAATTGGTGCTATGGAGTTTGTGAATTCATGGGG

AGCTACTGCTAGGGGTTTGGCTCTTGATGTACCTCCATTTCTAGATAGA

AGCATACTCAAAGCTCGAATCCCGCCTAAGATAGAGTTTCCACACCATG

AATTTGATGACATTGAAGATGTGTCAAATACCAGCAAGCTTTATGAAGA

GGAAATGCTCTATAGATCTTTCTGTTTTGACCCCGAGAAACTTGATCAA

CTCAAGGAAAAAGCTATGGAAGACGGAGTTATAGCCAAGTGCACAACAT

TTCAAGTTCTCTCAGCCTTTGTGTGGAGAGCTCGATGCCAGGCATTGAA

GATGGTGCCTGATCAACAGATAAAGCTCCTGTTTGCTGCAGATGGACGG

TCTAGATTTGAGCCACCAATTCCTGAAGGATACTTTGGCAATGCGATCG

TGTTAACAAATTCTCTGTGCACAGCAGGAGAGATAATGGAAAACCAGTT

GTCCTTTGCTGTAAGGCTAGTTCAGGAGGCAGTTAAAATGGTTGATGAC

AGTTATATGAGATCAGCGATAGATTATTTTGAAGTTACAAGAGCCAGGC

CCTCTCTGACTGCAACTCTTCTAATCACAACTTGGTCTAGGCTATCTTT

CCACACAACAGACTTCGGATGGGGGTGCCTATTTTATCAGGGCCTGTG

GCTCTACCAGAGAAGGAAGTAATTCTCTTCCTTTCTCATGGGATTGAGA

GGAAAAACATAAACGTTCTCGTAGGCCTGCCAGCTTCTTCCATGAAGAT

ATTTGAAGAACTAATGCAGATTTGA
```

XMT7 comprises an amino acid sequence of SEQ ID NO:14:

```
                                        (SEQ ID NO: 14)
MADGSNDALKLTVKQGEPTLVPPAEETKKGLYFLSNLDQNIAVIVRTIY

CFKSDVKGNEDAVEVIKNALSKILVHYYPIAGRLTISSKGKLIVDCTGE

GAVFVEAETDCEIAELGDITKPDPVTLGKLVYEIPGAQNILQMPPVTAQ

VTKFKCGGFVLGLCTNHCMFDGIGAMEFVNSWGATARGLALDVPPFLDR

SILKARIPPKIEFPHHEFDDIEDVSNTSKLYEEEMLYRSFCFDPEKLDQ

LKEKAMEDGVIAKCTTFQVLSAFVWRARCQALKMVPDQQIKLLFAADGR

SRFEPPIPEGYFGNAIVLTNSLCTAGEIMENQLSFAVRLVQEAVKMVDD

SYMRSAIDYFEVTRARPSLTATLLITTWSRLSFHTTDFGWGVPILSGPV

ALPEKEVILFLSHGIERKNINVLVGLPASSMKIFEELMQI
```

Another exemplary BAHD acyltransferase of the invention is referred to herein as "XMT8." XMT8 has FMT and PMT activity. An exemplary coding sequence for XMT8 comprises SEQ ID NO:15:

```
                                        (SEQ ID NO: 15)
ATGGGTATAGAGGCTGAAAAGTTTTCTGCAATGGAGTACTCTAATGGCA

ATGTATTTCAACTAGTTGTGAAACAAGGAGAGCCAACTCTTGTTCCTCC

AGCCGAGGAGACAGAGAAGGGTCTTTACTTTCTCTCCAACCTTGACCAA

AACATTGCAGTGATTGTGCGTACAATCTACTGCTTCAAGTCAGAAGAGA

AAGGAAATGAAAATGCTGGAGAAGTGATCAAGAATGCCTTGAAAAAGGT

TCTTGTGCACTACTATCCTCTTGCCGGGCGGCTAACAATAAGCTCAGAG

GCAAAGCTTATTATAAATTGCACTGGAGAAGGTGCTGTTTTTGTTGAGG

CTGAAGCAAACTGTGCACTGGAAGAGATTGGTGACATAACAAAGCCCGA

TCCAGACACTCTTGGGAAGCTGGTTTATGACATTCCTGGTGCAAAGAAC

ATACTGGAGATGCCTCCTTTGGTGGCTCAGGTCACCAAGTTCACATGTG

GAGGATTTGCACTAGGATTGTGCATGAATCATTGTATGTTTGATGGCAT

TGGTGCTATGGAATTTGTGAACTCATGGGGTGAAACAGCCAGAGGCTTG
```

-continued

```
CCACTCTGTGTCCCTCCATTCATTGACAGAAGCATACTTAAAGCCCGGA

ACCCTCCAAAGATTGAGTACCCCCACCAAGAATTCGCCGAGATAAAAGA

CAAGTCCAGCACAAATGACCTTTACAAAGATGAAATGCTCTACAGCTCC

TTCTGTTTCGATTCTGAAATGCTTGAAAAGATCAAAATGAAAGCCATGG

AAGATGGGGTTCTTGGAAAGTGCACTACTTTTGAAGGGCTCTCAGCTTT

TGTATGGAGAGCTCGAACCAAGGCACTCAAAATGCTGCCTGATCAACAA

ACAAAGCTCCTATTTGCTGTCGATGGAAGGCCAAAATTTAAACCCCCCC

TACCAAAAGGGTACTTCGGAAATGGAATTGTGTTGACCAATTCGATGTG

CCAAGCAGGGGAACTACTAGACAGGCCACTATCACATGCAGTGGGGCTT

GTTCAAGATGCAATTAAAATGGTCACAGACAGTTACATGAGATCTGCTA

TGGATTATTTTGAAGCAACAAGAGTTAGGCCTTCTCTGGCTTCGACTCT

ACTGATAACAACTTGGTCTAGGCTATCTTTCTACACTACAGATTTTGGG

TGGGGAGAGCCAGTTCTATCTGGGCCAGTGGCATTACCAGAGAAGGAAG

TCATCCTGTTCCTATCTCATGGCAAAGAGAGAAAAAGCATAAATGTGCT

TCTGGGTCTGCCAGCTTTAGCCATGAAGACCTTCCAAGAAATGATACAG

ATTTAG
```

XMT8 comprises an amino acid sequence of SEQ ID NO:16:

```
(SEQ ID NO: 16)
MGIEAEKFSAMEYSNGNVFQLVVKQGEPTLVPPAEETEKGLYFLSNLDQ

NIAVIVRTIYCFKSEEKGNENAGEVIKNALKKVLVHYYPLAGRLTISSE

AKLIINCTGEGAVFVEAEANCALEEIGDITKPDPDTLGKLVYDIPGAKN

ILEMPPLVAQVTKFTCGGFALGLCMNHCMFDGIGAMEFVNSWGETARGL

PLCVPPFIDRSILKARNPPKIEYPHQEFAEIKDKSSTNDLYKDEMLYSS

FCFDSEMLEKIKMKAMEDGVLGKCTTFEGLSAFVWRARTKALKMLPDQQ

TKLLFAVDGRPKFKPPLPKGYFGNGIVLTNSMCQAGELLDRPLSHAVGL

VQDAIKMVTDSYMRSAMDYFEATRVRPSLASTLLITTWSRLSFYTTDFG

WGEPVLSGPVALPEKEVILFLSHGKERKSINVLLGLPALAMKTFQEMIQ

I
```

Another exemplary BAHD acyltransferase of the invention is referred to herein as "XMT9." XMT9 has FMT activity. An exemplary coding sequence for XMT9 comprises SEQ ID NO:17:

```
(SEQ ID NO: 17)
ATGGAAGGAACGGGAAAACATGGAGGTGACCAGCTTTCAGTTAAGAAGT

CAGAACCCGTTCTAATAGAACCTGAAACAAGGACTCATAGTGGGTTTTT

TTTCTTATGCAATCTTGATCACATGGTCACTCATTCCGTGGAAACAGTG

TACTTCTACAAGGCAAAGAAATGGGGAGGCAGTCGTGACACCCTCAGTG

ACACATTTAAACAATCTCTGGCCAAGATTCTGGTGCATTATTACCCTCT

CGCAGGGAGATTAAGATTAGGATCTGATGGGAAGTATAATGTGGAGTGT

ACCAATGAAGGGGTGTTGTTTGTGGAAGCAAGAGCAAATTGTAACATGG

ATCAAGTTGACGTTAAAGTAATTATTGATGATCATTCTGAAACAGCAGG

GAAGCTTGTCTATGGATCTCCAGATCCTGAGAACATACTGGAAAACCCT

CTAATGACTGCACAGGTTACAAGGTTCAGGTGTGGAGGTTTTGCTTTGG

GATTATCAATTAGCCACTTAATAGCTGATGGGCTATCAGCAATGGAGTT

TATCAAATCATGGTCTGAAACAGCCAGAGGGATGCCGTTAACCACTAAA

CCAGTTCTTGATAGATCAATTTTGAGGTCTAGACAACCTCCTAAAATTG

ATTTTCATTTCGACCAGTACGCTCCTGCAGAAACCAGTAACGTATCAAA

CATATCAAATCCATTTCAAGGAGAGCAGATTCTGACGAAATGCTTCCTG

TTTGATTCCAACAAGCTTGCAATACTGAAGAGCATGGCAATGGAGGACG

GAACCATCAAAAGCTGCTCAAACTTCACAGCGCTCACAGCTTTTGTGTG

GCGTGCTCGCTGCAAGGCACTGCAGATGAATCCTGATCAAACAACTCCA

CTTCTGTTAGTAGTCGACGTTCGATCCAAGCTTAATCCACCACTTCCCA

AAGGATACTTTGGCAACGGAATTGTCTTAATCACTTGCCCTGGGAGGGC

AGGAGAATTGATTAAAAACACACTATCTTTTGCAGTGGAAGAAGTGCAG

AATGGAATAAAAATGGTGAATGAGGAGTTTGTCAGGTCTTGGATTGATT

ACCTTGAAGTGATGGGAGCAAAGGACTTTCCTTTACACTCCTATTTTAA

AGTTTCTTCATGGACAAGACTTTCAATTGAGTGTTCAGACTTTGGATGG

GGAGAGCCAGCACAGTTTGCTTGCACAAACTTGCCTAAAAATTCAGCTT

TTTTCCTACCAGATGGAAAAGAAAAGAAGGGCATTAATTTGATTTTGGA

TTTGCCAGTTACTGCCATGAGCACCTTCCAGGAGCTAATGCTTCTGTAA
```

XMT9 comprises an amino acid sequence of SEQ ID NO:18:

```
(SEQ ID NO: 18)
MEGTGKHGGDQLSVKKSEPVLIEPETRTHSGFFFLCNLDHMVTHSVETV

YFYKAKKWGGSRDTLSDTFKQSLAKILVHYYPLAGRLRLGSDGKYNVEC

TNEGVLFVEARANCNMDQVDVKVIIDDHSETAGKLVYGSPDPENILENP

LMTAQVTRFRCGGFALGLSISHLIADGLSAMEFIKSWSETARGMPLTTK

PVLDRSILRSRQPPKIDFHFDQYAPAETSNVSNISNPFQGEQILTKCFL

FDSNKLAILKSMAMEDGTIKSCSNFTALTAFVWRARCKALQMNPDQTTP

LLLVVDVRSKLNPPLPKGYFGNGIVLITCPGRAGELIKNTLSFAVEEVQ

NGIKMVNEEFVRSWIDYLEVMGAKDFPLHSYFKVSSWTRLSIECSDFGW

GEPAQFACTNLPKNSAFFLPDGKEKKGINLILDLPVTAMSTFQELMLL
```

Nucleic acids encoding the aforementioned BAHD acyltransferases allow identification and isolation of related nucleic acids and their encoded enzymes that provide a means for production of altered lignins in plants.

For example, related nucleic acids can be isolated and identified by mutation of the SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence and/or by hybridization to DNA and/or RNA isolated from other plant species using SEQ ID NO:1, SEQ ID NO:3, SEQ ID NO:5, SEQ ID NO:7, SEQ ID NO:11, SEQ ID NO:13, SEQ ID NO:15, or SEQ ID NO:17 nucleic acids as probes. The sequence of the BAHD acyltransferase enzyme (e.g., SEQ ID NO:2, SEQ ID NO:4, SEQ ID NO:6, SEQ ID NO:8, SEQ ID NO:12, SEQ ID NO:14, SEQ ID NO:16, or SEQ ID NO:18) can also be examined and used as a basis for designing alternative BAHD acyltransferase nucleic acids that encode related BAHD acyltransferase polypeptides.

In one embodiment, the BAHD acyltransferase nucleic acids of the invention include any nucleic acid that can selectively hybridize to SEQ ID NO:1, SEQ ID NO:3, SEQ ID NO:5, SEQ ID NO:7, SEQ ID NO:11, SEQ ID NO:13, SEQ ID NO:15, or SEQ ID NO:17.

The term "selectively hybridize" includes hybridization, under stringent hybridization conditions, of a nucleic acid sequence to a specified nucleic acid target sequence (e.g., SEQ ID NO:1, SEQ ID NO:3, SEQ ID NO:5, SEQ ID NO:7, SEQ ID NO:11, SEQ ID NO:13, SEQ ID NO:15, or SEQ ID NO:17) to a detectably greater degree (e.g., at least 2-fold over background) than its hybridization to non-target nucleic acid sequences. Such selective hybridization substantially excludes non-target nucleic acids. Selectively hybridizing sequences typically have about at least 40% sequence identity, or at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with each other. In some embodiments, a selectively hybridizing sequence has at least about 70% or at least about 80% sequence identity or complementarity with SEQ ID NO:1, SEQ ID NO:3, SEQ ID NO:5, SEQ ID NO:7, SEQ ID NO:11, SEQ ID NO:13, SEQ ID NO:15, or SEQ ID NO:17.

Thus, the nucleic acids of the invention include those with about 500 of the same nucleotides as SEQ ID NO:1, SEQ ID NO:3, SEQ ID NO:5, SEQ ID NO:7, SEQ ID NO:11, SEQ ID NO:13, SEQ ID NO:15, or SEQ ID NO:17, or about 600 of the same nucleotides as SEQ ID NO:1, SEQ ID NO:3, SEQ ID NO:5, SEQ ID NO:7, SEQ ID NO:11, SEQ ID NO:13, SEQ ID NO:15, or SEQ ID NO:17, or about 700 of the same nucleotides as SEQ ID NO:1, SEQ ID NO:3, SEQ ID NO:5, SEQ ID NO:7, SEQ ID NO:11, SEQ ID NO:13, SEQ ID NO:15, or SEQ ID NO:17, or about 800 of the same nucleotides as SEQ ID NO:1, SEQ ID NO:3, SEQ ID NO:5, SEQ ID NO:7, SEQ ID NO:11, SEQ ID NO:13, SEQ ID NO:15, or SEQ ID NO:17, or about 900 of the same nucleotides as SEQ ID NO:1, SEQ ID NO:3, SEQ ID NO:5, SEQ ID NO:7, SEQ ID NO:11, SEQ ID NO:13, SEQ ID NO:15, or SEQ ID NO:17, or about 1000 of the same nucleotides as SEQ ID NO:1, SEQ ID NO:3, SEQ ID NO:5, SEQ ID NO:7, SEQ ID NO:11, SEQ ID NO:13, SEQ ID NO:15, or SEQ ID NO:17, or about 1100 of the same nucleotides as SEQ ID NO:1, SEQ ID NO:3, SEQ ID NO:5, SEQ ID NO:7, SEQ ID NO:11, SEQ ID NO:13, SEQ ID NO:15, or SEQ ID NO:17, or about 1200 of the same nucleotides as SEQ ID NO:1, SEQ ID NO:3, SEQ ID NO:5, SEQ ID NO:7, SEQ ID NO:11, SEQ ID NO:13, SEQ ID NO:15, or SEQ ID NO:17, or about 1300 of the same nucleotides as SEQ ID NO:1, SEQ ID NO:3, SEQ ID NO:5, SEQ ID NO:7, SEQ ID NO:11, SEQ ID NO:13, SEQ ID NO:15, or SEQ ID NO:17, or about 500-1325 of the same nucleotides as SEQ ID NO:1, SEQ ID NO:3, SEQ ID NO:5, SEQ ID NO:7, SEQ ID NO:11, SEQ ID NO:13, SEQ ID NO:15, or SEQ ID NO:17. The identical nucleotides or amino acids can be distributed throughout the nucleic acid or the protein, and need not be contiguous.

Note that if a value of a variable that is necessarily an integer, e.g., the number of nucleotides or amino acids in a nucleic acid or protein, is described as a range, e.g., 90-99% sequence identity what is meant is that the value can be any integer between 90 and 99 inclusive, i.e., 90, 91, 92, 93, 94, 95, 96, 97, 98 or 99, or any range between 90 and 99 inclusive, e.g., 91-99%, 91-98%, 92-99%, etc.

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified with up to 100% complementarity to the probe (homologous probing). Alternatively, stringency conditions can be adjusted to allow some mismatching in sequences so that lower degrees of sequence similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution.

For DNA-DNA hybrids, the $T_m$ can be approximated from the equation of Meinkoth and Wahl (*Anal. Biochem.* 138: 267-284 (1984)):

$$T_m = 81.5° C. + 16.6(\log M) + 0.41(\% GC) - 0.61(\% \text{formamide}) - 500/L$$

where, M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to SEQ ID NO:1, SEQ ID NO:3, SEQ ID NO:5, SEQ ID NO:7, SEQ ID NO:11, SEQ ID NO:13, SEQ ID NO:15, or SEQ ID NO:17.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

Unless otherwise stated, in the present application high stringency is defined as hybridization in 4×SSC, 5×Denhardt's (5 g Ficoll, 5 g polyvinylpyrrolidone, 5 g bovine serum albumin in 500 mL of water), 0.1 mg/mL boiled salmon sperm DNA, and 25 mM Na phosphate at 65° C., and a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity," and (e) "substantial identity."

As used herein, "reference sequence" is a defined sequence used as a basis for sequence comparison. The reference sequence can be a nucleic acid sequence (e.g., SEQ ID NO:1, SEQ ID NO:3, SEQ ID NO:5, SEQ ID NO:7, SEQ ID NO:11, SEQ ID NO:13, SEQ ID NO:15, or SEQ ID NO:17) or an amino acid sequence (e.g., SEQ ID NO:2, SEQ ID NO:4, SEQ ID NO:6, SEQ ID NO:8, SEQ ID NO:12, SEQ ID NO:14, SEQ ID NO:16, or SEQ ID NO:18). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 20 contiguous nucleotides in length, and optionally can be 30, 40, 50, 100 or more nucleotides. For amino acid sequences, the comparison window is at least about 10 amino acids, and can optionally be 15, 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman (1981) *Adv. Appl. Math* 2:482, may permit optimal alignment of compared sequences; by the homology alignment algorithm (GAP) of Needleman and Wunsch (1970) *J Mol. Biol.* 48:443-453; by the search for similarity method (Tfasta and Fasta) of Pearson and Lipman (1988) *Proc. Natl. Acad. Sci. USA* 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif)). The CLUSTAL program is well described by Higgins and Sharp (1988) *Gene* 73:237-244; Higgins and Sharp (1989) *CABIOS* 5:151-153; Corpet, et al. (1988) *Nucleic Acids Res.* 16:10881-10890; Huang, et al. (1992) *Computer Applications in the Biosciences* 8:155-165; and Pearson, et al. (1994) *Meth. Mol. Biol.* 24:307-331. An example of a good program to use for optimal global alignment of multiple sequences is PileUp (Feng and Doolittle (1987) *J. Mol. Evol.* 25:351-260, which is similar to the method described by Higgins and Sharp (1989) *CABIOS* 5:151-153 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995). An updated version of the BLAST family of programs includes the BLAST+ suite. (Camacho, C., Coulouris, G., Avagyan, V., Ma, N, Papadopoulos J, Bealer K, Madden T L. (2009) BLAST+: architecture and applications. *BMC Bioinformatics* 10:421).

GAP uses the algorithm of Needleman and Wunsch (1970) *J Mol. Biol.* 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or more.

GAP presents one member of the family of best alignments. There may be many members of this family. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see: Henikoff and Henikoff, (1989) Proc. Natl. Acad. Sci. USA 89:10915).

Sequence identity/similarity values provided herein can refer to the value obtained using the BLAST+2.5.0 suite of programs using default settings (blast.ncbi.nlm.nih.gov) (Camacho, C., Coulouris, G., Avagyan, V., Ma, N, Papadopoulos J, Bealer K, Madden T L. (2009) BLAST+: architecture and applications. BMC Bioinformatics 10:421).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU ($C_1$-ayerie and States (1993) Comput. Chem. 17:191-201) low-complexity filters can be employed alone or in combination.

The terms "substantial identity" and "substantially identical" indicate that a polypeptide or nucleic acid comprises a sequence with between 55-100% sequence identity to a reference sequence, with at least 55% sequence identity, or at least 60%, or at least 65%, or at least 70%, or at least 75%, or at least 80%, or at least 85%, or at least 90%, or at least 95%, or at least 99% sequence identity or any percentage of value within the range of 55-100% sequence identity relative to the reference sequence. The percent sequence identity may occur over a specified comparison window. Optimal alignment may be ascertained or conducted using the homology alignment algorithm of Needleman and Wunsch, supra.

An indication that two polypeptide sequences are substantially identical is that both polypeptides have at least one BAHD acyltransferase activity (e.g., pBMT, FMT, PMT, AMT, and/or BMT activity). The polypeptide that is substantially identical to a BAHD acyltransferase with a SEQ ID NO:2, SEQ ID NO:4, SEQ ID NO:6, SEQ ID NO:8, SEQ ID NO:12, SEQ ID NO:14, SEQ ID NO:16, or SEQ ID NO:18 sequence may not have exactly the same level of a given activity as the BAHD acyltransferase with a SEQ ID NO:2, SEQ ID NO:4, SEQ ID NO:6, SEQ ID NO:8, SEQ ID NO:12, SEQ ID NO:14, SEQ ID NO:16, or SEQ ID NO:18. Instead, the substantially identical polypeptide may exhibit greater or lesser levels of a given BAHD acyltransferase activity than the BAHD acyltransferase with SEQ ID NO:2, SEQ ID NO:4, SEQ ID NO:6, SEQ ID NO:8, SEQ ID NO:12, SEQ ID NO:14, SEQ ID NO:16, or SEQ ID NO:18, as measured by assays available in the art or described herein. For example, the substantially identical polypeptide can have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of a given activity of the BAHD acyltransferase with the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 sequence when measured by similar assay procedures.

The polypeptide that is substantially identical to a BAHD acyltransferase with a SEQ ID NO:2, SEQ ID NO:4, SEQ ID NO:6, SEQ ID NO:8, SEQ ID NO:12, SEQ ID NO:14, SEQ ID NO:16, or SEQ ID NO:18 sequence also may not have exactly the same type of BAHD acyltransferase activity as the BAHD acyltransferase with a SEQ ID NO:2, SEQ ID NO:4, SEQ ID NO:6, SEQ ID NO:8, SEQ ID NO:12, SEQ ID NO:14, SEQ ID NO:16, or SEQ ID NO:18. Instead, the substantially identical polypeptide may exhibit a different BAHD acyltransferase activity than the BAHD acyltransferase activity or activities of the BAHD acyltransferase with SEQ ID NO:2, SEQ ID NO:4, SEQ ID NO:6, SEQ ID NO:8, SEQ ID NO:12, SEQ ID NO:14, SEQ ID NO:16, or SEQ ID NO:18. Thus, a polypeptide that is substantially identical to a BAHD acyltransferase with FMT activity and no pBMT activity may have pBMT activity and no FMT activity.

Another indication that two polypeptide sequences are substantially identical is when a second polypeptide is immunologically reactive with antibodies raised against a first polypeptide (e.g., a polypeptide with SEQ ID NO:2, SEQ ID NO:4, SEQ ID NO:6, SEQ ID NO:8, SEQ ID NO:12, SEQ ID NO:14, SEQ ID NO:16, or SEQ ID NO:18). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides that are "substantially similar" share sequences as noted above except that some residue positions, which are not identical, may differ by conservative amino acid changes.

As used herein, "conservative substitution" refers a substitution of an amino acid residue at a given position between two aligned sequences with a conservative variant. Conservative variants are residues that are functionally similar. Amino acids within the following groups are conservative variants of one another: glycine, alanine, serine, and proline (very small); alanine, isoleucine, leucine, methionine, phenylalanine, valine, proline, and glycine (hydrophobic); alanine, valine, leucine, isoleucine, methionine (aliphatic-like); cysteine, serine, threonine, asparagine, tyrosine, and glutamine (polar); phenylalanine, tryptophan, tyrosine (aromatic); lysine, arginine, and histidine (basic); aspartate and glutamate (acidic); alanine and glycine; asparagine and glutamine; arginine and lysine; isoleucine, leucine, methionine, and valine; and serine and threonine.

The BAHD acyltransferase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 N-terminal amino acid residues of the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 sequence. Alternatively, the BAHD acyltransferase polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 C-terminal amino acid residues of the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 sequence.

Lignin

Lignin broadly refers to a biopolymer that is a major component of plant secondary cell walls. Lignin is a complex moderately cross-linked aromatic polymer (see, e.g., FIGS. 1A-1D). Lignin may also be covalently linked to hemicelluloses. Hemicellulose broadly refers to a class of branched sugar polymers composed of pentoses and hexoses. Hemicelluloses typically have an amorphous structure with up to hundreds of units, and they are generally at least partially soluble in dilute alkali. Cellulose broadly refers to an organic compound with the formula $(C_6H_{10}O_5)_z$ where z is an integer. Cellulose is a linear polysaccharide that can include linear chains of β-1-4-linked glucose residues of several hundred to over ten thousand units.

Lignocellulosic biomass represents an abundant, inexpensive, and locally available feedstock for conversion to carbonaceous fuel (e.g., ethanol, biodiesel, biofuel and the like). However, the complex structure of lignin, which includes ether and carbon-carbon bonds that bind together the various subunits of lignin, and the crosslinking of lignin to other plant cell wall polymers, make it the most recalcitrant of plant polymers. Thus, significant quantities of lignin in a biomass can inhibit the efficient usage of plants as a source of fuels and other commercial products. Gaining access to the carbohydrate and polysaccharide polymers of plant cells for use as carbon and energy sources therefore requires significant energy input and often harsh chemical treatments, especially when significant amounts of lignin are present. For example, papermaking procedures, in which lignin is removed from plant fibers by delignification reactions, are typically expensive, can be polluting, and generally require use of high temperatures and harsh chemicals largely because the structure of lignin is impervious to mild conditions. Plants with altered lignin structures that could be more readily cleaved under milder conditions would reduce the costs of papermaking and make the production of biofuels more competitive with currently existing procedures for producing oil and gas fuels.

Plants make lignin from a variety of subunits or monomers that are generally termed monolignols. Such primary monolignols include p-coumaryl alcohol, coniferyl alcohol, and sinapyl alcohol.

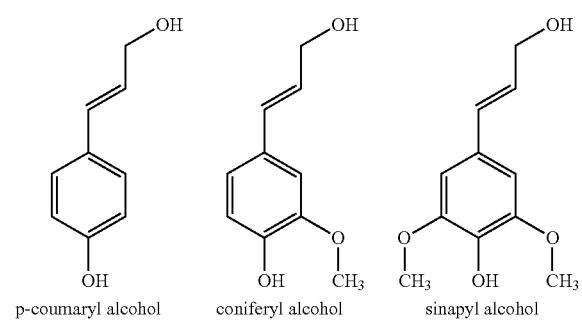

p-coumaryl alcohol    coniferyl alcohol    sinapyl alcohol

Monolignols destined for lignin polymerization in normal plants can be preacylated with p-coumarate, ferulate, p-hydroxybenzoate, benzoate, or acetate (Ralph et al. (2004) *Phytochem. Rev.* 3:29-60. Although the in planta roles of such esters, other than perhaps for improved defense, and the selection pressure that resulted in the introduction of such units into lignin in various successful plant lineages, are essentially unknown, the various plant lines possess such decorated lignins that are, in some cases, at very high levels; they are therefore apparently valuable to the plant and can provide significantly enhanced value to the lignin component that is often an underutilized waste in biorefinery operations.

p-Coumarates can acylate the γ-position of phenylpropanoid side chains mainly on the syringyl units of lignin. Studies indicate that monolignols, primarily sinapyl alcohol, are enzymatically pre-acylated with p-coumarate prior to their incorporation into lignin, indicating that the monolignol p-coumarate conjugates, coniferyl p-coumarate and sinapyl p-coumarate, can also be 'monomer' precursors of lignin.

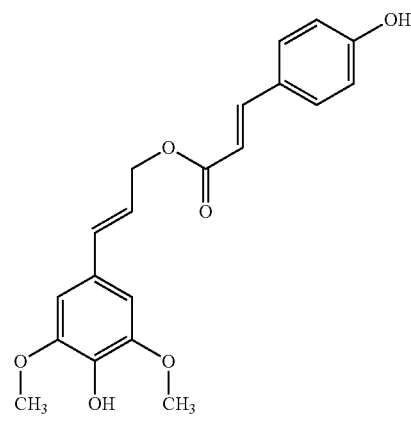

sinapyl p-coumarate

Although monolignol p-coumarate-derived units may comprise up to 40% of the lignin in some grass tissues, the p-coumarate moiety from such conjugates does not significantly enter into the radical coupling (polymerization) reactions occurring during lignification. Instead, the p-coumarate moieties substantially remain as terminal units with an unsaturated side chain and a free phenolic group (Ralph et al. (1994) 1 *Am. Chem. Soc.* 116:9448-9456; Hatfield et al. (1999) *J. Sci. Food Agric.* 79:891-899). Thus, the presence of sinapyl p-coumarate conjugates produces a lignin 'core' with terminal p-coumarate groups and no new bonds in the backbone of the lignin polymer.

Regardless, lignocellulosic biomass with lignin comprising a higher proportion of p-coumarate content is more amenable to pretreatment and saccharification (hydrolysis). Pretreatment of biomass removes a large proportion of the lignin and other materials from the cellulose and hemicellulose and enhances the porosity of the biomass for optional downstream hydrolysis. Various biomass pretreatments are well known in the art. Exemplary pretreatments include chipping, grinding, milling, steam pretreatment, ammonia fiber expansion (AFEX, also referred to as ammonia fiber explosion), ammonia recycle percolation (ARP), $CO_2$ explosion, steam explosion, ozonolysis, wet oxidation, acid hydrolysis, dilute-acid hydrolysis, alkaline hydrolysis, organosolv, extractive ammonia (EA) pretreatment, and pulsed electrical field treatment, among others. See, e.g., Kumar et al. 2009 (Kumar, P.; Barrett, D. M.; Delwiche, M.

J.; Stroeve, P. (2009) Methods for Pretreatment of Lignocellulosic Biomass for Efficient Hydrolysis and Biofuel Production. *Industrial & Engineering Chemistry Research* 48(8):3713-3729) and da Costa Sousa et al. 2016 (da Costa Sousa, L.; Jin, M.; Chundawat, S. P. S.; Bokade, V.; Tang, X.; Azarpira, A.; Lu, F.; Avci, F.; Humpula, J.; Uppugundla, N.; Gunawan, C.; Pattathil, S.; Cheh, A. M.; Kothari, N.; Kumar, N.; Ralph, J.; Hahn, M. G.; Wyman, C. E.; Singh, S.; Simmons, B. A.; Dale, B. E.; Balan, V. (2016) Next-Generation Ammonia Pretreatment Enhances Cellulosic Biofuel Production. *Energy Environ. Sci.* 9:1215-1223). Hydrolysis converts biomass polymers to fermentable sugars, such as glucose and xylose, and other monomeric or oligomeric components. Methods for hydrolyzing biomass, also known as saccharification, are well known in the art. Exemplary hydrolysis methods include enzymatic hydrolysis (e.g., with cellulases or other enzymes) and acid hydrolysis (e.g., with sulfurous, sulfuric, hydrochloric, hydrofluoric, phosphoric, nitric, acetic, and/or formic acids), among other methods. Thus, plants and biomass with lignin comprising a higher proportion of p-coumarate content are more suitable to processing for downstream applications.

Lignin comprising a higher proportion of p-coumarate content also has a higher proportion of pendant p-coumarate units, which can be cleaved from the lignin using conditions typically employed for cleaving ester bonds, described in further detail below. The cleaved p-coumarate units can be recovered for downstream uses.

p-Coumarate (or p-coumaric acid), currently valued at ~$20/kg, has some significant applications but, because it has not been previously available in bulk quantities, its applications have been limited. This could readily change with the p-coumarate-enriched lignin provided with the present invention. p-Coumarate has a number of medical/cosmetic uses. See, e.g., U.S. Pub. No. 2007/0183996 A1, U.S. Pub. No. 2007/0183996 A1, U.S. Pat. Nos. 8,481,593, 9,089,499, U.S. Pub. No. 2007/0183996, U.S. Pub. No. 2011/0237551, and U.S. Pub. No. 2013/0272983). p-Coumarate also has a large number of applications in health, food, pharmaceutical, and cosmetic industries due to its physiological functions in antioxidant, anti-mutagenesis, anti-genotoxicity, antimicrobial, anti-inflammatory, anti-melanogenesis, and anti-thrombosis activities. See Ferguson et al. 2003 (Ferguson, L. R., Lim, I. F., Pearson, A. E., Ralph, J., and Harris, P. J. (2003) Bacterial antimutagenesis by hydroxycinnamic acids from plant cell walls. *Mutation Research-Genetic Toxicology and Environmental Mutagenesis* 542(1-2):49-58), Ferguson et al. 2005 (Ferguson, L. R., Zhu, S. T., and Harris, P. J. (2005) Antioxidant and antigenotoxic effects of plant cell wall hydroxycinnamic acids in cultured HT-29 cells. *Molecular Nutrition & Food Research* 49(6):585-593), Bodini et al. (Bodini, S. F., Manfredini, S., Epp, M., Valentini, S., and Santori, F. (2009) Quorum sensing inhibition activity of garlic extract and p-coumaric acid. *Lett Appl Microbiol* 49(5):551-555), An et al. 2008 (An, S. M., Lee, S. I., Choi, S. W., Moon, S. W., and Boo, Y. C. (2008) p-Coumaric acid, a constituent of *Sasa quelpaertensis* Nakai, inhibits cellular melanogenesis stimulated by alpha-melanocyte stimulating hormone. *Brit J Dermatol.* 159(2):292-299), and Razzaghi-Asl et al. 2013 (Razzaghi-Asl, N., Garrido, J., Khazraei, H., Borges, F., and Firuzi, O. (2013) Antioxidant properties of hydroxycinnamic acids: A review of structure-activity relationships. *Current Medicinal Chemistry* 20(36):4436-4450). p-Coumarate is also used as a precursor for natural aromatic organic compounds, including p-hydroxybenzoic acid and 4-vinylphenol, or a variety of commodity chemicals, including caffeate (Nambudiri A M, Bhat J V. (1972 November) Conversion of p-coumarate into caffeate by *Streptomyces nigrifaciens*. Purification and properties of the hydroxylating enzyme. *Biochem J.* 130(2):425-33), volatile phenols (Cabrita M J P V, Patao R, Freitas A M C. (2012) Conversion of hydroxycinnamic acids into volatile phenols in a synthetic medium and red wine by *Dekkera bruxellensis. Ciencia e Tecnologia de Alimentos, Campinas* 32(1):106-111), and others. A variety of derivatives that are readily produced from p-coumarate are described in U.S. Pub. No. 2018/0298353, which is incorporated herein in its entirety.

p-Coumarate is also a versatile and attractive building block for the generation of novel, sustainable polymeric materials. The phenolic and carboxylic acid functional groups allow these building blocks to be used as monomers in step- and chain-polymerization reactions (Upton, B. M., and Kasko, A. M., (2016) Strategies for the conversion of lignin to high-value polymeric materials: Review and perspective. *Chemical Reviews* 116(4):2275-2306). Derivatives have been used for the synthesis of polyesters, where they replace petroleum-based diols (Kaneko, T., Matsusaki, M., Hang, T. T., and Akashi, M. (2004) Thermotropic liquid-crystalline polymer derived from natural cinnamoyl biomonomers. *Macromol Rapid Comm.* 25(5):673-677; Nagata, M., and Hizakae, S. (2003) Synthesis and characterization of photocrosslinkable biodegradable polymers derived from 4-hydroxycinnamic acid. *Macromol Biosci.* 3(8):412-419). Thermal polymerization of p-coumaric acid, for example, affords a liquid-crystalline polymer that adopts a nematic liquid-crystalline structure at temperatures between 215-280° C. (Kaneko, T., Matsusaki, M., Hang, T. T., and Akashi, M. (2004) Thermotropic liquid-crystalline polymer derived from natural cinnamoyl biomonomers. *Macromol Rapid Comm.* 25(5):673-677). Methacrylation of certain lignin-derived monomers has provided access to monomers that can be polymerized using conventional free-radical polymerization methods as well as via various controlled radical polymerization techniques, including atom transfer radical polymerization (ATRP) and reversible addition fragmentation chain transfer (RAFT) polymerization (Holmberg, A. L., Reno, K. H., Nguyen, N. A., Wool, R. P., and Epps, T. H. 3rd. (2016) Syringyl methacrylate, a hardwood lignin-based monomer for high-Tg polymeric materials. *ACS Macro Letters* 5(5):574-578).

In contrast to p-coumarate, ferulate esters do undergo radical coupling reactions under lignification conditions. Model ferulates, such as the ferulate shown below (where R is $CH_3-$, $CH_3-CH_2-$, a sugar, a polysaccharide, pectin, cell-wall (arabino)xylan or other plant component), readily undergo radical coupling reactions with each other and with lignin monomers and oligomers to form cross-linked networks.

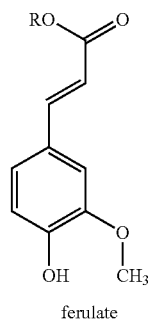

ferulate

If present during lignification, ferulates can become inextricably bound into the lignin by ether and C—C bonds. Although such ferulate moieties are no more extractable or cleavable from the lignin structure than other lignin units under most conditions, the ester itself can be readily cleaved using conditions generally employed for ester cleavage. Upon cleavage of such ester bonds, delignification is achieved under milder conditions, and other plant cell wall components can be released. For example, an arabinoxylan (hemicellulose) chain can be released from a ferulate-mediated lignin attachment by cleaving the ester.

Ferulate-monolignol ester conjugates, such as coniferyl ferulate or sinapyl ferulate, are made by plants as secondary metabolites during, among other things, lignin biosynthesis. [Paula et al. (1994) *Tetrahedron* 51:12453-12462; Seca et al. (2001) *Phytochemistry* 56:759-767; Hsiao & Chiang, (1995) *Phytochemistry* 39:899-902; Li et al. (2005) *Planta Med.* 72:278-280]. The structures of coniferyl ferulate and sinapyl ferulate are shown below.

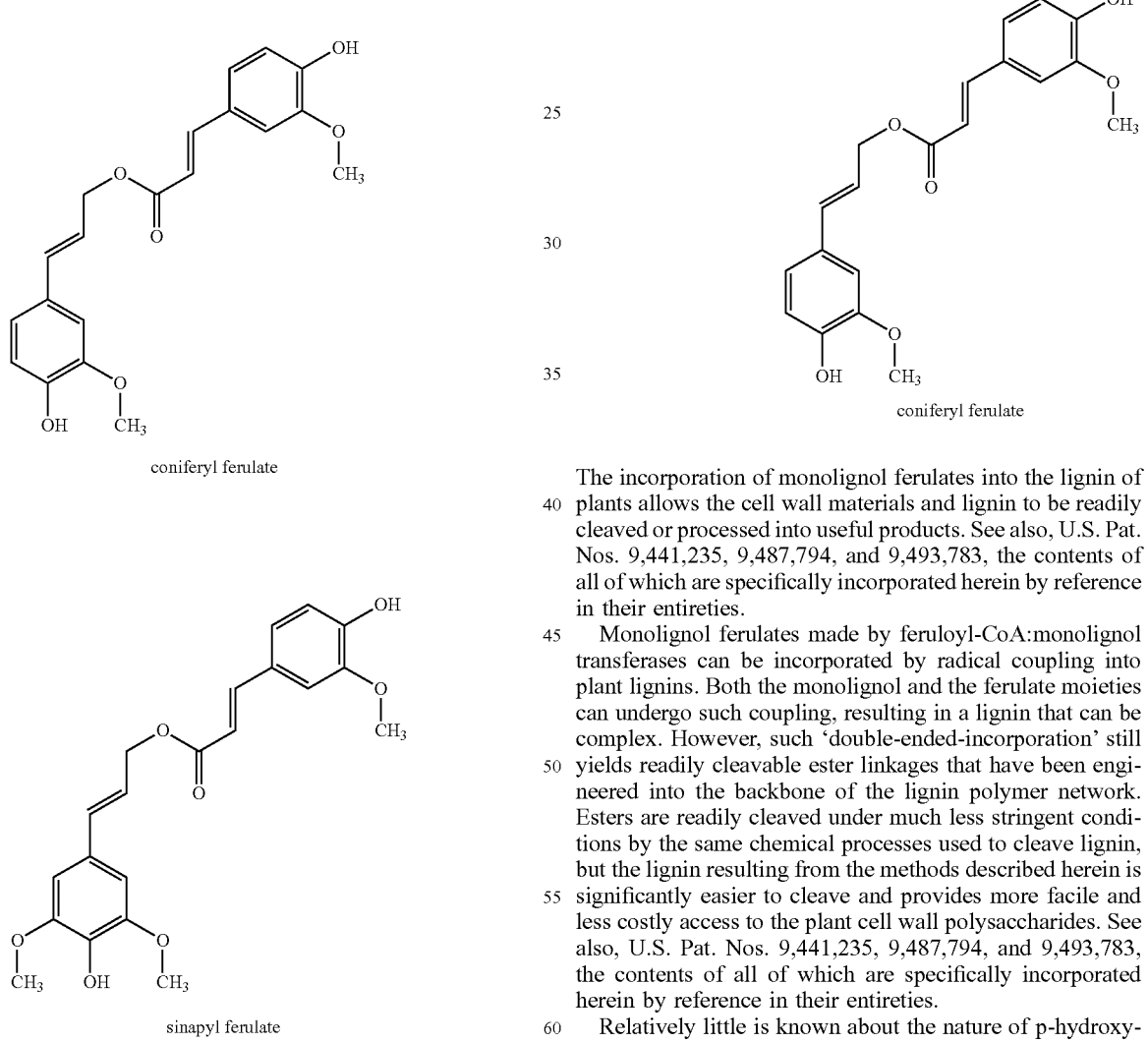

Feruloyl-CoA:monolignol transferases biosynthesize coniferyl ferulate from coniferyl alcohol and feruloyl-CoA as shown below.

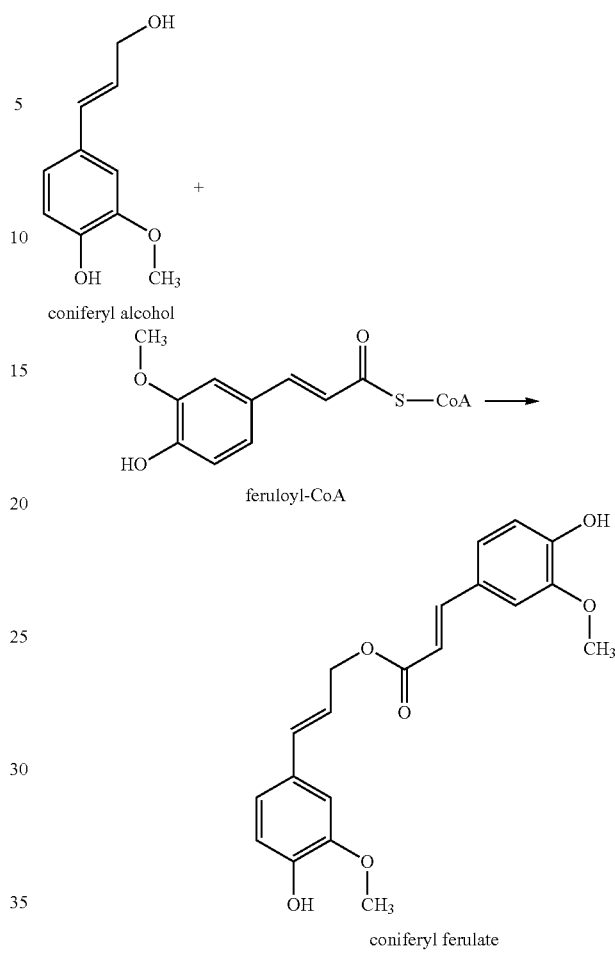

The incorporation of monolignol ferulates into the lignin of plants allows the cell wall materials and lignin to be readily cleaved or processed into useful products. See also, U.S. Pat. Nos. 9,441,235, 9,487,794, and 9,493,783, the contents of all of which are specifically incorporated herein by reference in their entireties.

Monolignol ferulates made by feruloyl-CoA:monolignol transferases can be incorporated by radical coupling into plant lignins. Both the monolignol and the ferulate moieties can undergo such coupling, resulting in a lignin that can be complex. However, such 'double-ended-incorporation' still yields readily cleavable ester linkages that have been engineered into the backbone of the lignin polymer network. Esters are readily cleaved under much less stringent conditions by the same chemical processes used to cleave lignin, but the lignin resulting from the methods described herein is significantly easier to cleave and provides more facile and less costly access to the plant cell wall polysaccharides. See also, U.S. Pat. Nos. 9,441,235, 9,487,794, and 9,493,783, the contents of all of which are specifically incorporated herein by reference in their entireties.

Relatively little is known about the nature of p-hydroxybenzoylated lignins or how they arise. As with the identification of lignin bound hydroxycinnamic acids (p-coumaric acid and ferulic acid), p-hydroxybenzoate association to lignin has long been established (Smith, D. C. C. (1955a) Ester groups in lignin. *Nature* 176:267-268; Smith, D. C. C. (1955b) p-Hydroxybenzoates groups in the lignin of Aspen (*Populus tremula*). *Journal of the Chemical Society* 2347)

on eudicot hardwoods such as poplar, willow, and aspen, and only some monocots such as palm trees. Only recently has it been determined that the p-hydroxybenzoate units are incorporated into the growing lignin polymer as monolignol conjugates (Karlen, S. D., Smith, R. A., Kim, H., Padmakshan, D., Bartuce, A., Mobley, J. K., Free, H. C. A., Smith, B. G., Harris, P. J. and Ralph, J. (2017) Highly decorated lignins occur in leaf base cell walls of the Canary Island date palm *Phoenix canariensis*. *Plant Physiology*, 175:1058-1067; Lu, F., Karlen, S. D., Regner, M., Kim, H., Ralph, S. A., Sun, R. C., Kuroda, K. I., Augustin, M. A., Mawson, R., Sabarez, H., Singh, T., Jimenez-Monteon, G., Hill, S., Harris, P. J., Boerjan, W., Mansfield, S. D. and Ralph, J. (2015) Naturally p-hydroxybenzoylated lignins in palms. *Bioenerg Res.* 8:934-952). They parallel the behavior of monolignol p-coumarates in lignification, including their ease of removal, and are analogously a potential target for enhancing a plant's value. Lignin-bound p-hydroxybenzoate units remain as pendent groups, whereas their associated monolignol moiety incorporates normally into the growing lignin polymer. The lack of in planta reactivity makes p-hydroxybenzoate an attractive unit to target for clipping off the biomass to deliver a pure compound with value as a commodity chemical.

Lignins can be degraded by chemical or enzymatic means to yield a variety of smaller monomers and oligomers. While enzymatic processes are generally preferred because they do not require high temperatures and harsh chemicals, such enzymatic processes have previously not been as effective at solubilizing lignin moieties away from valuable plant cell constituents (e.g., polysaccharides and carbohydrates).

Plants with the feruloyl-CoA:monolignol transferase nucleic acids and/or enzymes supply monolignol ferulates for facile lignification in plants, thereby yielding plants with lignins that are more readily cleaved or processed to release cellulose, hemicelluloses and lignin breakdown products.

Conditions for releasing the cellulose, hemicelluloses and lignin breakdown products from plants containing the feruloyl-CoA:monolignol transferase nucleic acids and/or enzymes include conditions typically employed for cleaving ester bonds. Thus, the ester bonds within monolignol ferulate-rich lignins can be cleaved by milder alkaline and/or acidic conditions than the conditions typically used to break down the lignin of plants that are not rich in monolignol ferulates. For example, mildly alkaline conditions involving use of ammonia may be used to cleave the ester bonds within monolignol ferulate-rich lignins, whereas such conditions would not cleave substantially any of the ether and carbon-carbon bonds in normal lignins. See also, U.S. patent application Ser. No. 12/830,905, filed Jul. 6, 2010 and to U.S. patent application Ser. No. 61/213,706, filed Jul. 6, 2009, the contents of both of which are specifically incorporated herein by reference in their entireties.

For acid digestion, exemplary methods include but are not limited to acid γ-valerolactone acid digestion (Luterbacher, J. S., Azarpira, A., Motagamwala, A. H., Lu, F., Ralph, J., and Dumesic, J. A. (2015) Aromatic monomer production integrated into the γ-valerolactone sugar platform. *Energy and Environmental Science* 8(9):2657-2663), digestion as described in Santoro et al. (Santoro, N., Cantu, S. L., Tornqvist, C. E., Falbel, T. G., Bolivar, J. L., Patterson, S. E., Pauly, M., and Walton, J. D. (2010) A high-throughput platform for screening milligram quantities of plant biomass for lignocellulose digestibility. *Bioenergy Research* 3(1):93-102), and ionic digestion (Kim, K. H., Dutta, T., Ralph, J., Mansfield, S. D., Simmons, B. A., and Singh, S. (2017) Impact of lignin polymer backbone esters on ionic liquid pretreatment of poplar. *Biotechnology for Biofuels* 10: 101, 1-10).

Plants Modified to Contain a BAHD acyltransferase

In order to engineer plants with lignins that contain increased levels of certain monolignol ester conjugates or different relative proportions of various monolignol ester conjugates, one of skill in the art can introduce BAHD acyltransferases or nucleic acids encoding such BAHD acyltransferases into the plants. For example, one of skill in the art can inject BAHD acyltransferase enzymes into young plants.

Alternatively, one of skill in the art can generate genetically modified plants that contain nucleic acids encoding BAHD acyltransferases within their somatic and/or germ cells. Such genetic modification can be accomplished by procedures available in the art. For example, one of skill in the art can prepare an expression cassette or expression vector that can express one or more encoded BAHD acyltransferase enzymes. Plant cells can be transformed by the expression cassette or expression vector, and whole plants (and their seeds) can be generated from the plant cells that were successfully transformed with the BAHD acyltransferase nucleic acids. Some procedures for making such genetically modified plants and their seeds are described below.

Promoters: The BAHD acyltransferase nucleic acids of the invention can be operably linked to a promoter, which provides for expression of mRNA from the BAHD acyltransferase nucleic acids. The promoter is typically a promoter functional in plants and/or seeds, and can be a promoter functional during plant growth and development. A BAHD acyltransferase nucleic acid is operably linked to the promoter when it is located downstream from the promoter, to thereby form an expression cassette.

Most endogenous genes have regions of DNA that are known as promoters, which regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides for a very low level of gene expression. An inducible promoter is a promoter that selectively enables the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired.

Suitable promoters for use in the present invention include native or heterologous promoters.

Expression cassettes generally include, but are not limited to, a plant promoter such as the CaMV 35S promoter (Odell et al., *Nature.* 313:810-812 (1985)), or others such as CaMV 19S (Lawton et al. (1987) *Plant Molecular Biology* 9:315-324), nos (Ebert et al. (1987) *Proc. Natl. Acad. Sci. USA.* 84:5745-5749), *Adh*1 (Walker et al. (1987) *Proc. Natl. Acad. Sci. USA.* 84:6624-6628), sucrose synthase (Yang et al. (1990) *Proc. Natl. Acad. Sci. USA.* 87:4144-4148), α-tubulin, ubiquitin, actin (Wang et al. (1992), *Mol. Cell. Biol.* 12:3399), cab (Sullivan et al. (1989) *Mol. Gen. Genet.* 215:431), PEPCase (Hudspeth et al. (1989) *Plant Molecular Biology* 12:579-589) or those associated with the R gene complex (Chandler et al. (1989) *The Plant Cell* 1:1175-1183). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al. (1984) *EMBO J.* 3(8):1671-1679) and the actin promoter from rice (McElroy et al. (1990) *The Plant Cell* 2:163-171). Seed specific promoters, such as the phaseolin promoter from beans, may also be used (Sengupta-Gopalan (1985) *Proc. Natl. Acad. Sci. USA.* 83:3320-3324). Further suitable promoters include any of the promoters on the various genes of the conventional lignin monomer (monolignol) biosynthetic pathway. See, e.g., Vanholme et al. 2012 (Vanholme, R., Morreel, K., Darrah, C., Oyarce, P., Grabber, J. H., Ralph, J., and Boerjan, W. (2012) Metabolic engineering of novel lignin in biomass crops. *New Phytol.* 196(4):978-1000); Vanholme et al. 2010 (Vanholme, R., Demedts, B., Morreel, K., Ralph, J., and Boerjan, W. (2010) Lignin biosynthesis and structure. *Plant Physiol.* 153(3):895-905), Vanholme et al. 2008 (Vanholme, R., Morreel, K., Ralph, J., and Boerjan, W. (2008) Lignin engineering. *Curr. Opin. Plant Biol.* 11(3):278-285), Boerjan et al. 2003 (Boerjan, W., Ralph, J., and Baucher, M. (2003) Lignin biosynthesis. *Annual Reviews in Plant Biology* 54:519-546). An exemplary promoter from this pathway is the cinnamate-4-hydroxylase (C4H) promoter (Bell-Lelong, D. A., Cusumano, J. C., Meyer, K., and Chapple, C. (1997) Cinnamate-4-hydroxylase expression in *Arabidopsis*: regulation in response to development and the environment. *Plant Physiol.* 113:729-738), the sequence of which is SEQ ID NO:19:

```
                                         (SEQ ID NO: 19)
aagcttagaggagaaactgagaaaatcagcgtaatgagagacgagagca atgtgctaagagaagagattgggaagagagaagagacgataaaggaaac ggaaaagcatatggaggagcttcatatggagcaagtgaggctgagaaga cggtcgagtgagcttacggaagaagtggaaaggacgagagtgtctgcat cggaaatggctgagcagaaaagagaagctataagacagctttgtatgtc tcttgaccattacagagatgggtacgacaggctttggagagttgttgcc ggccataagagtaagagagtagtggttttaacaacttgaagtgtaagaa caatgagtcaatgactacgtgcaggacattggacataccgtgtgttctt ttggattgaaatgttgtttcgaagggctgttagttgatgttgaaaatag gttgaagttgaataatgcatgttgatatagtaaatatcaatggtaatat tttctcatttcccaaaactcaaatgatatcatttaattataaactaacg taaactgttgacaatacacttatggttaaaaatttggagtcttgtttta gtatacgtatcaccaccgcacggtttcaaaaccacataattgtaaatgt tattggaaaaaagaacccgcaatacgtattgtattttggtaaacatagc tctaagcctctaatatataagctctcaacaattctggctaatggtccca agtaagaaaagcccatgtattgtaaggtcatgatctcaaaaacgagggt gaggtggaatactaacatgaggagaaagtaaggtgacaaattttttgggg caatagtggtggatatggtggggaggtaggtagcatcatttctccaagt cgctgtctttcgtggtaatggtaggtgtgtctctcttttatattatttat tactactcattgttaatttcttttttctacaatttgtttcttactcca aaatacgtcacaaatataatactaggcaaataattatttaattgtaagt caatagagtggttgttgtaaaattgattttttgatattgaaagagttcat ggacggatgtgtatgcgccaaatgctaagcccttgtagtcttgtactgt gccgcgcgtatattttaaccaccactagttgtttctcttttcaaaaac acacaaaaaataatttgttttcgtaacggcgtcaaatctgacggcgtct caatacgttcaatttttcctttctttcacatggtttctcatagctttgc attgaccataggtaaagggataaggataaaggtttttctcttgtttgt tttatccttattattcaaaatggataaaaaaacagtcttattttgattt ctttgattaaaaaagtcattgaaattcatatttgattttttgctaaatg tcaactcagagacacaaacgtaatgcactgtcgccaatattcatggatc atgaccatgaatatcactagaataattgaaaatcagtaaaatgcaaaca aagcattttctaattaaaacagtcttctacattcacttaattggaattt cctttatcaaacccaaagtccaaaacaatcggcaatgttttgcaaaatg ttcaaaactattggcgggttggtctatccgaattgaagatcttttctcc atatgatagaccaacgaaattcggcatacgtgtttttttttttgttttg aaaacccctttaaacaaccttaattcaaaatactaatgtaactttattga acgtgcatctaaaaattttgaactttgcttttgagaaataatcaatgta ccaataaagaagatgtagtacatacattataattaaatacaaaaaagga atcaccatatagtacatggtagacaatgaaaaactttaaaacatataca atcaataatactctttgtgcataactttttttgtcgtctcgagtttata tttgagtacttatacaaactattagattacaaactgtgctcagatacat taagttaatcttatatacaagagcactcgagtgttgtccttaagttaat cttaagatatcttgaggtaaatagaaatagttaactcgttttttatttc ttttttttaccatgagcaaaaaagatgaagtaagttcaaaacgtgacg aatctacatgttactacttagtatgtgtcaatcattaaatcgggaaaac ttcatcatttcaggagtactacaaaactcctaagagtgagaacgactac atagtacatattttgataaaagacttgaaaacttgctaaaacgaatttg cgaaaatataatcatacaagtagaaccactgatttgatcgaattattca tagctttgtaggatgaacttaactaaataatatctcacaaaagtattga cagtaacctagtactatactatctatgttagaatatgattatgatataa tttatcccctcacttattcatatgattttttgaagcaactactttcgttt ttttaacattttctttttttggtttttgttaatgaacatatttagtcgtt tcttaattccactcaaatagaaaatacaaagagaactttatttaataga
```

```
-continued
tatgaacataatctcacatcctcctcctaccttcaccaaacacttttac atacactttgtggtctttctttacctaccaccatcaacaacaacaccaa gccccactcacacacacgcaatcacgttaaatctaacgccgtttattat ctcatcattcaccaactcccacgtacctaacgccgtttacctttgccg ttggtcctcatttctcaaaccaaccaaacctctccctcttataaaatcc tctctcccttctttatttcttcctcagcagcttcttctgctttcaatta ctctcgccgacgattttctcaccggaaaaaaacaatatcattgcggata cacaaactata
```

Other promoters useful in the practice of the invention are known to those of skill in the art.

Alternatively, novel tissue specific promoter sequences may be employed in the practice of the present invention. cDNA clones from a particular tissue can be isolated and those clones which are expressed specifically in that tissue are identified, for example, using Northern blotting. Preferably, the gene isolated not present in a high copy number, but is relatively abundant in specific tissues. The promoter and control elements of corresponding genomic clones can then be localized using techniques well known to those of skill in the art.

A BAHD acyltransferase nucleic acid can be combined with the promoter by standard methods to yield an expression cassette, for example, as described in Sambrook et al. (MOLECULAR CLONING: A LABORATORY MANUAL. Second Edition (Cold Spring Harbor, NY: Cold Spring Harbor Press (1989); MOLECULAR CLONING: A LABORATORY MANUAL. Third Edition (Cold Spring Harbor, NY: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, California (e.g., pBI121 or pBI221). Typically, these plasmids are constructed to have multiple cloning sites having specificity for different restriction enzymes downstream from the promoter. The BAHD acyltransferase nucleic acids can be subcloned downstream from the promoter using restriction enzymes and positioned to ensure that the DNA is inserted in proper orientation with respect to the promoter so that the DNA can be expressed as sense RNA. Once the BAHD acyltransferase nucleic acid is operably linked to a promoter, the expression cassette so formed can be subcloned into a plasmid or other vector (e.g., an expression vector).

In some embodiments, a cDNA clone encoding a BAHD acyltransferase protein is isolated from a selected plant tissue, or a nucleic acid encoding a mutant or modified BAHD acyltransferase protein is prepared by available methods or as described herein. For example, the nucleic acid encoding a mutant or modified BAHD acyltransferase protein can be any nucleic acid with a coding region that hybridizes to SEQ ID NO:1, SEQ ID NO:3, SEQ ID NO:5, SEQ ID NO:7, SEQ ID NO:11, SEQ ID NO:13, SEQ ID NO:15, or SEQ ID NO:17 and that has BAHD acyltransferase activity. Using restriction endonucleases, the entire coding sequence for the BAHD acyltransferase is subcloned downstream of the promoter in a 5' to 3' sense orientation.

Targeting Sequences: Additionally, expression cassettes can be constructed and employed to target the BAHD acyltransferase nucleic acids to an intracellular compartment within plant cells or to direct an encoded protein to the extracellular environment. This can generally be achieved by joining a DNA sequence encoding a transit or signal peptide sequence to the coding sequence of the BAHD acyltransferase nucleic acid. The resultant transit, or signal, peptide will transport the protein to a particular intracellular, or extracellular destination, respectively, and can then be posttranslationally removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3' Sequences: When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., (1983) *Nucleic Acid Research*. 11:369-385), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology*. 153:292 (1987)). Many such 3' nontranslated regulatory sequences are already present in plasmids available from commercial sources such as Clontech, Palo Alto, California. The 3' nontranslated regulatory sequences can be operably linked to the 3' terminus of the BAHD acyltransferase nucleic acids by standard methods.

Selectable and Screenable Marker Sequences: In order to improve identification of transformants, a selectable or screenable marker gene can be employed with the expressible BAHD acyltransferase nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Example of proteins suitable for modification in this manner include extensin or hydroxyproline rich glycoprotein (HPRG). For example, the maize HPRG (Stiefel et al. (1990) *The Plant Cell.* 2:785-793) is well characterized in terms of molecular biology, expression, and protein structure and therefore can readily be employed. However, any one of a variety of extensins and/or glycine-rich wall proteins (Keller et al. (1989) *EMBO J.* 8:1309-1314) could be modified by the addition of an antigenic site to create a screenable marker.

Numerous other possible selectable and/or screenable marker genes will be apparent to those of skill in the art in addition to the one set forth herein below. Therefore, it will be understood that the discussion herein is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use in connection with the present invention include, but are not limited to, a neo gene (Potrykus et al. (1985) *Mol. Gen. Genet.* 199:183-188) which codes for kanamycin resistance and can be selected for using kanamycin, G418, and the like; a bar gene which codes for bialaphos resistance; a gene which encodes an altered EPSP synthase protein (Hinchee et al., (1988) *Bio/Technology.* 6:915-922) thus conferring glyphosate resistance; a nitrilase gene such as bxn from *Klebsiella ozaenae* which confers resistance to bromoxynil (Stalker et al. (1988) *Science.* 242:419-423); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al. (1988) *J. Biol. Chem.* 263:12500-12508); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al. (1986) *Mol. Gen. Genet.* 205:42-50; Twell et al. (1989) *Plant Physiol.* 91:1270-1274) causing rapid accumulation of ammonia and cell death. The success in using this selective system in conjunction with monocots was surprising because of the major difficulties that have been reported in transformation of cereals (Potrykus (1989) *Trends Biotech.* 7:269-273).

Screenable markers that may be employed include, but are not limited to, a (3-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: Chromosome Structure and Function: Impact of New Concepts, 18$^{th}$ Stadler Genetics Symposium, J. P. Gustafson and R. Appels, eds. (New York: Plenum Press) pp. 263-282 (1988)); a β-lactamase gene (Sutcliffe (1978) *Proc. Natl. Acad. Sci. USA.* 75:3737-3741), which encodes an enzyme for which various chromogenic substrates are known (e.g., PADAC, a chromogenic cephalosporin); a xylE gene (Zukowsky et al. (1983) *Proc. Natl. Acad. Sci. USA.* 80:1101) which encodes a catechol dioxygenase that can convert chromogenic catechols; an α-amylase gene (Ikuta et al. (1990) *Bio/technology* 8:241-242); a tyrosinase gene (Katz et al. (1983) 1 Gen. *Microbiol.* 129:2703-2714) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al. (1986) *Science* 234:856-859), which allows for bioluminescence detection; or an aequorin gene (Prasher et al. (1985) *Biochem. Biophys. Res. Comm.* 126:1259-1268), which may be employed in calcium-sensitive bioluminescence detection, or a green or yellow fluorescent protein gene (Niedz et al. (1995) *Plant Cell Reports.* 14:403).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, Pl. Alternatively, any genotype of maize can be utilized if the C1 and R alleles are introduced together.

The R gene regulatory regions may be employed in chimeric constructs in order to provide mechanisms for controlling the expression of chimeric genes. More diversity of phenotypic expression is known at the R locus than at any other locus (Coe et al., in *Corn and Corn Improvement*, eds. Sprague, G. F. & Dudley, J. W. (Am. Soc. Agron., Madison, WI), pp. 81-258 (1988)). It is contemplated that regulatory regions obtained from regions 5' to the structural R gene can be useful in directing the expression of genes, e.g., insect resistance, drought resistance, herbicide tolerance, or other protein coding regions. For the purposes of the present invention, it is believed that any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras, or multiwell luminometry. It is also envisioned that this system may be developed for population screening for bioluminescence, such as on tissue culture plates, or even for whole plant screening.

Other Optional Sequences: An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, preferably encoding antibiotic or herbicide resistance, unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology* 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the co/El replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes: Once the expression cassette is constructed and subcloned into a suitable plasmid, it can be screened for the ability to substantially inhibit the translation of an mRNA coding for a seed storage protein by standard methods such as hybrid arrested translation. For example, for hybrid selection or arrested translation, a preselected antisense DNA sequence is subcloned into an SP6/T7 containing plasmids (as supplied by ProMega Corp.). For transformation of plants cells, suitable vectors include plasmids such as described herein. Typically, hybrid arrest translation is an in vitro assay that measures the inhibition of translation of an mRNA encoding a particular seed storage protein. This screening method can also be used to select and identify preselected antisense DNA sequences that inhibit translation of a family or subfamily of zein protein genes. As a control, the corresponding sense expression cassette is introduced into plants and the phenotype assayed.

DNA Delivery of the DNA Molecules into Host Cells: The present invention generally includes steps directed to introducing BAHD acyltransferase nucleic acids, such as a preselected cDNA encoding the selected BAHD acyltransferase enzyme, into a recipient cell to create a transformed cell. In some instances, the frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants, through the application of the techniques disclosed herein.

Another aspect of the invention is a plant with lignin containing modified monolignol ester conjugate content, wherein the plant has an introduced BAHD acyltransferase nucleic acid. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. Suitable examples of plant species include grasses (switchgrass, sorghum, etc.), softwoods, hardwoods, wheat, rice, *Arabidopsis*, tobacco, maize, soybean, sorghum, and the like. In some embodiments, the plant or cell is a monocotyledon plant or cell. For example, the plant or cell can be a softwood plant or cell, or a maize plant or cell. In some embodiments, the plant or cell is a dicotyledon plant or cell. For example, the plant or cell can be a hardwood plant or cell. The cell(s) may be in a suspension cell culture or may be in an intact plant part, such as an immature embryo, or in a specialized plant tissue, such as callus, such as Type I or Type II callus.

Transformation of the plant cells can be conducted by any one of a number of methods known to those of skill in the art. Examples are: Transformation by direct DNA transfer into plant cells by electroporation (U.S. Pat. Nos. 5,384,253 and 5,472,869; Dekeyser et al. (1990) *The Plant Cell* 2:591-602); direct DNA transfer to plant cells by PEG precipitation (Hayashimoto et al. (1990) *Plant Physiol.* 93:857-863); direct DNA transfer to plant cells by microprojectile bombardment (McCabe et al. (1988) *Bio/Technology* 6:923-926; Gordon-Kamm et al. (1990) *The Plant Cell* 2:603-618; U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al. (1985) *Science* 227:1229-1231. Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature *Zea mays* embryos can be transformed by accelerated particle treatment as described by Gordon-Kamm et al. (*The Plant Cell* 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in PCT publication WO 95/06128. Furthermore, methods for transformation of monocotyledonous plants utilizing *Agrobacterium tumefa*-

*ciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*-derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspensions, culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Similar tissues can be transformed for softwood or hardwood species. Selection of tissue sources for transformation of monocots is described in detail in PCT publication WO 95/06128.

The transformation is carried out under conditions directed to the plant tissue of choice. The plant cells or tissue are exposed to the DNA or RNA carrying the BAHD acyltransferase nucleic acids for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation: Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases), or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment: A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic BMS cells were bombarded with intact cells of the bacteria *E. coli* or *Agrobacterium tumefaciens* containing plasmids with either the β-glucuronidase or bar gene engineered for expression in maize. Bacteria were inactivated by ethanol dehydration prior to bombardment. A low level of transient expression of the β-glucuronidase gene was observed 24-48 hours following DNA delivery. In addition, stable transformants containing the bar gene were recovered following bombardment with either *E. coli* or *Agrobacterium tumefaciens* cells. It is contemplated that particles may contain DNA rather than be coated with DNA. Hence, it is proposed that particles may increase the level of DNA delivery but are not, in and of themselves, necessary to introduce DNA into plant cells.

An advantage of microprojectile bombardment, in addition to it being an effective means of reproducibly stably transforming monocots, is that the isolation of protoplasts (Christou et al. (1987) *Proc. Natl. Acad. Sci. USA*. 84:3962-3966), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al. (1990) *The Plant Cell* 2:603-618). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here-in one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize:

After effecting delivery of a BAHD acyltransferase nucleic acid to recipient cells by any of the methods discussed above, the transformed cells can be identified for further culturing and plant regeneration. As mentioned above, in order to improve the ability to identify transformants, one may desire to employ a selectable or screenable marker gene as, or in addition to, the expressible BAHD acyltransferase nucleic acids. In this case, one would then generally assay the potentially transformed cell population by exposing the cells to a selective agent or agents, or one would screen the cells for the desired marker gene trait.

Selection: An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/L bialaphos or about 1-3 mM glyphosate, as appropriate. While ranges of about 1-3 mg/L bialaphos or about 1-3 mM glyphosate can be employed, it is proposed that ranges of at least about 0.1-50 mg/L bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of Zea mays L. can be selected with sub-lethal levels of bialaphos. Slowly growing tissue was subsequently screened for expression of the luciferase gene and transformants can be identified.

Regeneration and Seed Production: Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the BAHD acyltransferase nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced BAHD acyltransferase nucleic acids, the plant is self-pollinated at least once in order to produce a homozygous backcross converted inbred containing the BAHD acyltransferase nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the BAHD acyltransferase nucleic acids (or the BAHD acyltransferase enzyme). Transgenic plant and/or seed tissue can be analyzed for BAHD acyltransferase expression using standard methods such as SDS polyacrylamide gel electrophoresis, liquid chromatography (e.g., HPLC) or other means of detecting a product of BAHD acyltransferase activity.

Once a transgenic seed expressing the BAHD acyltransferase sequence and having a modification in monolignol ester conjugate content in the lignin of the plant is identified, the seed can be used to develop true breeding plants. The true breeding plants are used to develop a line of plants with a modification in monolignol ester conjugate content in the lignin of the plant while still maintaining other desirable functional agronomic traits. Adding the trait of modified monolignol ester conjugate content in the lignin of the plant can be accomplished by back-crossing with this trait and with plants that do not exhibit this trait and studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of modified monolignol ester conjugate content in the lignin of the plant. The resulting progeny are then crossed back to the parent that expresses the modified monolignol ester conjugate content trait. The progeny from this cross will also segregate so that some of the progeny carry the trait and some do not. This back-crossing is repeated until an inbred line with the desirable functional agronomic traits, and with expression of the trait involving modified monolignol ester conjugate content within the lignin of the plant. Such expression of the modified monolignol ester conjugate content in plant lignin can be expressed in a dominant fashion.

Subsequent to back-crossing, the new transgenic plants can be evaluated for a modified monolignol ester conjugate content incorporated into the lignin of the plant. This can be done, for example, by NMR analysis of whole plant cell walls (Kim, H., and Ralph, J. (2010) Solution-state 2D NMR of ball-milled plant cell wall gels in DMSO-$d_6$/pyridine-$d_5$. *Org. Biomol. Chem.* 8(3):576-591; Yelle, D. J., Ralph, J., and Frihart, C. R. (2008) Characterization of non-derivatized plant cell walls using high-resolution solution-state NMR spectroscopy. *Magn. Reson. Chem.* 46(6):508-517; Kim, H., Ralph, J., and Akiyama, T. (2008) Solution-state 2D NMR of Ball-milled Plant Cell Wall Gels in DMSO-$d_6$. *BioEnergy Research* 1(1):56-66; Lu, F., and Ralph, J. (2003) Non-degradative dissolution and acetylation of ball-milled plant cell walls; high-resolution solution-state NMR. *Plant J.* 35(4):535-544). The new transgenic plants can also be evaluated for a battery of functional agronomic characteristics such as lodging, kernel hardness, yield, resistance to disease, resistance to insect pests, drought resistance, and/or herbicide resistance.

Plants that may be improved by these methods include but are not limited to oil and/or starch plants (canola, potatoes, lupins, sunflower and cottonseed), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and eucalyptus). In some embodiments the plant is a gymnosperm. Examples of plants useful for pulp and paper production include most pine species such as loblolly pine, Jack pine, Southern pine, Radiata pine, spruce, Douglas-fir, and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, willow, and the like. Plants useful for generating dairy forage include legumes such as alfalfa, as well as forage grasses such as bromegrass and bluestem.

Determination of Stably Transformed Plant Tissues: To confirm the presence of the BAHD acyltransferase nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced BAHD acyltransferase nucleic acids. PCR also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

Although Southern blotting and PCR may be used to detect the BAHD acyltransferase nucleic acid in question, they do not provide information as to whether the preselected DNA segment is being expressed. Expression may be evaluated by specifically identifying the protein products of the introduced BAHD acyltransferase nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the BAHD acyltransferase such as evaluation by amino acid sequencing following purification. The examples of this application also provide assay procedures for detecting and quantifying BAHD acyltransferase activity. Other procedures may be additionally used.

The expression of a gene product can also be determined by evaluating the phenotypic results of its expression. These assays also may take many forms including but not limited to analyzing changes in the chemical composition, morphology, or physiological properties of the plant. Chemical composition may be altered by expression of preselected DNA segments encoding storage proteins which change amino acid composition and may be detected by amino acid analysis.

Expressing XMTs in a plant will modulate or alter the monolignol ester conjugates in the plant, such as in the lignin of the plant. For example, increasing a pBMT, an FMT, a PMT, an AMT, and/or a BMT will increase the absolute amount or relative proportion of monolignol p-hydroxybenzoates, monolignol ferulates, monolignol p-coumarates, monolignol acetates, and/or monolignol benzoates, respectively, in the plant, such as in the lignin of the plant.

Increasing pBMT activity in a plant can have one or more of the following effects or advantages: increasing the production of pBA, which could be isolated for sale as a commodity chemical; controlling production of pBA in a tissue specific manner to optimize production of pBA while not impacting biomass amount which affects yields of sugar that can be isolated from the biomass; produce a new type of hydrolytically digestible molecule in plants (e.g., monolignol vanillate and/or monolignol syringate); and increasing fungal, microbial, and insect resistance.

Increasing FMT activity in a plant can have one or more of the following effects or advantages: increasing the production of monolignol ferulate to increase hydrolytic digestibility of lignin in plants; controlling production and tissue specificity of monolignol ferulate; increasing digestibility and improving pulping; and increasing fungal, microbial, and insect resistance.

Increasing PMT activity in a plant can have one or more of the following effects or advantages: increasing the production of monolignol p-coumarate (metabolite or cell-wall-bound); control production and tissue specificity of monolignol p-coumarate; and increasing fungal, microbial, and insect resistance.

Increasing BMT function and utility activity in a plant can have one or more of the following effects or advantages: increasing the production of BA (metabolite or cell-wall-bound); controlling production and tissue specificity of BA; and increasing fungal, microbial, and insect resistance.

Inhibition, Knockdown, or Knockout of BAHD Acyltransferases in Plants

Nucleic acids encoding BAHD acyltransferases can be targeted for inhibition, knockdown or knockout. Such nucleic acids can include a nucleic acid that can selectively hybridize to a DNA with a SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence, and/or a nucleic acid that encodes a SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase polypeptide comprising a sequence substantially identical to the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence, and/or a nucleic acid that encodes a BAHD acyltransferase with at least about 50% of at least one BAHD acyltransferase activity of a BAHD acyltransferase with the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 amino acid sequence.

Methods for inhibiting, knocking down, or knocking out nucleic acids encoding BAHD acyltransferases are described below and in U.S. Pub. No. 2016/0046955, which is incorporated herein by reference.

BAHD acyltransferase nucleic acids that are endogenous within various species of plant cells, seeds and plants can be targeted for knockout by mutation using mutagens or recombinant technology. In addition, inhibitory nucleic acids that are homologous, identical and/or complementary to any of the SEQ ID NO:1, SEQ ID NO:3, SEQ ID NO:5, SEQ ID NO:7, SEQ ID NO:11, SEQ ID NO:13, SEQ ID NO:15, or SEQ ID NO:17 BAHD acyltransferase nucleic acids can be used to inhibit the expression of a BAHD acyltransferase.

Provided herein are partial or full PMT knockout mutant plants and partial or full PMT knockout plant cells. "Knockout" means that a plant has a mutation in an endogenous BAHD acyltransferase gene that substantially reduces or deletes the expression of function of the protein encoded by the gene compared to a wild-type plant that has no such mutation. For example, a knockout mutation can reduce BAHD acyltransferase expression by about 80%, or by 90%, or by 95%, or by 98%, or by 99%, or by 100%.

"Knockdown" means that the expression or function of an endogenous gene is partially suppressed. Knockdown can be accomplished by mutation of the endogenous gene so that a protein with reduced function is expressed, or by introduction of an inhibitory RNA that reduces production of the active protein. For example, a knockdown can reduce BAHD acyltransferase expression by at least 10%, or by 20%, or by 30%, or by 40%, or 50%, or by 60%, or by 70%. While knockdown is generally understood to only partially reduce the function of a gene, BAHD acyltransferase expression can be reduced by introduction of an inhibitory nucleic acid by about 95%.

Plants, plant cells and seeds can have the knockout and/or knockdown mutation. Plants, plant cells and seeds also can have an inhibitory nucleic acid that reduces BAHD acyltransferase expression. BAHD acyltransferase inhibitory nucleic acids can lead to, complete or partial reduction expression of BAHD acyltransferase. Nucleic acid sequences that can facilitate partial and full knockout of BAHD acyltransferase in plant cells and plants are also provided herein, and are referred to as BAHD acyltransferase mutating nucleic acids.

The endogenous mutant knockout or knockdown BAHD acyltransferase nucleic acid molecules can include one or more mutations, such as one or more missense mutations, nonsense mutations, STOP codon mutations, insertion mutations, deletion mutation, frameshift mutations and/or splice site mutations. Basically, an endogenous knockout or knockdown BAHD acyltransferase nucleic acid can include any mutation that results in little or no expression of the BAHD acyltransferase protein, or in expression of a BAHD acyltransferase protein that has at least one amino acid insertion, deletion and/or substitution relative to the wild-type protein resulting in a non-functional BAHD acyltransferase protein or no BAHD acyltransferase protein at all. Such mutations result in a partial or full knockout BAHD acyltransferase allele. It is, however, understood that mutations in certain parts of the protein are more likely to result in a non-functional BAHD acyltransferase protein, such as mutations leading to truncated proteins. Such truncated proteins can have one or more of the functional amino acid residues or significant portions of the functional domains deleted or replaced.

Thus, in one embodiment, nucleic acid sequences comprising one or more of the mutations described above are provided (in isolated form), as well as plants, plant cells, plant parts and plant seeds endogenously comprising such sequences. Mutant BAHD acyltransferase alleles may be generated (for example, induced by chemical or recombinant mutagenesis) and/or identified using a range of methods available in the art (for example using PCR based methods to amplify part or all of the mutant BAHD acyltransferase genomic DNA or cDNA).

Mutant BAHD acyltransferase alleles may be generated and/or identified using a range of available methods. For example, partial or full knockout of BAHD acyltransferase function can be induced by chemical or insertional mutagenesis, recombinant technology, and other available techniques. Mutagens such as ethyl methanesulfonate, radiation, *Agrobacterium tumefaciens*-mediated T-DNA transformation, transposon mutagenesis, zinc finger nuclease (ZFN)-mediated targeting of natural genes by homologous recombination, and variations thereof can be used. In some embodiments, the Rapid Trait Development System (RTDS™) developed by Cibus can be employed (see, website at cibus.com). Additional embodiments include the use of CRISPR/Cas9. See Liu et al. (Liu X, Wu S, Xu J, Sui C, Wei J. (2017) Application of CRISPR/Cas9 in plant biology. *Acta Pharm* Sin B. 7(3):292-302).

Plant seeds or plant cells comprising one or more mutant BAHD acyltransferase alleles can be generated and identified using other methods, such as the "Delete-a-gene™" method that employs PCR to screen for deletion mutants generated by fast neutron mutagenesis (reviewed by Li and Zhang, 2002, *Funct Integr Genomics* 2:254-258), by the TILLING (Targeting Induced Local Lesions IN Genomes) method that identifies EMS-induced point mutations using denaturing high-performance liquid chromatography (DHPLC) to detect base pair changes by heteroduplex analysis (McCallum et al. (2000) *Nat Biotech* 18:455; McCallum et al. (2000) *Plant Physiol.* 123:439-442; etc.). As mentioned, TILLING uses high-throughput screening for mutations (e.g., using Cel 1 cleavage of mutant-wild type DNA heteroduplexes and detection using a sequencing gel system). The use of TILLING to identify plants or plant parts comprising one or more mutant BAHD acyltransferase alleles and methods for generating and identifying such plants, plant organs, tissues and seeds is encompassed herein.

The methods provided herein can also include one or more of the following steps: mutagenizing plant cells or seeds (e.g., EMS mutagenesis, T-DNA insertion, mutation via recombinant insertion or replacement of defective sequences), pooling of plant individuals or plant DNA, PCR amplification of a region of interest, heteroduplex formation and high-throughput detection, identification of a mutant plant or DNA, and/or sequencing of mutant nucleic acid products. It is understood that other mutagenesis and selection methods may also be used to generate such mutant plants.

Instead of inducing mutations in BAHD acyltransferase alleles, natural (spontaneous) mutant alleles may be identified by methods available in the art. For example, ECO-TILLING may be used (Henikoff et al. (2004), *Plant Physiology* 135(2):630-6) to screen a plurality of plants or plant parts for the presence of natural mutant BAHD acyltransferase alleles. As for the mutagenesis techniques above, species are screened so that the identified BAHD acyltransferase allele can subsequently be introduced into other species, such as any of those listed herein, by crossing (inter- or intraspecific crosses) and selection. In ECOTILLING natural polymorphisms in breeding lines or related species are screened for by the TILLING methodology described above, in which individual or pools of plants are used for PCR amplification of the BAHD acyltransferase target, heteroduplex formation and high-throughput analysis. This can be followed by selecting individual plants having a required mutation that can be used subsequently in a breeding program to incorporate the desired mutant allele.

The identified mutant alleles can be sequenced and the sequence can be compared to the wild type allele to identify the mutation(s). Optionally, whether a mutant allele functions as a partial or full knockout BAHD acyltransferase mutant allele can be tested as described herein. Using this approach, a plurality of mutant BAHD acyltransferase alleles (and plants comprising one or more of these) can be identified. The desired mutant alleles can then be combined with the desired wild type alleles by crossing and selection methods. A single plant comprising the desired number of mutant BAHD acyltransferase and the desired number of wild type and or knockout BAHD acyltransferase alleles is generated.

Mutant BAHD acyltransferase alleles or plants comprising mutant BAHD acyltransferase alleles can be identified or detected by methods available in the art, such as direct sequencing, PCR based assays, or hybridization-based assays. Alternatively, methods can also be developed using the specific mutant BAHD acyltransferase allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex. Briefly, in the Invader™ technology, the target mutation sequence may e.g. be hybridized with a labeled first nucleic acid oligonucleotide comprising the nucleotide sequence of the mutation sequence or a sequence spanning the joining region between the 5' flanking region and the mutation region and with a second nucleic acid oligonucleotide comprising the 3' flanking sequence immediately downstream and adjacent to the mutation sequence, wherein the first and second oligonucleotide overlap by at least one nucleotide. The duplex or triplex structure that is produced by this hybridization allows selective probe cleavage with an enzyme (Cleavase®) leaving the target sequence intact. The cleaved labeled probe is subsequently detected, potentially via an intermediate step resulting in further signal amplification.

Following mutagenesis, plants are grown from the treated seeds, or regenerated from the treated cells using available techniques. For instance, mutagenized seeds may be planted in accordance with conventional growing procedures and, following self-pollination, seed is formed on the plants. Alternatively, doubled haploid plantlets may be extracted from treated microspore or pollen cells to immediately form homozygous plants. Seeds formed as a result of such self-pollination or seeds from subsequent generations may be harvested and screened for the presence of mutant BAHD acyltransferase alleles, using techniques that are available in the art, for example polymerase chain reaction (PCR) based techniques (amplification of the BAHD acyltransferase alleles) or hybridization-based techniques, e.g., Southern blot analysis, BAC library screening, and the like, and/or direct sequencing of BAHD acyltransferase alleles. To screen for the presence of point mutations (e.g., Single Nucleotide Polymorphisms or SNPs) in mutant BAHD acyltransferase alleles, available SNP detection methods can be used, for example oligo-ligation-based techniques, single base extension-based techniques, such as pyrosequencing, or techniques based on differences in restriction sites, such as TILLING.

The invention also provides inhibitory nucleic acids that can reduce the expression and/or translation of BAHD acyltransferases in plant or plant cells. In other embodiments, the invention provides mutating nucleic acids that can knockout the expression of a BAHD acyltransferase in a plant or plant cell. The inhibitory nucleic acid can, for example, reduce the expression of a BAHD acyltransferase by any amount such as, for example, by 2%, 5%, 10%, 20%, 40% or more than 40%.

In one embodiment, an inhibitory nucleic acid may be an oligonucleotide that will hybridize to a BAHD acyltransferase nucleic acid under intracellular, physiological or stringent conditions. The oligonucleotide is capable of reducing expression of a nucleic acid encoding the BAHD acyltransferase. A nucleic acid encoding a BAHD acyltransferase may be genomic DNA as well as messenger RNA. The inhibitory nucleic acid may, for example, be incorporated into a plasmid vector or viral DNA. The inhibitory nucleic acid may be single stranded or double stranded, circular or linear. The inhibitory nucleic acid may also have a stem-loop structure.

A mutating nucleic acid can, for example, have two segments that are complementary to a targeted BAHD acyltransferase gene. Such a mutating nucleic acid can hybridize via those two segments to an endogenous BAHD acyltransferase gene within a plant cell and replace or mutate segments of the endogenous BAHD acyltransferase gene. For example, a mutating nucleic acid can include two segments, referred to segment A and segment B, that are separately selected from any of the BAHD acyltransferase nucleic acid sequences described herein, with a non-BAHD acyltransferase nucleic acid segment between segments A and B. The non-BAHD acyltransferase nucleic acid sequence has at least one nucleotide that can replace at least one nucleotide in vivo within an endogenous plant BAHD acyltransferase. Segment B is selected from a region that is downstream (3') to the segment A sequence. Segments A and B are each separately about 15-50 nucleotides in length, or about 16-40 nucleotides in length, or about 17-30 nucleotides in length, or about 18-25 nucleotides in length, or any number of nucleotides in length between 15-50 nucleotides.

The non-BAHD acyltransferase segment is at least one nucleotide in length. However, the non-BAHD acyltransferase segment can also be 1-10,000 nucleotides in length, or 1-1000 nucleotides in length, or 1-100 nucleotides in length, or 1-50 nucleotides in length, or 1-20 nucleotides in length, or 5-50 nucleotides in length, or any numerical value or range within 1-10000 nucleotides in length.

Such a mutating nucleic acid can introduce point mutations into the endogenous BAHD acyltransferase gene, or it can replace whole parts of the endogenous BAHD acyltransferase gene.

The inhibitory or mutating nucleic acids can be polymers of ribose nucleotides or deoxyribose nucleotides. For example, inhibitory and/or mutating nucleic acids may include naturally occurring nucleotides as well as synthetic, modified, or pseudo-nucleotides. The inhibitory and/or mutating nucleic acids can include modified nucleotides such as phosphorothiolates; 2'-O-alkyl-containing nucleotides, and nucleotides having a detectable label such as $^{32}P$, biotin or digoxigenin. The inhibitory and mutating nucleic acids can include peptide nucleic acid (PNA), locked nucleic acid (LNA) and morpholino nucleotide sequences.

Such inhibitory or mutating nucleic acids can be of varying lengths. For example, an inhibitory oligonucleotide can be more than 13 nucleotides, or more than 14 nucleotides, or more than 15 nucleotides, or more than 16 nucleotides, or more than 17 nucleotides in length. Mutating nucleic acids be of similar length but are often longer than inhibitory nucleic acids. For example, a mutating nucleic acid can be more than 30 nucleotides in length.

An inhibitory or mutating nucleic acid that can reduce the expression and/or activity of a BAHD acyltransferase nucleic acid, may include segments that are completely complementary and/or completely identical to the BAHD acyltransferase nucleic acid (e.g., a DNA or RNA). Alternatively, some variability between the sequences may be permitted. An inhibitory or mutating nucleic acid that can inhibit or knockout a BAHD acyltransferase nucleic acid can hybridize to the BAHD acyltransferase nucleic acid under intracellular conditions or under stringent hybridization conditions. For example, an inhibitory or mutating nucleic acid can be sufficiently complementary to inhibit expression of, or to recombine and replace, an endogenous BAHD acyltransferase nucleic acid. Intracellular conditions refer to conditions such as temperature, pH and salt concentrations typically found inside a cell, for example, a living plant cell.

Inhibitory nucleic acids (e.g., oligonucleotides) and/or mutating nucleic acids can include, for example, 2, 3, 4, or 5 or more stretches of contiguous nucleotides that are precisely complementary to a BAHD acyltransferase nucleic acid coding sequence, each separated by a stretch of contiguous nucleotides that are not complementary to adjacent coding sequences, may inhibit the function of a BAHD acyltransferase nucleic acid. In general, each stretch of contiguous nucleotides is at least 4, 5, 6, 7, or 8 or more nucleotides in length. Non-complementary intervening sequences may be 1, 2, 3, or 4 nucleotides in length. One skilled in the art can easily use the calculated melting point of an oligonucleotide or nucleic acid hybridized to a nucleic acid target to estimate the degree of mismatching that will be tolerated for inhibiting or mutating expression of a particular target nucleic acid.

Inhibitory nucleic acids include, for example, ribozymes, antisense nucleic acids, interfering RNA, microRNA, small interfering RNA (siRNA), and combinations thereof.

An antisense nucleic acid molecule is typically single-stranded that is complementary to the target nucleic acid (a nucleic acid encoding a BAHD acyltransferase). The antisense nucleic acid may function in an enzyme-dependent manner or, more frequently, by steric blocking. Steric blocking antisense, which are RNase-H independent, interferes with gene expression or other mRNA-dependent cellular processes by binding to a target mRNA and getting in the way of other processes.

An antisense oligonucleotide can be complementary to a sense nucleic acid encoding a BAHD acyltransferase protein. For example, it may be complementary to the coding strand of a double-stranded cDNA molecule or complementary to an mRNA sequence. It may be complementary to an entire coding strand or to only a portion thereof. It may also be complementary to all or part of the noncoding region of a nucleic acid encoding a BAHD acyltransferase protein.

The non-coding region includes the 5' and 3' regions that flank the coding region, for example, the 5' and 3' untranslated sequences. An antisense oligonucleotide is generally at least six nucleotides in length, but may be about 8, 12, 15, 20, 25, 30, 35, 40, 45, or 50 nucleotides long. Longer oligonucleotides may also be used.

An antisense oligonucleotide may be prepared using methods known in the art, for example, by expression from an expression vector encoding the antisense oligonucleotide or from an expression cassette. For example, an antisense nucleic acid can be generated simply by flipping over the coding region of an mRNA, thereby allowing a regulatory sequence (e.g., a promoter) to transcribe the "wrong" DNA strand. The transcript so-produced is an antisense RNA, which will bind and inactivate the RNA produced by the normal gene.

RNA interference (also referred to as "RNA-mediated interference") (RNAi) is an effective mechanism by which gene expression can be reduced or eliminated. Double stranded RNA (dsRNA) or single stranded RNA has been observed to mediate the reduction, which is a multi-step process (for details of single stranded RNA methods and compositions see Martinez et al. *Cell* 110(5):563 (2002)). dsRNA activates post-transcriptional gene expression surveillance mechanisms that appear to function to defend cells from virus infection and transposon activity (Fire et al. (1998) *Nature* 391:806-811; Grishok et al. (2001) *Cell* 106:23-34; Ketting et al. (1999) *Cell* 99:133-141; Lin and Avery (1999) *Nature* 402:128-129; Montgomery et al. (1998) *Proc. Natl. Acad. Sci. USA.* 95:15502-15507; Sharp and Zamore (2000) *Science* 287:2431-2433; Tabara et al. (1999) *Cell* 99:123-132). Activation of these mechanisms targets mature, dsRNA-complementary mRNA for destruction. The double stranded RNA reduces the expression of the gene to which the dsRNA corresponds.

For example, RNAi can be made from two oligonucleotides consisting of partially complementary sequences. The oligonucleotides can be made recombinantly, for example, from one or two expression cassettes and/or expression vectors.

RNAi has some advantages including high specificity, ease of movement across cell membranes, and prolonged downregulation of the targeted gene. (Fire et al., 1998; Grishok et al., 2000; Ketting et al., 1999; Lin et al., 1999; Montgomery et al., 1998; Sharp et al., 2000; Tabara et al., 1999). Moreover, dsRNA has been shown to silence genes in a wide range of systems, including plants, protozoans, fungi, *C. elegans, Trypanasoma, Drosophila*, and mammals (Grishok et al., 2000; Sharp (1999) *Genes Dev.* 13:139-141; Sharp et al., 2000; Elbashir et al. (2001) *Nature* 411:494-498).

Small interfering RNAs (siRNAs) or short hairpin RNAs (shRNAs) can also be used to specifically reduce BAHD acyltransferase expression such that the level of BAHD acyltransferase polypeptides is reduced. siRNAs are double-stranded RNA molecules that mediate post-transcriptional gene silencing in a sequence-specific manner. See, for example, Hamilton & Baulcombe *Science* 286(5441):950-952 (1999); see also the world wide web at ambion.com (last retrieved May 10, 2006). Once incorporated into an RNA-induced silencing complex, siRNA mediate cleavage of the homologous endogenous mRNA transcript by guiding the complex to the homologous mRNA transcript, which is then cleaved by the complex.

For example, siRNA can be made from two partially or fully complementary oligonucleotides. Alternatively, short hairpin RNA (shRNA) can be employed that is a one oligonucleotide that forms a double-stranded region by folding back onto itself via a tight hairpin turn. The siRNA and/or shRNA may have sequence identity, sequence complementarity and/or be homologous to any region of the BAHD acyltransferase mRNA transcript. The region of sequence homology or complementarity may be 50 nucleotides or less in length, less than 45 nucleotides, less than 40 nucleotides, less than 35 nucleotides, less than 30 nucleotides, or less than 25 nucleotides in length. In some embodiments, the region of sequence homology or complementarity of a siRNA or shRNA may be about 21 to 23 nucleotides in length.

SiRNA is typically double stranded and may have two-nucleotide 3' overhangs, for example, 3' overhanging UU dinucleotides. Methods for designing siRNAs are known to those skilled in the art. See, for example, Elbashir et al. *Nature* 411:494-498 (2001); Harborth et al. *Antisense Nucleic Acid Drug Dev.* 13:83-106 (2003). Typically, a target site that begins with AA, has 3' UU overhangs for both the sense and antisense siRNA strands, and has an approximate 50% G/C content is selected. SiRNAs may be chemically synthesized, created by in vitro transcription, or expressed from an siRNA expression vector or a PCR expression cassette. See, e.g., the world wide web at ambion.com).

When a shRNA is expressed from an expression vector or a PCR expression cassette, the insert encoding the shRNA may be expressed as an RNA transcript that folds into an shRNA hairpin. Thus, the shRNA transcript may include a sense siRNA sequence that is linked to its reverse complementary antisense siRNA sequence by a spacer sequence that forms the loop of the hairpin as well as a string of Us at the 3' end. The loop of the hairpin may be of various lengths. For example, the loop can be 3 to 30 nucleotides in length, or 3 to 23 nucleotides in length. Examples of nucleotide sequences for the loop include AUG, CCC, UUCG, CCACC, CTCGAG, AAGCUU, CCACACC and UUCAAGAGA.

SiRNAs also may be produced in vivo by cleavage of double-stranded RNA introduced directly or via a transgene or virus.

The inhibitory nucleic acid may also be a ribozyme. A ribozyme is an RNA molecule with catalytic activity and is capable of cleaving a single-stranded nucleic acid such as an mRNA that has a homologous region. See, for example, Cech *Science* 236:1532-1539 (1987); Cech *Ann. Rev. Biochem.* 59:543-568 (1990); Cech *Curr. Opin. Struct. Biol.* 2:605-609 (1992); Couture and Stinchcomb *Trends Genet.* 12:510-515 (1996). A ribozyme may be used to catalytically cleave a BAHD acyltransferase mRNA transcript and thereby inhibit translation of the mRNA. See, for example, Haseloff et al., U.S. Pat. No. 5,641,673. A ribozyme having specificity for a BAHD acyltransferase nucleic acid may be designed based on the nucleotide sequences described herein. Methods of designing and constructing a ribozyme that can cleave an RNA molecule in trans in a highly sequence specific manner have been developed and described in the art. See, for example, Haseloff et al., *Nature* 334:585-591 (1988). A ribozyme may be targeted to a specific RNA by engineering a discrete "hybridization" region into the ribozyme. The hybridization region contains a sequence complementary to the target RNA that enables the ribozyme to specifically hybridize with the target. See, for example, Gerlach et al., EP 321,201. The target sequence may be a segment of about 5, 6, 7, 8, 9, 10, 12, 15, 20, or 50 contiguous nucleotides selected from a nucleic acid having any of the SEQ ID NO:16, 18, 19, 22, 23, 25, 26, 27, 28, 47-63 and 64 sequences. Longer complementary sequences may be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target. Thus, an existing ribozyme may be modified to target a BAHD acyltransferase mRNA by modifying the hybridization region of the ribozyme to include a sequence that is complementary to the target BAHD acyltransferase. Alternatively, an mRNA encoding a BAHD acyltransferase may be used to select a catalytic RNA having a specific ribonuclease activity from a pool of RNA molecules. See, for example, Bartel & Szostak *Science* 261: 1411-1418 (1993).

Inhibitory and mutating nucleic acids can be generated by recombinant means, for example, by expression from an expression cassette or expression vector. Alternatively, the inhibitory or mutating nucleic acids can also be prepared by chemical synthesis using naturally occurring nucleotides, modified nucleotides or any combinations thereof. In some embodiments, these nucleic acids are made from modified nucleotides or non-phosphodiester bonds, for example, that are designed to increase biological stability of the nucleic acid or to increase intracellular stability of the duplex formed between the inhibitory or mutating nucleic acids and endogenous nucleic acids. Naturally occurring nucleotides include the ribose or deoxyribose nucleotides adenosine, guanine, cytosine, thymine and uracil. Examples of modified nucleotides include 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil, 2-methylthio-N6-isopentenyladeninje, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine. Thus, inhibitory or mutating nucleic acids may include modified nucleotides, as well as natural nucleotides such as combinations of ribose and deoxyribose nucleotides, and inhibitory or mutating nucleic acids of the invention may be of any length sufficient to inhibit or mutate an endogenous nucleic acid.

Inhibiting, knocking down or knocking out XMTs in a plant will modulate or alter the monolignol ester conjugates in the plant, such as in the lignin of the plant. For example, inhibiting, knocking down or knocking out a pBMT, an FMT, a PMT, an AMT, and/or a BMT will decrease the absolute amount or relative proportion of monolignol p-hydroxybenzoates, monolignol ferulates, monolignol p-coumarates, monolignol acetates, and/or monolignol benzoates, respectively, in the plant, such as in the lignin of the plant.

Decreasing pBMT, PMT, AMT, and/or BMT activity in a plant can increase the hydrolytic digestibility of lignin in plants by increasing incorporation of monolignol ferulate in lignin as a result of reducing competition in the metabolic pathway involved with monolignol ferulate incorporation. Decreasing FMT activity in a plant can aid in the production of monolignol vanillate and/or monolignol syringate.

EXAMPLES

Introduction

Lignin is a copolymer with three primary subunits: p-hydroxyphenyl (H), guaiacyl (G), and syringyl (S), derived from the lignin monomers p-coumaryl, coniferyl, and sinapyl alcohols collectively known as monolignols (ML). In some plants a portion of the monolignols form ester conjugates through their γ-hydroxy group, these are termed monolignol conjugates (or monolignol ester conjugates). These monolignol conjugates are formed by a specific subclass of BAHD acyl transferases known as X-coenzyme A monolignol transferases (XMTs), where X-CoA is the thioester of a carboxylate-containing molecule. Introducing monolignol conjugates into plants that do not natively produce them, or increasing the amount of these subunits, has been shown to be able to reduce plant biomass recalcitrance and/or increase the amount of "clip-off" compounds (Rinaldi et al. (2016) Paving the way for lignin valorisation: Recent Advances in Bioengineering, Biorefining and Catalysis. *Angew Chem Int Ed Engl.* 55(29):8164-8215).

Zip-lignin technology has been developed in recent years as a method to improve the efficiency of conversion of biomass by reducing the recalcitrance toward deconstructing lignin. This has been demonstrated to work in poplar by introducing an FMT gene from *Angelica sinensis* (Wilkerson et al. (2014) Monolignol ferulate transferase introduces chemically labile linkages into the lignin backbone. *Science* 344:90-93). FMT makes monolignol ferulates by coupling monolignols to feruloyl-CoA via an ester linkage; the monolignol ferulates are in turn incorporated into lignins resulting in the introduction of ester bonds into the backbone of the lignin polymer.

One method of valorization is to increase the amount of easily clipped-off compounds for up-conversion to commodity chemicals, such as p-hydroxybenzoic acid and benzoic acid. These monolignol conjugates represent competing pathways in the production of monolignol ferulates. Reducing the production of benzoates or p-hydroxybenzoates could lead to an increased pool of substrates for zip-lignin formation. Alternatively, suppression of the production of monolignol ferulates could increase the amount of p-hydroxybenzoate in the cell walls increasing the potential yield in clip-off commodity chemicals.

Changes in monolignol transferase expression alters the plant metabolites. These alterations could produce plant lines with improved disease (fungal or bacterial) and/or insect resistance.

Methods

Selection of Gene Sequences

Gene sequences were obtained from NCBI GenBank. Protein sequence comparisons were made with NCBI BLAST+2.5.0 using default settings. The sequence identity is reported both as a percentage, as well as a fraction, where the numerator is the number of identical residues, and the denominator is the length of the matched region.

Cloning Vector

Genes were synthesized by GenScript Corporation (Piscataway, NJ) and cloned into the wheat germ cell-free expression vector, pEU (Sawasaki, T., Hasegawa, Y., Tsuchimochi, M., Kasahara, Y. and Endo, Y. (2000) Construction of an efficient expression vector for coupled transcription/translation in a wheat germ cell-free system. *Nucleic Acids*

Symposium Series, 9-10), which contains an SP6 promoter and omega enhancer sequence from tobacco mosaic virus. Plasmid DNA was purified from *E. coli* using a commercial purification kit, then treated with proteinase K and re-purified to remove residual RNAse activity and to concentrate the DNA. All genes synthesized for testing included an additional ATGGGA sequence on the 5' end of the native XMT coding sequence, thereby introducing a methionine and glycine on the N-terminus of each expressed protein.

Transcription

Messenger RNA was prepared by adding 1.6 U of SP6 RNA polymerase and 1 U of RNasin RNase inhibitor (Promega Corporation, Madison, WI) to plasmid DNA (0.2 mg/mL or higher) in the presence of 2.5 mM each of UTP, CTP, ATP, and GTP and 20 mM magnesium acetate, 2 mM spermidine HCl, 10 mM DTT, and 80 mM HEPES-KOH, pH 7.8. Transcription reactions were incubated at 37° C. for 4 h and visually monitored for the appearance of insoluble pyrophosphate byproducts, which are indicative of successful transcription.

Cell-Free Translation

The active enzymes were produced using a wheat germ cell-free translation bilayer method previously reported (Makino, S., Beebe, E. T., Markley, J. L. and Fox, B. G. (2014) Cell-free protein synthesis for functional and structural studies. *Methods in Molecular Biology*, 1091:161-178). Briefly, a translation reaction mixture consisting of 60 OD wheat germ extract (CellFree Sciences, Matsuyama, Japan), 0.04 mg/mL creatine kinase, 0.3 mM each amino acid, 12.6 mM HEPES-KOH, pH 7.8, 52.6 mM potassium acetate, 1.3 mM magnesium acetate, 0.2 mM spermidine HCl, 2.1 mM DTT, 0.6 mM ATP, 0.13 mM GTP, 8.4 mM creatine phosphate, and 0.003% sodium azide was prepared and combined with non-purified, fresh transcription at a ratio of 4 parts reaction mix to 1 part transcription. A feeding layer was prepared consisting of 0.3 mM each amino acid, 24 mM HEPES-KOH, pH 7.8, 100 mM potassium acetate, 2.5 mM magnesium acetate, 0.4 mM spermidine HCl, 4 mM DTT, 1.2 mM ATP, 0.25 mM GTP, 16 mM creatine phosphate, and 0.005% sodium azide, of which 125 µL was added to wells of a U-bottom 96-well plate. 25 µL of the denser translation reaction mixture was carefully layered below the feeding layer, forming a bilayer. The plate was sealed and incubated at 22° C. for 18 h. The fully-diffused 150 µL bilayer reaction was then harvested and used for expression analysis by SDS-PAGE, and activity screening.

Activity Screening of Enzymes

The enzyme mixture was screened for activity with acetyl-CoA, benzoyl-CoA, p-hydroxybenzoyl-CoA, feruloyl-CoA, and p-coumaroyl-CoA, and all three monolignols (hydroxycinnamyl, coniferyl, and sinapyl alcohol). Enzymes were tested in batches of ten enzymes against each CoA substrate and all three monolignols, alongside positive and negative controls, following the procedure previously reported (Withers, S., Lu, F., Kim, H., Zhu, Y., Ralph, J. and Wilkerson, C. G. (2012) Identification of a grass-specific enzyme that acylates monolignols with p-coumarate. *Journal of Biological Chemistry*, 287:8347-8355). If positive results were observed with one or more CoA substrate and the three monolignols, the enzymes in the batch were tested individually for activity. For individual reactions, the assay was initiated by adding 10 µL of wheat germ cell-free translation containing one of the enzymes at a concentration of 1.5-2 µM to a reaction containing 50 mM sodium phosphate buffer, pH 6, 1 mM dithiothreitol (DTT), 1 mM CoA thioester, 1 mM monolignol mixture (each monolignol at 1 mM concentration), and deionized water in a final volume of 50 µL. After a 30-min incubation, the reaction was stopped by the addition of an equal volume 100 mM hydrochloric acid. Reaction products were solubilized by adjusting the solution to 50% methanol. An identical assay with no enzyme added was performed for every reaction. Samples were filtered through 0.2 µm filters prior to analysis by LC-MS. The batch reactions were processed in a similar fashion, but the reaction volume was scaled up ten-fold to accommodate the ten volumes of different enzymes that were added.

Competition assays were used to ascertain which CoA substrates are preferentially used by the enzymes to couple with monolignols.

Mild Alkaline Hydrolysis to Quantify p-Hydroxybenzoate Levels

The determination of ester-linked carboxylic acids was performed on extract-free WCW using mild alkaline hydrolysis (2 M NaOH, 20 h at room temperature), following previously published procedures (Ralph, J., Hatfield, R. D., Quideau, S., Helm, R. F., Grabber, J. H. and Jung, H.-J. G. (1994) Pathway of p-coumaric acid incorporation into maize lignin as revealed by NMR. *Journal of the American Chemical Society* 116:9448-9456).

Results

Identification of monolignol acyltransferase enzymes and prediction of their activity has previously required the elucidation of candidate genes through identification of isolated enzymes or RNA expression. The candidate gene expression was then altered in the plant through its suppression/overexpression in genetically engineered plants or testing the enzyme heterologously expressed in cell-free wheat-germ, yeast, or *E. coli* systems and feeding the enzyme the substrates of interest. This is a time-consuming task that was performed one gene at a time and often with negative results. Here we utilized parallel gene identification and screening techniques to identify potential genes with in vivo activity for monolignol transferase activity. We first identified a pool of candidate genes (all the those with a conserved motif predicting acyltransferase activity) from the poplar genome. We then optimized the sequences for synthesis and produced the enzymes using the cell-free wheatgerm extract. Activities of the enzymes were determined through screening pools of 10 enzymes with potential cofactors (monolignols and acyl-CoAs) for the production of monolignol conjugates by LCMS methods. The enzyme pools with positive hits were flagged, and the 10 enzymes in the flagged group were individually tested for activity to identify which enzymes were active (and with which substrates).

In parallel, we used a more traditional approach of identifying gene candidates. Chemical analyses were used to screen plant species and cultivars to identify plants that have the highest and lowest levels of the chemical of interest (e.g., p-hydroxybenzoate). The data were then cross-referenced to RNA expression for the same plants to determine candidate genes.

Nine putative XMTs were identified: XMT1, XMT2, XMT3, XMT4, XMT5, XMT6, XMT7, XMT8, and XMT9. One of these functioned with broad XMT activity (XMT1), four functioned primarily as FMTs (XMT4, XMT7, XMT8, and XMT9), and three functioned primarily as pBMTs (XMT2, XMT3, and XMT6).

XMT1 was shown to have all of pBMT FMT, PMT, AMT, and BMT activities. A competition assay demonstrated equal amounts of activity as a pBMT and FMT, with less activity as a BMT and no detectable activity as an AMT or PMT.

XMT4, XMT7, XMT8, and XMT9 functioned primarily as FMTs. XMT9 functioned exclusively as an FMT. Both XMT 7 and XMT 8 additionally showed some PMT activity, and XMT4 additionally showed some PMT and BMT activity. For XMT4, XMT7 and XMT8, the results of the competition assay showed a very strong preference for feruloyl-CoA as a substrate over p-coumaroyl-CoA and/or benzoyl-CoA.

XMT2, XMT3, and XMT6 functioned primarily as pBMTs. XMT6 functioned exclusively as a pBMT. XMT2 and XMT3 additionally showed BMT and AMT functionality. In competition assays, both XMT2 and XMT3 preferentially functioned as pBMTs.

Figures 7A, 7B:
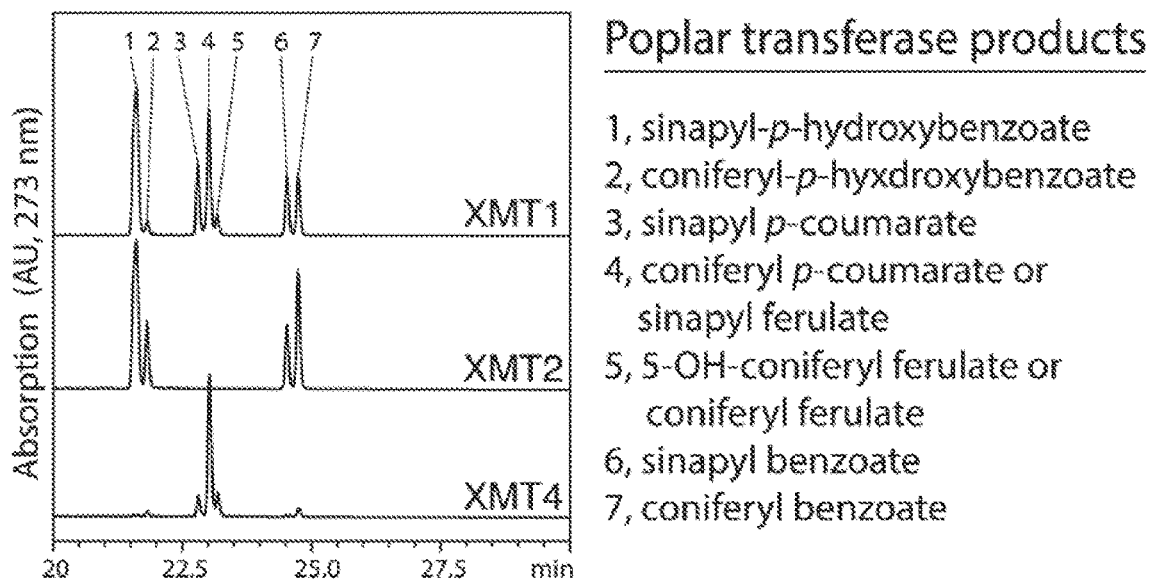
FIGS. 7A and 7B show results of screening XMT enzyme activity using a mixture of three monolignols and various CoA substrates.

FIGS. 7A and B summarize some of the above-mentioned activities of the XMTs.

Structurally, the XMTs fell into two major groups based on sequence identity and the motifs in the amino acid sequences. XMT1, XMT2, XMT3, XMT4, XMT5, and XMT6 formed the first group. XMT7, XMT8, and XMT9 formed the second group. XMT7 and XMT8 formed a subgroup within the second group. See FIGS. 3A-6. The sequence identities among the XMTs (native amino acid sequences, i.e., without the added methionine and glycine on the N-termini) are shown in Table 1.

TABLE 1

Sequence identities among the native XMT amino acid sequences.*

|  | XMT1 | XMT2 | XMT3 | XMT4 | XMT5 | XMT6 | XMT7 | XMT8 | XMT9 |
| --- | --- | --- | --- | --- | --- | --- | --- | --- | --- |
| XMT1 | 100% | 97.2% | 96.7% | 93.8% | 88.2% | 78.5% | 33.0% | 32.8% | 31.0% |
|  | 466/466 | 453/466 | 451/466 | 437/466 | 411/466 | 361/460 | 146/443 | 132/403 | 137/442 |
| XMT2 | 97.2% | 100% | 99.1% | 94.0% | 89.7% | 78.7% | 33.2% | 32.0% | 31.0% |
|  | 453/466 | 466/466 | 462/466 | 437/466 | 418/466 | 362/460 | 147/433 | 141/440 | 137/442 |
| XMT3 | 96.7% | 99.1% | 100% | 93.6% | 89.5% | 78.3% | 33.2% | 33.2% | 31.2% |
|  | 451/466 | 462/466 | 466/466 | 436/466 | 417/466 | 360/460 | 147/433 | 147/433 | 138/442 |
| XMT4 | 93.8% | 94.0% | 93.6% | 100% | 86.9% | 76.5% | 33.2% | 32.7% | 31.2% |
|  | 437/466 | 437/466 | 436/466 | 466/466 | 405/466 | 361/460 | 147/433 | 144/440 | 137/442 |
| XMT5 | 88.2% | 89.7% | 89.5% | 86.9% | 100% | 76.5% | 31.8% | 31.9% | 31% |
|  | 411/466 | 418/466 | 417/466 | 405/466 | 466/466 | 354/463 | 142/477 | 141/442 | 136/442 |
| XMT6 | 78.5% | 78.7% | 78.3% | 76.5% | 76.5% | 100% | 30.6% | 31.5% | 29.0% |
|  | 361/460 | 362/460 | 360/460 | 361/460 | 354/463 | 470/470 | 137/447 | 138/438 | 128/442 |
| XMT7 | 33.0% | 33.2% | 33.2% | 33.2% | 31.8% | 30.6% | 100% | 75.9% | 46.7% |
|  | 146/443 | 147/433 | 147/433 | 147/433 | 142/477 | 137/447 | 432/432 | 328/432 | 203/432 |
| XMT8 | 32.8% | 32.0% | 31.7% | 32.7% | 31.9% | 31.5% | 75.9% | 100% | 47.9% |
|  | 132/403 | 141/440 | 140/442 | 144/440 | 141/442 | 138/438 | 328/432 | 444/444 | 207/432 |
| XMT9 | 31.0% | 31.0% | 31.2% | 31.2% | 31% | 29.0% | 46.7% | 47.9% | 100% |
|  | 137/442 | 137/442 | 138/442 | 137/442 | 136/442 | 128/442 | 203/432 | 207/432 | 441/441 |

*Table is symmetric about the diagonal.

To determine in planta activity, XMT1, XMT2, XMT3, and XMT6 have been overexpressed in poplar using ubiquitous and tissue-specific promoters. *Agrobacterium*-mediated transformation of hybrid poplar (*Populus alba*×*grandidentata* P39) was performed according to standard transformation protocols as detailed in Wilkerson et al. (Wilkerson et al. (2014) Monolignol ferulate transferase introduces chemically labile linkages into the lignin backbone. *Science* 344:90-93). The XMT genes were cloned into a native version of the pK7WG2 plant expression vector (Karimi M, Inzé Depicker A. (2002) GATEWAY™ vectors for *Agrobacterium*-mediated plant transformation. *Trends in Plant Science* 7(5):193-195) containing the 35S promoter, a modified version containing the *Arabidopsis* cinnamate-4-hydroxylase (C4H) promoter sequence, and a modified version containing the secondary cell wall-specific CesA promoter sequence (Wilkerson et al. (2014) Monolignol ferulate transferase introduces chemically labile linkages into the lignin backbone. *Science* 344:90-93) to drive the expression of the various XMT genes. These plasmids were transferred into *Agrobacterium tumefaciens* strain EHA105, which was used in the transformation of poplar leaf disks. After 2 days of co-cultivation with *Agrobacterium*, followed by 4-8 weeks of callus formation under selection with kanamycin, transgenic shoots were recovered and propagated in tissue culture. Following confirmation of gene insertion by screening of genomic DNA and gene expression by real-time quantitative PCR, transgenic poplar lines were transferred to soil in a glass house and grown for 4 months prior to harvesting.

Figure 8A:
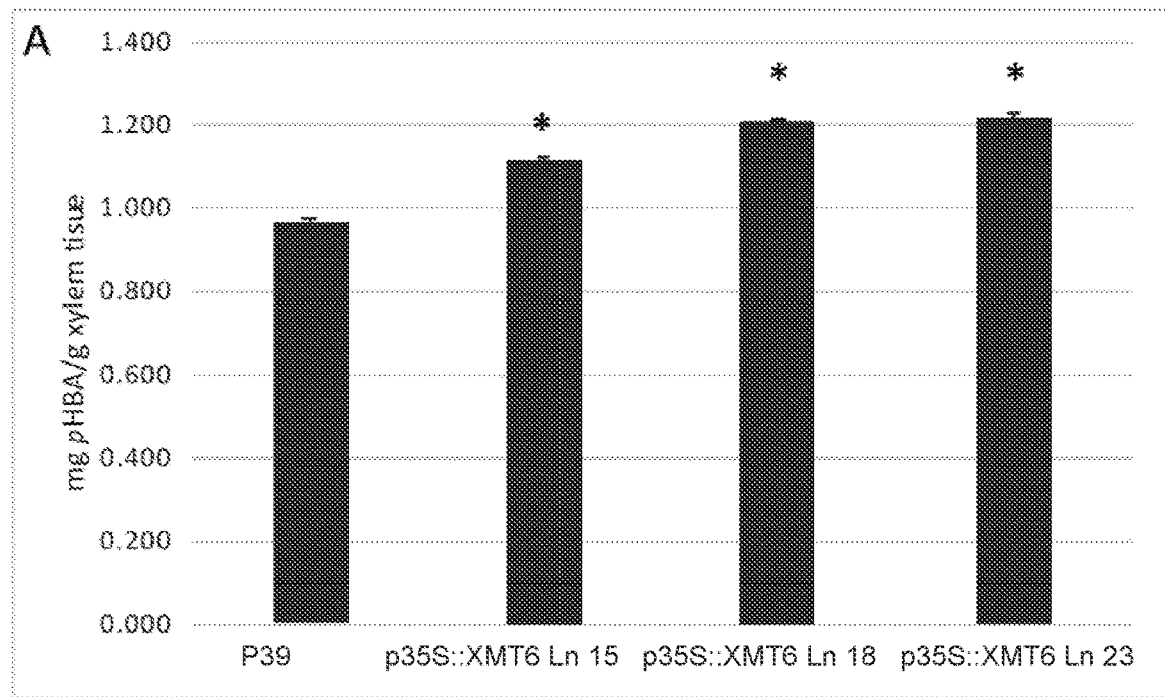
FIGS. 8A and 8B show increased release of p-hydroxybenzoate from xylem tissues in poplar following alkaline hydrolysis resulting from the overexpression of XMT6 under the control of the 35S promoter (FIG. 8A) or the C4H promoter (FIG. 8B).
Figure 8B:
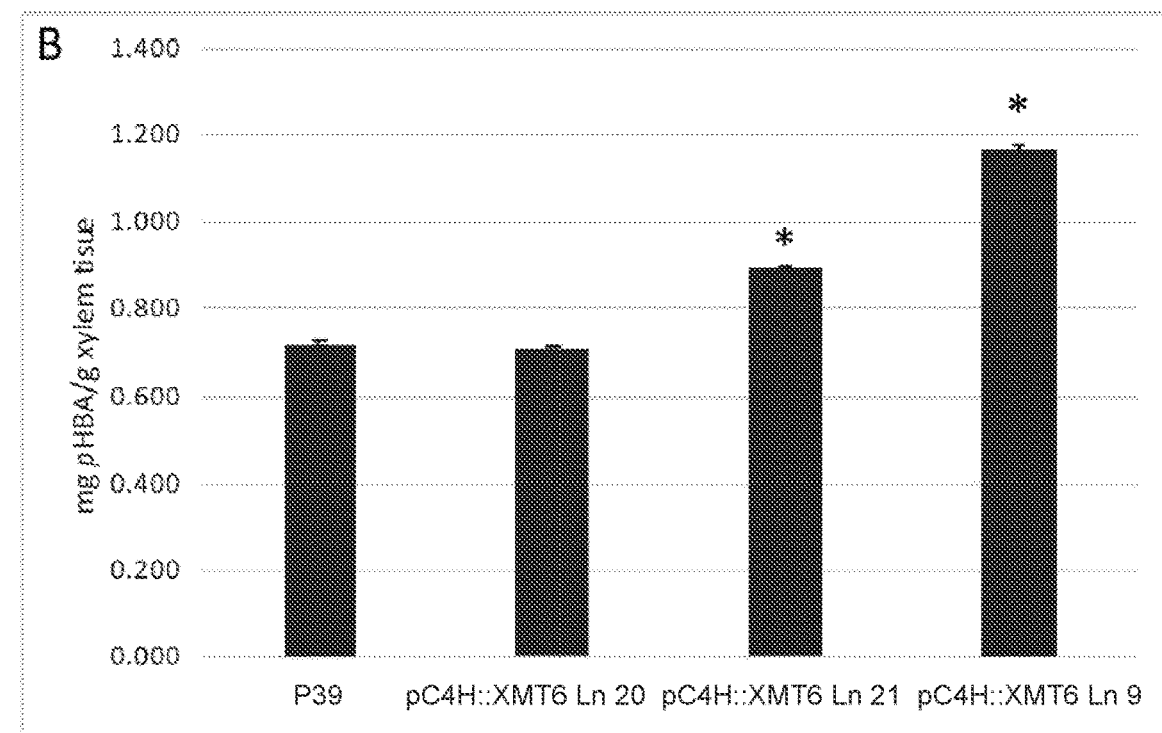
Figure 9:
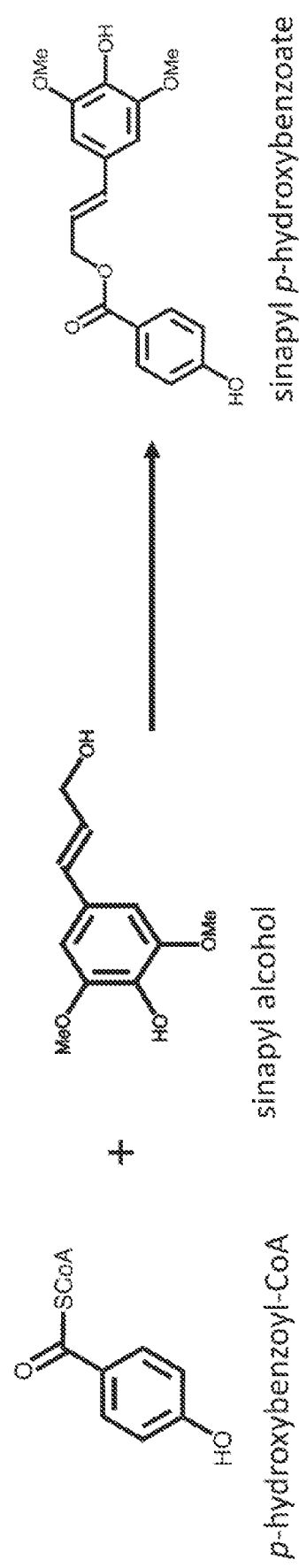
FIG. 9 shows the synthesis of sinapyl p-hydroxybenzoate from p-hydroxybenzoyl-CoA and sinapyl alcohol through the activity of pHBMT enzymes.

The activity of XMT6 has been characterized in poplar. Xylem tissue in transgenic trees expressing XMT6 under the control of the 35S ubiquitous promoter or the xylem-specific (lignin biosynthetic pathway) C4H promoter were analyzed for changes in the quantity of p-hydroxybenzoate (pHBA) monolignol conjugates. Alkaline hydrolysis of the ground and solvent extracted xylem tissue showed significantly higher levels of pHBA in three events with the 35S promoter and two events with the C4H promoter compared to the P39 control trees (FIGS. 8A and 8B), Derivatization followed by reductive cleavage (DFRC), a chemical degradative method, and two-dimensional nuclear magnetic resonance (2D NMR) analysis, corroborated these results. These results indicate that XMT6 exhibits p-BMT activity in planta (FIG. 9).

XMT2 under the control of each of the 35S, CesA, and C4H promoters also similarly increased pHBA in the poplar, particularly in the cell wall fraction.

The activities of XMT1 and XMT3 in planta will be similarly characterized. It is predicted that XMT1 will show p-BMT, PMT, FMT, BMT, and/or AMT activity in planta and that XMT3 will show p-BMT and/or BMT activity in planta.

The genes expressing XMT1, XMT2, XMT3, and XMT6 have also been transformed into *Arabidopsis*, which does not naturally produce monolignol conjugates (or are present at very low levels). When mature, the transgenic *Arabidopsis* will be examined by chemical analyses, such as Derivatization followed by Reductive Cleavage (DFRC) (Regner, M., Bartuce, A., Padmakshan, D., Ralph, J. and Karlen, S. D. (2018) Reductive cleavage method for quantitation of monolignols and low-abundance monolignol conjugates. *ChemSusChem* 11:1600-1605), alkaline hydrolysis (Karlen, S. D., Smith, R. A., Kim, H., Padmakshan, D., Bartuce, A., Mobley, J. K., Free, H. C. A., Smith, B. G., Harris, P. J. and Ralph, J. (2017) Highly decorated lignins occur in leaf base cell walls of the Canary Island date palm *Phoenix canariensis.* Plant Physiology 175:1058-1067; Smith, D. C. C. (1955) p-Hydroxybenzoates groups in the lignin of Aspen (*Populus tremula*). *Journal of the Chemical Society* 2347) and 2D-NMR (Mansfield, S. D., Kim, H., Lu, F. and Ralph, J. (2012) Whole plant cell wall characterization using solution-state 2D-NMR. *Nature Protocols,* 7:1579-1589) to quantify the benzoate, p-hydroxybenzoate, p-coumarate, and ferulate content of the lignin. We anticipate that these enzymes will function as pBMTs in planta, which should be indicated with a significant increase in pBA production and incorporation into the lignin polymer.

XMT4, XMT7, XMT8, and XMT9 will similarly be transformed into *Arabidopsis* and overexpressed in poplar. It is predicted that the in vitro FMT activity will correspond to changes in ferulate production and incorporation into the lignin in planta.

The various XMTs described herein are predicted to have certain activities and advantages in plants.

As a universal transferase, XMT1 is predicted to have several advantages in planta over other transferases. The universal transferase will generate plants that are predicted to have a greater proportion of soluble metabolites and cell-wall-bound phenolics that can be funneled to a single compound in microbial digestion to value-added products. Finally, phenolic conjugates, by different mechanisms, enhance cell wall digestibility by cellulases (and polysaccharidases, in general), we anticipate that such a gene will still produce digestibility-improved plant lines, but will allow the plant to tune its lignin acylation types according to its own criteria.

Selective p-BMT transferases such as XMT6 are predicted to increase the amount of p-hydroxybenzoate, but not alter the level of other phenolics. This is important in reducing undesired impurities in plant extracts to generate a renewable source of p-hydroxybenzoate.

Selective transferase activity for both substituted and unsubstituted benzoate, as exhibited by XMT2 and XMT3, is predicted to enable the engineering of plant lines that contain elevated levels of p-hydroxybenzoate, benzoate, and other benzoate derivatives. This, in turn, will increase the value of the biomass as a source of renewable benzoates.

Selectivity for FMT activity, as exhibited by XMT9, is predicted to assist in generating plants with only ferulate conjugates. This is crucial for maximizing the effect that zip-lignin technology has on improving cell wall digestion. This is also essential for producing only one type of phenolic acid to reduce the cost for the envisioned commercial scale production of ferulic acid or other phenolic acids.

Selectivity for PMT and FMT activities, as exhibited by XMT7 and XMT8, is predicted to generate plants that have the maximum amount of cinnamic acid functionality. This is desirable as a means for reducing cell-wall recalcitrance and increasing the titers in funneling phenolic plant extracts through microbial up-conversion to renewable sources of both liquid fuels and commodity chemicals (e.g., plastic and pharmaceutical precursors).

Looser selectivity for mainly FMT activity, as exhibited by XMT4, is predicted to be advantageous in plants that produce both cinnamate and benzoate derivatizes (e.g., palm trees, poplars, and willows). This transferase will reduce cell-wall recalcitrance through higher levels of zip-lignin technology, but also contain higher levels of phenolics that can be funneled through microbial up-conversion to value-added products.

STATEMENTS OF EMBODIMENTS OF THE INVENTION

The following statements of the invention are intended to summarize some aspects of the invention according to the foregoing description given in the specification.

Statements of a First Set of Embodiments of the Invention

1. An isolated or recombinant nucleic acid encoding a BAHD acyltransferase, wherein the nucleic acid encodes a BAHD acyltransferase polypeptide comprising a sequence substantially identical to SEQ ID NO:2, SEQ ID NO:4, SEQ ID NO:6, SEQ ID NO:8, SEQ ID NO:12, SEQ ID NO:14, SEQ ID NO:16, or SEQ ID NO:18, and/or wherein the nucleic acid can selectively hybridize to a DNA with a SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence.

2. The isolated nucleic acid of statement 1, wherein the nucleic acid selectively hybridizes to a DNA with a SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence under stringent hybridization conditions.

3. The isolated nucleic acid of statement 2, wherein the stringent hybridization conditions comprise a wash in 0.1× SSC, 0.1% SDS at 65° C.

4. The isolated nucleic acid of any of statements 1-3, wherein the nucleic acid that selectively hybridizes to a DNA with a SEQ ID NO:1, SEQ ID NO:3, SEQ ID NO:5, SEQ ID NO:7, SEQ ID NO:11, SEQ ID NO:13, SEQ ID NO:15, or SEQ ID NO:17 sequence has at least about 70% sequence identity with SEQ ID NO:1, SEQ ID NO:3, SEQ ID NO:5, SEQ ID NO:7, SEQ ID NO:11, SEQ ID NO:13, SEQ ID NO:15, or SEQ ID NO:17.

5. The isolated nucleic acid of any of statements 1-4, wherein the nucleic acid encodes a BAHD acyltransferase that can catalyze the synthesis of a monolignol ester conjugate.

6. The isolated nucleic acid of statement 5, wherein the monolignol is coniferyl alcohol, p-coumaryl alcohol, sinapyl alcohol or a combination thereof.

7. The isolated nucleic acid of any of statements 1-6, wherein the nucleic acid encodes a BAHD acyltransferase polypeptide with a sequence substantially identical to SEQ ID NO:2, SEQ ID NO:4, SEQ ID NO:6, SEQ ID NO:8, SEQ ID NO:12, SEQ ID NO:14, SEQ ID NO:16, or SEQ ID NO:18.

8. The isolated nucleic acid of any of statements 1-7, wherein the nucleic acid encodes a BAHD acyltransferase that can catalyze the synthesis of a monolignol ester conjugate with at least about 50% of the activity of a BAHD acyltransferase with the SEQ ID NO:2, SEQ ID NO:4, SEQ ID NO:6, SEQ ID NO:8, SEQ ID NO:12, SEQ ID NO:14, SEQ ID NO:16, or SEQ ID NO:18 sequence.

9. A transgenic plant cell comprising the isolated nucleic acid of any of statements 1-8.

10. A transgenic plant comprising the plant cell of statement 9 or the isolated nucleic acid of any of statements 1-8.

11. An expression cassette comprising the BAHD acyltransferase nucleic acid of any of statements 1-8 operably linked to a promoter functional in a host cell.

12. The expression cassette of statement 11, which further comprises a selectable marker gene.

13. The expression cassette of statement 11 or 12, further comprising plasmid DNA.

14. The expression cassette of any of statements 11-13, wherein the expression cassette is within an expression vector.

15. The expression cassette of any of statements 11-14, wherein the promoter is a promoter functional during plant development or growth.

16. The expression cassette of any of statements 11-15, wherein the promoter is a poplar xylem-specific secondary cell wall specific cellulose synthase 8 promoter, an *Arabidopsis* C4H lignin-specific promoter, cauliflower mosaic virus promoter, Z10 promoter from a gene encoding a 10 kD zein protein, Z27 promoter from a gene encoding a 27 kD zein protein, pea rbcS gene or actin promoter from rice.

17. A plant cell comprising the expression cassette of any of statements 11-16.

18. The plant cell of statement 17, wherein the plant cell is a monocot cell.

19. The plant cell of statement 17, wherein the plant cell is a maize, grass or softwood cell.

20. The plant cell of statement 17, wherein the plant cell is a dicot cell.

21. The plant cell of statement 17, wherein the plant cell is a hardwood cell.

22. A plant comprising the expression cassette of any of statements 11-16.

23. The plant of statement 22, wherein the plant is a monocot.

24. The plant of statement 22, wherein the plant is a grass, maize or softwood.

25. The plant of statement 22, wherein the plant is a gymnosperm.

26. The plant of statement 22, wherein the plant is a dicot.

27. The plant of statement 22, wherein the dicot is a hardwood.

28. A method for incorporating monolignol ester conjugates into lignin of a plant, comprising:
  a) stably transforming plant cells with the expression cassette of any of statements 11-16 to generate transformed plant cells;
  b) regenerating the transformed plant cells into at least one transgenic plant, wherein the BAHD acyltransferase is expressed in at least one transgenic plant in an amount sufficient to incorporate monolignol ester conjugates into the lignin of the transgenic plant.

29. The method of statement 28, wherein the transgenic plant is fertile.

30. The method of statement 28 or 29, further comprising recovering transgenic seeds from the transgenic plant, wherein the transgenic seeds comprise the nucleic acid encoding a BAHD acyltransferase.

31. The method of any of statements 28-30, wherein the plant is a monocot.

32. The method of any of statements 28-31, wherein the plant is a grass, maize or softwood plant.

33. The method of any of statements 28-32, wherein the plant is a gymnosperm.

34. The method of statement 28, wherein the plant is a dicot.

35. The method of statement 34, wherein the dicot plant is a hardwood.

36. The method of any of statements 28-35, further comprising breeding a fertile transgenic plant to yield a progeny plant that has an altered content of monolignol ester conjugates in the lignin of the progeny plant relative to the corresponding untransformed plant.

37. The method of any of statements 28-36, further comprising breeding a fertile transgenic plant to yield a progeny plant that has an altered content of monolignol ester conjugates in the lignin of the progeny plant as a dominant trait while still maintaining functional agronomic characteristics relative to the corresponding untransformed plant.

38. The method of any of statements 28-37, wherein the transformed plant cell is transformed by a method selected from the group consisting of electroporation, microinjection, microprojectile bombardment, and liposomal encapsulation.

39. The method of any of statements 28-38, further comprising stably transforming the plant cell with at least one selectable marker gene.

40. A fertile transgenic plant having an increased percent of monolignol ester conjugates in the plant's lignin, the genome of which is stably transformed by the nucleic acid of any of statements 1-8, wherein the nucleic acid is operably linked to a promoter functional in a host cell, and wherein the BAHD acyltransferase nucleic acid is transmitted through a complete normal sexual cycle of the transgenic plant to the next generation.

41. The plant of statement 40, wherein the plant is a monocot.

42. The plant of statement 40, wherein the plant is a grass, maize or softwood.

43. The plant of statement 40, wherein the plant is a gymnosperm.

44. The plant of statement 40, wherein the plant is a dicot.

45. The plant of statement 40, wherein the content of monolignol ester conjugates in the plant's lignin is altered relative to the corresponding untransformed plant.

46. The plant of any of statements 40-45, wherein the percent of monolignol ester conjugates in the plant's lignin is increased by at least 1% relative to the corresponding untransformed plant.

47. The plant of any of statements 40-46, wherein the percent of monolignol ester conjugates in the plant's lignin is increased by at least 2-5% relative to the corresponding untransformed plant.

48. A lignin isolated from a transgenic plant comprising the isolated nucleic of any of statements 1-8.

49. A method of making a product from a transgenic plant comprising:
  (a) providing or obtaining a transgenic plant that includes an isolated nucleic acid encoding a BAHD acyltransferase comprising the isolated nucleic of any of statements 1-8; and
  (b) processing the transgenic plant's tissues under conditions sufficient to digest the lignin; and thereby generate the product from the transgenic plant,
  wherein the transgenic plant's tissues comprise lignin having an altered content of monolignol ester conjugates relative to a corresponding untransformed plant.

50. The method of statement 49, wherein the conditions sufficient to digest the lignin comprise conditions sufficient to cleave ester bonds.

51. The method of statement 49 or 50, wherein the conditions sufficient to digest the lignin comprise mildly alkaline conditions.

52. The method of any of statements 49-51, wherein the conditions sufficient to digest the lignin comprise contacting the transgenic plant's tissues with ammonia for a time and a temperature sufficient to cleave ester bonds.

53. The method of any of statements 49-52, wherein the conditions sufficient to digest the lignin would not cleave substantially any of the ether and carbon-carbon bonds in

Statements of a Second Set of Embodiments of the Invention

1A. A transgenic plant comprising a knockdown or knockout of the plant's endogenous BAHD acyltransferase gene.

3A. The transgenic plant of statement 1A, wherein the endogenous BAHD acyltransferase gene can hybridize to a nucleic acid with a sequence selected from the group consisting of SEQ ID NO:1, SEQ ID NO:3, SEQ ID NO:5, SEQ ID NO:7, SEQ ID NO:11, SEQ ID NO:13, SEQ ID NO:15, and SEQ ID NO:17.

4A. The transgenic plant of statement 1A, wherein the endogenous BAHD acyltransferase gene has at least 50% sequence identity with a nucleic acid sequence selected from the group consisting of SEQ ID NO:1, SEQ ID NO:3, SEQ ID NO:5, SEQ ID NO:7, SEQ ID NO:11, SEQ ID NO:13, SEQ ID NO:15, and SEQ ID NO:17.

5A. The transgenic plant of statement 1A, wherein the knockdown or knockout is a mutation selected from the group consisting of a point mutation, a deletion, a missense mutation, insertion or a nonsense mutation in the endogenous BAHD acyltransferase gene.

6A. The transgenic plant of statement 1A, wherein the knockdown or knockout mutation comprises a point mutation, a deletion, a missense mutation, insertion or a nonsense mutation in the endogenous BAHD acyltransferase gene encoding a polypeptide with at least 60% sequence identity to an amino acid sequence selected from the group consisting of SEQ ID NO:2, SEQ ID NO:4 SEQ ID NO:6, SEQ ID NO:8, SEQ ID NO:12, SEQ ID NO:14, SEQ ID NO:16, and SEQ ID NO:18.

7A. The transgenic plant of statement 1A, wherein expression of at least one inhibitory nucleic acid comprising a nucleic acid sequence with at least 90% sequence identity to either strand of a nucleic acid comprising a sequence selected from the group consisting of SEQ ID NO:1, SEQ ID NO:3, SEQ ID NO:5, SEQ ID NO:7, SEQ ID NO:11, SEQ ID NO:13, SEQ ID NO:15, and SEQ ID NO:17 comprises the knockdown or knockout.

8A. The transgenic plant of statement 1A, wherein the knockdown or knockout reduces BAHD acyltransferase activity in the plant.

9A. The transgenic plant of statement 1A, wherein the knockdown or knockout reduces acylation of monolignols, where the monolignols are selected from the group consisting of p-coumaryl alcohol, coniferyl alcohol and sinapyl alcohol.

10A. The transgenic plant of statement 1A, wherein the knockdown or knockout reduces production of at least one type of monolignol ester conjugate 11A. The transgenic plant of statement 1A, wherein the plant is fertile.

12A. One or more seeds from the transgenic plant of statement 1A.

13A. An inhibitory nucleic acid comprising a DNA or RNA comprising a nucleic acid sequence with at least 90% sequence identity to either strand of a nucleic acid comprising a sequence selected from the group consisting of SEQ ID NO:1, SEQ ID NO:3, SEQ ID NO:5, SEQ ID NO:7, SEQ ID NO:11, SEQ ID NO:13, SEQ ID NO:15, and SEQ ID NO:17.

14A. An expression cassette comprising the inhibitory nucleic acid of statement 13A operably linked to a promoter functional in a host cell.

15A. An isolated or recombinant cell comprising the inhibitory nucleic acid of statement 17A or the expression cassette of statement 14A.

16A. The isolated or recombinant cell of statement 15A, which is a microorganism or a plant cell.

17A. A transgenic plant comprising the isolated or recombinant cell of statement 16A.

18A. A method of incorporating monolignol ferulates into lignin of a plant comprising: a) obtaining one or more plant cells having a knockout or knockdown of the plant cells' endogenous BAHD acyltransferase gene; b) regenerating one or more of the plant cells into at least one transgenic plant.

19A. A method of inhibiting expression and/or translation of BAHD acyltransferase RNA in a plant cell comprising: a) contacting or transforming plant cells with the expression cassette of statement 14A to generate transformed plant cells; b) regenerating the transformed plant cells into at least one transgenic plant, wherein an inhibitory nucleic acid adapted to inhibit the expression and/or translation of a BAHD acyltransferase mRNA is expressed in at least one transgenic plant in an amount sufficient to incorporate monolignol ferulates into the lignin of the transgenic plant.

lignin from a corresponding plant that does not contain the isolated nucleic acid encoding the BAHD acyltransferase.

We claim:

1. A recombinant nucleic acid comprising a nucleic acid segment that encodes:
   a BAHD acyltransferase polypeptide with at least 95% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, benzoyl-CoA:monolignol transferase (BMT) activity, or any combination thereof;
   a BAHD acyltransferase polypeptide with at least 95% amino acid sequence identity to SEQ ID NO:4 that exhibits pBMT activity, AMT activity, BMT activity, or any combination thereof;
   a BAHD acyltransferase polypeptide with at least 95% amino acid sequence identity to SEQ ID NO:6 that exhibits pBMT activity, AMT activity, BMT activity, or any combination thereof;
   a BAHD acyltransferase polypeptide with at least 95% amino acid sequence identity to SEQ ID NO:8 that exhibits FMT activity, PMT activity, BMT activity, or any combination thereof;
   a BAHD acyltransferase polypeptide with at least 95% amino acid sequence identity to SEQ ID NO:12 that exhibits pBMT activity;
   a BAHD acyltransferase polypeptide with at least 95% amino acid sequence identity to SEQ ID NO:14 that exhibits FMT activity, PMT activity, or any combination thereof;
   a BAHD acyltransferase polypeptide with at least 95% amino acid sequence identity to SEQ ID NO:16 that exhibits FMT activity, PMT activity, or any combination thereof; or
   a BAHD acyltransferase polypeptide with at least 95% amino acid sequence identity to SEQ ID NO:18 that exhibits FMT activity,
   wherein the nucleic acid segment is operably linked to a heterologous promoter, wherein the promoter is a promoter functional or active during plant development or growth.

2. The recombinant nucleic acid of claim 1, wherein the promoter is a promoter functional or active in woody tissues of a plant.

3. A recombinant plant cell comprising a recombinant nucleic acid, wherein:
   the recombinant nucleic acid comprises a nucleic acid segment that encodes;
   a BAHD acyltransferase polypeptide with at least 95% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, benzoyl-CoA:monolignol transferase (BMT) activity, or any combination thereof;
   a BAHD acyltransferase polypeptide with at least 95% amino acid sequence identity to SEQ ID NO:4 that exhibits pBMT activity, AMT activity, BMT activity, or any combination thereof;
   a BAHD acyltransferase polypeptide with at least 95% amino acid sequence identity to SEQ ID NO:6 that exhibits pBMT activity, AMT activity, BMT activity, or any combination thereof;
   a BAHD acyltransferase polypeptide with at least 95% amino acid sequence identity to SEQ ID NO:8 that exhibits FMT activity, PMT activity, BMT activity, or any combination thereof;
   a BAHD acyltransferase polypeptide with at least 95% amino acid sequence identity to SEQ ID NO:12 that exhibits pBMT activity;
   a BAHD acyltransferase polypeptide with at least 95% amino acid sequence identity to SEQ ID NO:14 that exhibits FMT activity, PMT activity, or any combination thereof;
   a BAHD acyltransferase polypeptide with at least 95% amino acid sequence identity to SEQ ID NO:16 that exhibits FMT activity, PMT activity, or any combination thereof; or
   a BAHD acyltransferase polypeptide with at least 95% amino acid sequence identity to SEQ ID NO:18 that exhibits FMT activity;
   the nucleic acid segment is operably linked to a heterologous promoter functional or active during plant development or growth; and
   the plant cell comprises a genome stably transformed with the recombinant nucleic acid.

4. A plant comprising a recombinant nucleic acid, wherein the recombinant nucleic acid comprises a nucleic acid segment that encodes a BAHD acyltransferase polypeptide with at least 95% amino acid sequence identity to SEQ ID NO:2, SEQ ID NO:4, SEQ ID NO:6, SEQ ID NO:8, SEQ ID NO:12, SEQ ID NO:14, SEQ ID NO:16, or SEQ ID NO:18, wherein the nucleic acid segment is operably linked to a heterologous promoter functional or active during plant development or growth, and wherein the plant comprises lignin having a modified content of monolignol ester conjugates compared to a control plant of the same species lacking the recombinant nucleic acid.

5. The plant of claim 4, wherein the genome of the plant is stably transformed with the recombinant nucleic acid.

6. A plant seed comprising a recombinant nucleic acid, wherein:
the recombinant nucleic acid comprises a nucleic acid segment that encodes:
a BAHD acyltransferase polypeptide with at least 95% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, benzoyl-CoA:monolignol transferase (BMT) activity, or any combination thereof;
a BAHD acyltransferase polypeptide with at least 95% amino acid sequence identity to SEQ ID NO:4 that exhibits pBMT activity, AMT activity, BMT activity, or any combination thereof;
a BAHD acyltransferase polypeptide with at least 95% amino acid sequence identity to SEQ ID NO:6 that exhibits pBMT activity, AMT activity, BMT activity, or any combination thereof;
a BAHD acyltransferase polypeptide with at least 95% amino acid sequence identity to SEQ ID NO:8 that exhibits FMT activity, PMT activity, BMT activity, or any combination thereof;
a BAHD acyltransferase polypeptide with at least 95% amino acid sequence identity to SEQ ID NO:12 that exhibits pBMT activity;
a BAHD acyltransferase polypeptide with at least 95% amino acid sequence identity to SEQ ID NO:14 that exhibits FMT activity, PMT activity, or any combination thereof;
a BAHD acyltransferase polypeptide with at least 95% amino acid sequence identity to SEQ ID NO:16 that exhibits FMT activity, PMT activity, or any combination thereof; or
a BAHD acyltransferase polypeptide with at least 95% amino acid sequence identity to SEQ ID NO:18 that exhibits FMT activity; and
the nucleic acid segment is operably linked to a heterologous promoter functional or active during plant development or growth.

7. The plant of claim 4, wherein:
the nucleic acid segment encodes:
a BAHD acyltransferase polypeptide with at least 95% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, benzoyl-CoA:monolignol transferase (BMT) activity, or any combination thereof;

a BAHD acyltransferase polypeptide with at least 95% amino acid sequence identity to SEQ ID NO:4 that exhibits pBMT activity, AMT activity, BMT activity, or any combination thereof;
a BAHD acyltransferase polypeptide with at least 95% amino acid sequence identity to SEQ ID NO:6 that exhibits pBMT activity, AMT activity, BMT activity, or any combination thereof;
a BAHD acyltransferase polypeptide with at least 95% amino acid sequence identity to SEQ ID NO:8 that exhibits FMT activity, PMT activity, BMT activity, or any combination thereof;
a BAHD acyltransferase polypeptide with at least 95% amino acid sequence identity to SEQ ID NO:12 that exhibits pBMT activity;
a BAHD acyltransferase polypeptide with at least 95% amino acid sequence identity to SEQ ID NO:14 that exhibits FMT activity, PMT activity, or any combination thereof;
a BAHD acyltransferase polypeptide with at least 95% amino acid sequence identity to SEQ ID NO:16 that exhibits FMT activity, PMT activity, or any combination thereof; or
a BAHD acyltransferase polypeptide with at least 95% amino acid sequence identity to SEQ ID NO:18 that exhibits FMT activity; and
the plant comprises a genome stably transformed with the recombinant nucleic acid.

8. The recombinant nucleic acid of claim 1, wherein the nucleic acid segment encodes a BAHD acyltransferase polypeptide with at least 95% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, benzoyl-CoA:monolignol transferase (BMT) activity, or any combination thereof.

9. The recombinant nucleic acid of claim 1, wherein the nucleic acid segment encodes a BAHD acyltransferase polypeptide with at least 99% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, and benzoyl-CoA:monolignol transferase (BMT) activity.

10. The recombinant nucleic acid of claim 1, wherein the nucleic acid segment encodes a BAHD acyltransferase polypeptide with at least 95% amino acid sequence identity to SEQ ID NO:4 that exhibits pBMT activity, AMT activity, BMT activity, or any combination thereof.

11. The recombinant nucleic acid of claim 1, wherein the nucleic acid segment encodes a BAHD acyltransferase polypeptide with at least 99% amino acid sequence identity to SEQ ID NO:4 that exhibits pBMT activity, AMT activity, and BMT activity.

12. The recombinant nucleic acid of claim 1, wherein the nucleic acid segment encodes a BAHD acyltransferase polypeptide with at least 95% amino acid sequence identity to SEQ ID NO:6 that exhibits pBMT activity, AMT activity, BMT activity, or any combination thereof.

13. The recombinant nucleic acid of claim 1, wherein the nucleic acid segment encodes a BAHD acyltransferase polypeptide with at least 99% amino acid sequence identity to SEQ ID NO:6 that exhibits pBMT activity, AMT activity, and BMT activity.

14. The recombinant nucleic acid of claim 1, wherein the nucleic acid segment encodes a BAHD acyltransferase polypeptide with at least 95% amino acid sequence identity to SEQ ID NO:8 that exhibits FMT activity, PMT activity, BMT activity, or any combination thereof.

15. The recombinant nucleic acid of claim 1, wherein the nucleic acid segment encodes a BAHD acyltransferase polypeptide with at least 99% amino acid sequence identity to SEQ ID NO:8 that exhibits FMT activity, PMT activity, and BMT activity.

16. The recombinant nucleic acid of claim 1, wherein the nucleic acid segment encodes a BAHD acyltransferase polypeptide with at least 95% amino acid sequence identity to SEQ ID NO:12 that exhibits pBMT activity.

17. The recombinant nucleic acid of claim 1, wherein the nucleic acid segment encodes a BAHD acyltransferase polypeptide with at least 95% amino acid sequence identity to SEQ ID NO:14 that exhibits FMT activity, PMT activity, or any combination thereof.

18. The recombinant nucleic acid of claim 1, wherein the nucleic acid segment encodes a BAHD acyltransferase polypeptide with at least 99% amino acid sequence identity to SEQ ID NO:14 that exhibits FMT activity and PMT activity.

19. The recombinant nucleic acid of claim 1, wherein the nucleic acid segment encodes a BAHD acyltransferase polypeptide with at least 95% amino acid sequence identity to SEQ ID NO:16 that exhibits FMT activity, PMT activity, or any combination thereof.

20. The recombinant nucleic acid of claim 1, wherein the nucleic acid segment encodes a BAHD acyltransferase polypeptide with at least 99% amino acid sequence identity to SEQ ID NO:16 that exhibits FMT activity and PMT activity.

21. The recombinant nucleic acid of claim 1, wherein the nucleic acid segment encodes a BAHD acyltransferase polypeptide with at least 95% amino acid sequence identity to SEQ ID NO:18 that exhibits FMT activity.

22. The recombinant plant cell of claim 3, wherein the nucleic acid segment encodes a BAHD acyltransferase polypeptide with at least 95% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, benzoyl-CoA:monolignol transferase (BMT) activity, or any combination thereof.

23. The recombinant plant cell of claim 3, wherein the nucleic acid segment encodes a BAHD acyltransferase polypeptide with at least 99% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, and benzoyl-CoA:monolignol transferase (BMT) activity.

24. The recombinant plant cell of claim 3, wherein the nucleic acid segment encodes a BAHD acyltransferase polypeptide with at least 95% amino acid sequence identity to SEQ ID NO:4 that exhibits pBMT activity, AMT activity, BMT activity, or any combination thereof.

25. The recombinant plant cell of claim 3, wherein the nucleic acid segment encodes a BAHD acyltransferase polypeptide with at least 99% amino acid sequence identity to SEQ ID NO:4 that exhibits pBMT activity, AMT activity, and BMT activity.

26. The recombinant plant cell of claim 3, wherein the nucleic acid segment encodes a BAHD acyltransferase polypeptide with at least 95% amino acid sequence identity to SEQ ID NO:6 that exhibits pBMT activity, AMT activity, BMT activity, or any combination thereof.

27. The recombinant plant cell of claim 3, wherein the nucleic acid segment encodes a BAHD acyltransferase polypeptide with at least 99% amino acid sequence identity to SEQ ID NO:6 that exhibits pBMT activity, AMT activity, and BMT activity.

28. The recombinant plant cell of claim 3, wherein the nucleic acid segment encodes a BAHD acyltransferase polypeptide with at least 95% amino acid sequence identity to SEQ ID NO:8 that exhibits FMT activity, PMT activity, BMT activity, or any combination thereof.

29. The recombinant plant cell of claim 3, wherein the nucleic acid segment encodes a BAHD acyltransferase polypeptide with at least 99% amino acid sequence identity to SEQ ID NO:8 that exhibits FMT activity, PMT activity, and BMT activity.

30. The recombinant plant cell of claim 3, wherein the nucleic acid segment encodes a BAHD acyltransferase polypeptide with at least 95% amino acid sequence identity to SEQ ID NO:12 that exhibits pBMT activity.

31. The recombinant plant cell of claim 3, wherein the nucleic acid segment encodes a BAHD acyltransferase polypeptide with at least 95% amino acid sequence identity to SEQ ID NO:14 that exhibits FMT activity, PMT activity, or any combination thereof.

32. The recombinant plant cell of claim 3, wherein the nucleic acid segment encodes a BAHD acyltransferase polypeptide with at least 99% amino acid sequence identity to SEQ ID NO:14 that exhibits FMT activity and PMT activity.

33. The recombinant plant cell of claim 3, wherein the nucleic acid segment encodes a BAHD acyltransferase polypeptide with at least 95% amino acid sequence identity to SEQ ID NO:16 that exhibits FMT activity, PMT activity, or any combination thereof.

34. The recombinant plant cell of claim 3, wherein the nucleic acid segment encodes a BAHD acyltransferase polypeptide with at least 99% amino acid sequence identity to SEQ ID NO:16 that exhibits FMT activity and PMT activity.

35. The recombinant plant cell of claim 3, wherein the nucleic acid segment encodes a BAHD acyltransferase polypeptide with at least 95% amino acid sequence identity to SEQ ID NO:18 that exhibits FMT activity.

36. The plant of claim 4, wherein the nucleic acid segment encodes a BAHD acyltransferase polypeptide with at least 95% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, benzoyl-CoA:monolignol transferase (BMT) activity, or any combination thereof.

37. The plant of claim 4, wherein the nucleic acid segment encodes a BAHD acyltransferase polypeptide with at least 99% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, and benzoyl-CoA:monolignol transferase (BMT) activity.

38. The plant of claim 4, wherein the nucleic acid segment encodes a BAHD acyltransferase polypeptide with at least 95% amino acid sequence identity to SEQ ID NO:4 that exhibits pBMT activity, AMT activity, BMT activity, or any combination thereof.

39. The plant of claim 4, wherein the nucleic acid segment encodes a BAHD acyltransferase polypeptide with at least 99% amino acid sequence identity to SEQ ID NO:4 that exhibits pBMT activity, AMT activity, and BMT activity.

40. The plant of claim 4, wherein the nucleic acid segment encodes a BAHD acyltransferase polypeptide with at least 95% amino acid sequence identity to SEQ ID NO:6 that exhibits pBMT activity, AMT activity, BMT activity, or any combination thereof.

41. The plant of claim 4, wherein the nucleic acid segment encodes a BAHD acyltransferase polypeptide with at least 99% amino acid sequence identity to SEQ ID NO:6 that exhibits pBMT activity, AMT activity, and BMT activity.

42. The plant of claim 4, wherein the nucleic acid segment encodes a BAHD acyltransferase polypeptide with at least 95% amino acid sequence identity to SEQ ID NO:8 that exhibits FMT activity, PMT activity, BMT activity, or any combination thereof.

43. The plant of claim 4, wherein the nucleic acid segment encodes a BAHD acyltransferase polypeptide with at least 99% amino acid sequence identity to SEQ ID NO:8 that exhibits FMT activity, PMT activity, and BMT activity.

44. The plant of claim 4, wherein the nucleic acid segment encodes a BAHD acyltransferase polypeptide with at least 95% amino acid sequence identity to SEQ ID NO:12 that exhibits pBMT activity.

45. The plant of claim 4, wherein the nucleic acid segment encodes a BAHD acyltransferase polypeptide with at least 95% amino acid sequence identity to SEQ ID NO:14 that exhibits FMT activity, PMT activity, or any combination thereof.

46. The plant of claim 4, wherein the nucleic acid segment encodes a BAHD acyltransferase polypeptide with at least 99% amino acid sequence identity to SEQ ID NO:14 that exhibits FMT activity and PMT activity.

47. The plant of claim 4, wherein the nucleic acid segment encodes a BAHD acyltransferase polypeptide with at least 95% amino acid sequence identity to SEQ ID NO:16 that exhibits FMT activity, PMT activity, or any combination thereof.

48. The plant of claim 4, wherein the nucleic acid segment encodes a BAHD acyltransferase polypeptide with at least 99% amino acid sequence identity to SEQ ID NO:16 that exhibits FMT activity and PMT activity.

49. The plant of claim 4, wherein the nucleic acid segment encodes a BAHD acyltransferase polypeptide with at least 95% amino acid sequence identity to SEQ ID NO:18 that exhibits FMT activity.

50. The plant seed of claim 6, wherein the nucleic acid segment encodes a BAHD acyltransferase polypeptide with at least 95% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, benzoyl-CoA:monolignol transferase (BMT) activity, or any combination thereof.

51. The plant seed of claim 6, wherein the nucleic acid segment encodes a BAHD acyltransferase polypeptide with at least 99% amino acid sequence identity to SEQ ID NO:2 that exhibits p-hydroxybenzoyl-CoA:monolignol transferase (pBMT) activity, feruloyl-CoA:monolignol transferase (FMT) activity, p-coumaroyl-CoA:monolignol transferase (PMT) activity, acetyl-CoA:monolignol transferase (AMT) activity, and benzoyl-CoA:monolignol transferase (BMT) activity.

52. The plant seed of claim 6, wherein the nucleic acid segment encodes a BAHD acyltransferase polypeptide with at least 95% amino acid sequence identity to SEQ ID NO:4 that exhibits pBMT activity, AMT activity, BMT activity, or any combination thereof.

53. The plant seed of claim 6, wherein the nucleic acid segment encodes a BAHD acyltransferase polypeptide with at least 99% amino acid sequence identity to SEQ ID NO:4 that exhibits pBMT activity, AMT activity, and BMT activity.

54. The plant seed of claim 6, wherein the nucleic acid segment encodes a BAHD acyltransferase polypeptide with at least 95% amino acid sequence identity to SEQ ID NO:6 that exhibits pBMT activity, AMT activity, BMT activity, or any combination thereof.

55. The plant seed of claim 6, wherein the nucleic acid segment encodes a BAHD acyltransferase polypeptide with at least 99% amino acid sequence identity to SEQ ID NO:6 that exhibits pBMT activity, AMT activity, and BMT activity.

56. The plant seed of claim 6, wherein the nucleic acid segment encodes a BAHD acyltransferase polypeptide with at least 95% amino acid sequence identity to SEQ ID NO:8 that exhibits FMT activity, PMT activity, BMT activity, or any combination thereof.

57. The plant seed of claim 6, wherein the nucleic acid segment encodes a BAHD acyltransferase polypeptide with at least 99% amino acid sequence identity to SEQ ID NO:8 that exhibits FMT activity, PMT activity, and BMT activity.

58. The plant seed of claim 6, wherein the nucleic acid segment encodes a BAHD acyltransferase polypeptide with at least 95% amino acid sequence identity to SEQ ID NO:12 that exhibits pBMT activity.

59. The plant seed of claim 6, wherein the nucleic acid segment encodes a BAHD acyltransferase polypeptide with at least 95% amino acid sequence identity to SEQ ID NO:14 that exhibits FMT activity, PMT activity, or any combination thereof.

60. The plant seed of claim 6, wherein the nucleic acid segment encodes a BAHD acyltransferase polypeptide with at least 99% amino acid sequence identity to SEQ ID NO:14 that exhibits FMT activity and PMT activity.

61. The plant seed of claim 6, wherein the nucleic acid segment encodes a BAHD acyltransferase polypeptide with at least 95% amino acid sequence identity to SEQ ID NO:16 that exhibits FMT activity, PMT activity, or any combination thereof.

62. The plant seed of claim 6, wherein the nucleic acid segment encodes a BAHD acyltransferase polypeptide with at least 99% amino acid sequence identity to SEQ ID NO:16 that exhibits FMT activity and PMT activity.

63. The plant seed of claim 6, wherein the nucleic acid segment encodes a BAHD acyltransferase polypeptide with at least 95% amino acid sequence identity to SEQ ID NO:18 that exhibits FMT activity.

* * * * *